(12) United States Patent
Lloyd Potter et al.

(10) Patent No.: US 7,342,004 B2
(45) Date of Patent: Mar. 11, 2008

(54) THIOETHER SULPHAMATE STEROIDS AS STEROID INHIBITORS AND ANTI-CANCER COMPOUNDS

(75) Inventors: Barry Victor Lloyd Potter, The Oxford Science Park (GB); Michael John Reed, The Oxford Science Park (GB); Graham Keith Packham, The Oxford Science Park (GB); Matthew Paul Leese, The Oxford Science Park (GB)

(73) Assignee: Sterix Ltd., Berkshire (GB)

( * ) Notice: Subject to any disclaimer, the term of this patent is extended or adjusted under 35 U.S.C. 154(b) by 249 days.

(21) Appl. No.: 10/367,623

(22) Filed: Feb. 14, 2003

(65) Prior Publication Data

US 2004/0009959 A1 Jan. 15, 2004

Related U.S. Application Data

(63) Continuation-in-part of application No. PCT/GB01/03715, filed on Aug. 17, 2001, and a continuation-in-part of application No. PCT/GB01/03705, filed on Aug. 17, 2001.

(30) Foreign Application Priority Data

Aug. 18, 2000 (GB) ............................ 0020498.2
Jun. 7, 2001 (GB) ............................ 0113921.1

(51) Int. Cl.
*A61K 31/56* (2006.01)
*C07J 31/00* (2006.01)

(52) U.S. Cl. ................. 514/178; 514/182; 552/523
(58) Field of Classification Search ............... 552/523; 514/178, 182
See application file for complete search history.

(56) References Cited

U.S. PATENT DOCUMENTS

| | | | |
|---|---|---|---|
| 3,415,816 A * | 12/1968 | Clarke | 540/57 |
| 3,501,509 A * | 3/1970 | Kuo et al. | 552/625 |
| 4,988,684 A * | 1/1991 | Gourvest et al. | 514/177 |
| 6,011,024 A | 1/2000 | Reed et al. | |

FOREIGN PATENT DOCUMENTS

| | | | |
|---|---|---|---|
| EP | 0 240 717 | | 10/1987 |
| WO | WO 97/30041 | | 8/1997 |
| WO | WO 98/24802 | * | 6/1998 |
| WO | WO 98 24802 | | 6/1998 |
| WO | WO 99 33858 | | 7/1999 |
| WO | WO 99 64013 | | 12/1999 |

OTHER PUBLICATIONS

Purohit A et al: "Recent Advances in the Development of Steroid Sulphatase Inhibitors", Journal of Steroid Biochemistry and Molecular Biology, Elsevier Science Ltd., Oxford, GB, vol. 69, No. 1/6, 1999, pp. 227-238, XP000852540.
Purohitt, Atul et al: "The effect of 2-methoxyoestrone-3-0-sulphamate on the growth of breast cancer cells and induced mammary tumours" retrieved from STN Database accession No. 133:38406, XP002182502, 2000.
Singh, A et al: "Inhibition of deoxyglucose uptake in MCF-7 breast cancer cells by 2-methoxyestrone and 2-methoxyestrone-3-0-sulfamate" retrieved from STN Database accession No. 132:318130, XP002182503, 2000.
Purohit A et al: "The Development of A-Ring Modified Analogues of Oestrone-3-0-Sulphamate as Potent Steroid Sulphastase Inhibitors with Reduced Oestrogenicity" Journal of Steroid Biochemistry and Molecular Biology, Elsevier Science Ltd., Oxford, GB, vol. 64, No. 5, 1998, pp. 269-275, XP000852539.
Howarth N M et al: "Estrone Sulfamates: Potent Inhibitors of Estrone Sulfatase with Therapeutic Potential" Journal of Medicinal Chemistry, American Chemical Society, Washington, US, vol. 37, No. 2, Jan. 21, 1994, pp. 219-221, XP000652211.
Cushman M et al: "Snythesis, Antitubulin and Antimitotic Activity, and Cytotoxicity of Analogs of 2-Methoxyestradiol, and Endogenous Mammalian Metabolite of Estradiol that Inhibits Tubulin Polymerization by Binding to the Colchicine Binding Site" Journal of Medicinal Chemistry, American Chemical Society. Washington, US, vol. 38, No. 12, 1995, pp. 2041-2049, XP002055798.
Cushman et al.: "Synthesis of Analogs of 2-Methoxyestradiol with Enhanced Inhieitory Effects of Tubulin Polymerization and Cancer Cell Growth", J. Med. Chem., vol. 40, 1997, pp. 2323-2334, XP002186112.
Schneider et al.: "Antiestrogen Action of 2-Hydroxyestrone on MCF-7 Human Breast Cancer Cells", Journal of Biological Chemistry, vol. 259, No. 8, 1984, pp. 4840-4845, XP002186113.
Rajan R et al.: "Estrogen Effects on Nadh Oxidase and Superoxide Dismutase in Prepubertal Female Rats", Steroids, Elsevier Science Publishers, New York, NY, US, vol. 40, No. 6, Dec. 1, 1982, pp. 651-660, XP002059348.
Kong Q et al.: "Antioxidant Inhibition-Based Strategy for Cancer Therapy" Proceedings of the 90th Annual Meeting of Research, Philadelphia, PA, Apr. 10-14, 1999, Proceedings of the Annual Meeting of the American Association for Cancer Research, Philadelphia, PA: AACR, US, vol. 40, Mar. 1999, pp. 53, Abstract, XP000882941.
Huang et al.: "Superoxide Dismutase as a Target for the Selective Killing of Cancer Cells", Nature, vol. 407, Sep. 21, 2000, pp. 390-395, XP002186114.
Kachadourian et al.:"2-Methoxyestradiol does not Inhibit Superoxide Dismutase", Arch. Biochem. Biophys., vol. 392, No. 2, Aug. 15, 2001, pp. 349-353, XP002186115.
"Woo et al., Heteroatom-Substituted Analogues of the Active-Site Directed Inhibitor Estra-1,3,5(10)-Trien-17-One-3-Sulphamate Inhibit Estrone Sulphatase by a Different Mechanism" J. Steroid BIochem. Molec. Biol. 1996 57(1/2):79-88.

* cited by examiner

*Primary Examiner*—Barbara P. Badio
(74) *Attorney, Agent, or Firm*—Frommer Lawrence & Haug LLP; Thomas J. Kowalski; Angela M. Collison

(57) ABSTRACT

There is provided use of a compound of Formula XI:

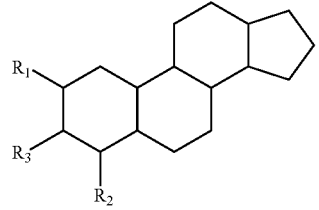

Formula XI wherein $R_3$ is a sulphamate group and at least of $R_1$ or $R_2$ is a thioether group as disclosed by the present specification, capable of inhibiting steroid sulphatase.

8 Claims, 3 Drawing Sheets

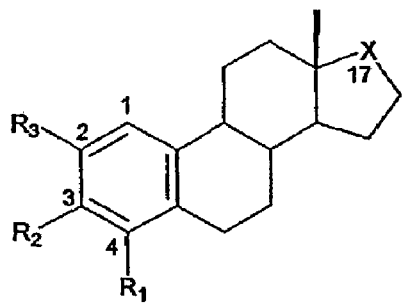

| $R_1$ | $R_2$ | $R_3$ | X | |
|---|---|---|---|---|
| H | OH | MeS | CH($\beta$-OH) | 1 |
| H | OH | EtO | CH($\beta$-OH) | 2 |
| H | OH | MeO | CH($\beta$-OH) | 3 |
| H | OH | MeO | CH($\alpha$-OH) | 4 |
| H | OH | MeO | C=O | 5 |
| H | OH | EtS | CH($\beta$-OH) | 6 |
| H | OH | EtO | C=O | 7 |
| H | OH | MeS | C=O | 8 |
| H | $NH_2$ | MeO | C=O | 9 |
| H | OH | EtS | C=O | 10 |
| H | OH | F | C=O | 11 |
| H | OH | Cl | C=O | 12 |
| H | OH | MeO | C($\beta$-OH)($\alpha$-Bn) | 13 |
| H | OH | $H_2C$=$CHCH_2$ | C=O | 15 |
| H | OH | I | C=O | 16 |
| H | OH | $CHF_2$ | C=O | 17 |
| H | OH | MeSO | C=O | 18 |
| H | OH | $MeSO_2$ | C=O | 19 |
| H | OH | $NO_2$ | C=O | 20 |
| H | OH | Et | C=O | 21 |
| $NO_2$ | OH | MeO | C=O | 22 |
| H | OH | MeO | C[$\beta$-OH][$\alpha$-(4-$^t$Bu)Bn] | 23 |
| H | $OSO_2NH_2$ | H | C=O | 24 |
| H | $OSO_2NH_2$ | MeO | C=O | 25 |
| H | $OSO_2NH_2$ | Et | C=O | 26 |

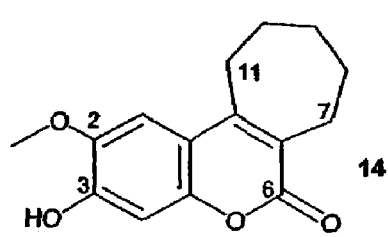

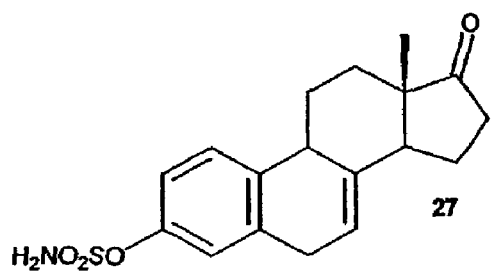

Figure 1 Structures of compounds 1 to 27

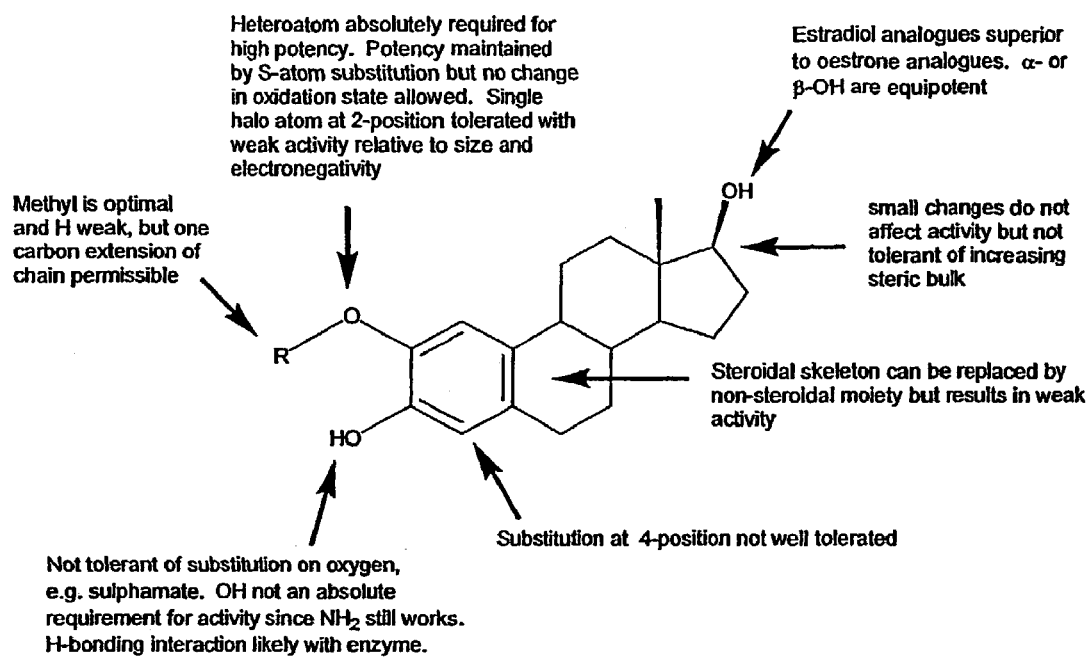
Figure 2. Summary of the structure-activity relationships for SOD inhibition for the compounds studied.

THIOETHER SULPHAMATE STEROIDS AS STEROID INHIBITORS AND ANTI-CANCER COMPOUNDS

CROSS-REFERENCE TO RELATED APPLICATIONS

This application is a continuation-in-part application of International Patent Application PCT/GB01/03715 filed Aug. 17, 2001 designating the U.S., and published as WO 02/15910 on Feb. 28, 2002; the present application is also a continuation-in-part application of International Patent Application PCT/GB01/03705 filed Aug. 17, 2001 designating the U.S., and published as WO 02/16394 on Feb. 28, 2002. WO 02/16394 claims priority to UK application number 0020498.2, filed Aug. 18, 2000. WO 02/15910 also claims priority to UK application number 0020498.2, and also claims priority to UK application 0113921.1 filed Jun. 7, 2001.

Each of these applications and each of the documents cited in each of these applications ("application cited documents"), and each document referenced or cited in the application cited documents, either in the text or during the prosecution of those applications, as well as all arguments in support of patentability advanced during such prosecution, are hereby incorporated herein by reference. Various documents are also cited in this text ("application cited documents"). Each of the application cited documents, and each document cited or referenced in the application cited documents, is hereby incorporated herein by reference.

FIELD OF INVENTION

The present invention relates to a compound.
The present invention also relates to a use.
In particular the present invention relates to a use of a compound for the manufacture of a medicament to inhibit superoxide dismutase (SOD). In other aspects the present invention relates to a compound and to a pharmaceutical composition comprising the compound. The present invention also relates to the use of the compound or composition in therapy applications.

BACKGROUND TO THE INVENTION

Evidence suggests that oestrogens are the major mitogens involved in promoting the growth of tumours in endocrine-dependent tissues, such as the breast and endometrium. Although plasma oestrogen concentrations are similar in women with or without breast cancer, breast tumour oestrone and oestradiol levels are significantly higher than in normal breast tissue or blood. In situ synthesis of oestrogen is thought to make an important contribution to the high levels of oestrogens in tumours and therefore inhibitors, in particular specific inhibitors, of oestrogen biosynthesis are of potential value for the treatment of endocrine-dependent tumours.

Over the past two decades, there has been considerable interest in the development of inhibitors of the aromatase pathway—which converts the androgen precursor androstenedione to oestrone. However, there is now evidence that the oestrone sulphatase (E1-STS) pathway, i.e. the hydrolysis of oestrone sulphate to oestrone (E1S to E1), as opposed to the aromatase pathway, is the major source of oestrogen in breast tumours. This theory is supported by a modest reduction of plasma oestrogen concentration in postmenopausal women with breast cancer treated by aromatase inhibitors, such as aminoglutethimide and 4-hydroxyandrostenedione, and also by the fact that plasma E1S concentration in these aromatase inhibitor-treated patients remains relatively high. The long half-life of E1S in blood (10-12 h) compared with the unconjugated oestrogens (20 min) and high levels of steroid sulphatase activity in liver and, normal and malignant breast tissues, also lend support to this theory.

PCT/GB92/01587 teaches novel steroid sulphatase inhibitors and pharmaceutical compositions containing them for use in the treatment of oestrone dependent tumours, especially breast cancer. These steroid sulphatase inhibitors are sulphamate esters, such as N,N-dimethyl oestrone-3-sulphamate and, preferably, oestrone-3-sulphamate (otherwise known as "EMATE"). EMATE has the following structure:

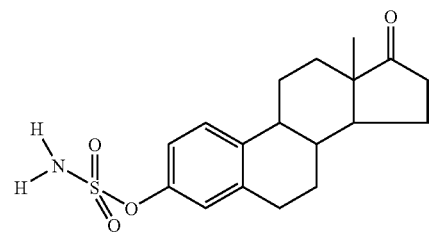

It is known that EMATE is a potent E1-STS inhibitor as it displays more than 99% inhibition of E1-STS activity in intact MCF-7 cells at 0.1 mM. EMATE also inhibits the E1-STS enzyme in a time- and concentration-dependent manner, indicating that it acts as an active site-directed inactivator. Although EMATE was originally designed for the inhibition of E1-STS, it also inhibits dehydroepiandrosterone sulphatase (DHA-STS), which is an enzyme that is believed to have a pivotal role in regulating the biosynthesis of the oestrogenic steroid androstenediol. Also, there is now evidence to suggest that androstenediol can be of even greater importance as a promoter of breast tumour growth. EMATE is also active in vivo as almost complete inhibition of rat liver E1-STS (99%) and DHA-STS (99%) activities resulted when it is administered either orally or subcutaneously. In addition, EMATE has been shown to have a memory enhancing effect in rats. Studies in mice have suggested an association between DHA-STS activity and the regulation of part of the immune response. It is thought that this can also occur in humans. The bridging O-atom of the sulphamate moiety in EMATE is important for inhibitory activity. Thus, when the 3-O-atom is replaced by other heteroatoms as in oestrone-3-N-sulphamate and oestrone-3-S-sulphamate, these analogues are weaker non-time-dependent inactivators.

Although optimal potency for inhibition of E1-STS can have been attained in EMATE, it is possible that oestrone can be released during sulphatase inhibition and that EMATE and its oestradiol congener can possess oestrogenic activity.

Ahmed et al (Biochem Biophys Res Commun Jan. 27, 1999;254(3):811-5) report on a structure-activity relationship study of steroidal and nonsteroidal inhibitors of STS.

The present invention seeks to provide novel compounds suitable for the inhibition of E1-STS as well as other therapeutic applications.

Additionally, estrogens undergo serial hydroxylation, methylation and conjugation reactions and recent evidence demonstrates that at least some of the products of these reactions possess unique biological activities independent of the classical oestrogen receptor (ER). 2-Methoxyestradiol (2-MeOE2) is a hydroxylation and methylation derivative of 17β-estradiol and has received considerable interest as an endogenous growth inhibitory and cytotoxic agent with potential use for cancer therapy.

2-MeOE2 inhibits the growth and/or promotes apoptosis of many malignant cell types, including ER positive and negative human breast cancer and leukaemic cell lines and primary chronic lymphocytic leukaemia cells. Oral administration of 2-MeOE2 inhibits the in vivo growth of transplanted human tumours in immunodeficient mice. In addition to its direct effects on the proliferation and survival of cancer cells, 2-MeOE2 also possesses significant anti-angiogenic activity.

We have generated a series of natural and synthetic oestrone and oestradiol derivatives to further examine the biological effects of this class of molecules and to identify compounds with enhanced activity. Of particular note, we showed that the 3-O-sulfamoylated derivatives of 2-methoxyestrone and 2-ethylestrone (2-methoxyestrone-3-O-sulfamate and 2-ethylestrone-3-O-sulfamate, respectively) were significantly more effective in inhibiting the growth and survival of breast cancer cells relative to their parental oestrones and 2-MeOE2 [Purohit et al 1999; MacCarthy-Morrogh et al 2000].

2-MeOE2 binds to the colchicine binding site on tubulin, and inhibits the polymerisation of tubulin dimers to give microtubules. 2-MeOE2 arrests cells in mitosis and induction of apoptosis is associated with phosphorylation of the anti-apoptotic BCL-2 protein. This is consistent with tubulin as a major target for 2-MeOE2 since other structurally diverse anti-tubulin agents, such as vincristine and paclitaxel have similar effects in cells. The enhanced activity of the 3-O-sulfamoylated oestrones was associated with more potent inhibition of tubulin polymerisation, enhanced mitotic arrest and apoptosis, and an increase in BCL-2 phosphorylation relative to parental compounds and 2-MeOE2.

More recently, 2-MeOE2 has been shown to inhibit the activity of both CuZn and Mn superoxide dismutases (SOD). SOD catalyse the breakdown of superoxide radical and are essential enzymes in protecting cells from reactive oxygen species (ROS). Cancer cells are thought to be particularly sensitive to inhibition of SOD, because of their enhanced production of superoxide ions and their reduced SOD expression. Inhibition of SOD activity and subsequent increase in ROS has been suggested to play a major role in induction of apoptosis by 2-MeOE2. In support of this idea Huang et al., showed that in addition to 2-MeOE2, 2-MeOE1 and 2-hydroxyestradiol, but not oestradiol or oestrone, also inhibited SOD and induced apoptosis. However, both of these compounds would also be expected to inhibit tubulin polymerisation to some extent and therefore this small series of compounds would not differentiate between these two modes of action. Therefore, it is not clear what are the key structural features of estrogens required for optimal activity.

The present invention seeks to provide novel compounds suitable for the inhibition of SOD as well as other therapeutic applications.

SUMMARY ASPECTS OF THE PRESENT INVENTION

The present invention is based on the surprising finding that certain compounds could be used as effective steroid sulphatase inhibitors and/or as agents that can influence cell cycling and/or as agents that can influence apoptosis.

In one aspect, the present invention is based on the surprising finding that certain hydrocarbylsulphanyl compounds could be used as effective steroid sulphatase inhibitors and/or as modulators of cell cycling and/or as modulators of apoptosis.

The term "hydrocarbylsulphanyl" means a group that comprises at least hydrocarbyl group (as herein defined) and sulphur. That sulphur group can be optionally oxidised.

The hydrocarbylsulphanyl compounds comprise at least one hydrocarbylsulphanyl group that is a substituent of a ring system compound. The ring system compounds comprise at least one ring component. That ring component comprises at least 4 atoms in the ring. Typically, those 4 atoms will be carbon atoms. Thus, typically, that ring component will be a hydrocarbyl group. The ring system compound also includes one or more of a sulphamate group, a phosphonate group, a thiophosphonate group, a sulphonate group or a sulphonamide group as further substituent(s) on the ring system. At least one of the sulphamate group, the phosphonate group, the thiophosphonate group, the sulphonate group or the sulphonamide group is a substituent on the ring component. In a preferred aspect, the hydrocarbylsulphanyl group(s) will be substituents on atom(s) that are adjacent to the atom which bears the at least one sulphamate group, phosphonate group, thiophosphonate group, sulphonate group or sulphonamide group.

The present invention is also based on the surprising finding that certain compounds could be used as effective superoxide dismutase (SOD) inhibitors and/or as agents that can influence apoptosis.

In one aspect, the present invention is based on the surprising finding that certain substituted cyclic compounds could be used as effective superoxide dismutase inhibitors and/or as modulators of apoptosis.

The substituted cyclic compounds comprise at least one group containing O or S that is a substituent of a ring system. The ring system compounds comprise at least one ring component. That ring component comprises at least 4 atoms in the ring. Typically, those 4 atoms will be carbon atoms. Thus, typically, that ring component will be a hydrocarbyl group.

The compounds of the present invention can comprise other substituents. These other substituents can, for example, further increase the activity of the compounds of the present invention and/or increase stability (ex vivo and/or in vivo).

DESCRIPTION OF THE FIGURES

FIG. 1 is a schematic and chart which show the structures of compounds 1 through 27.

FIG. 2 is a schematic depicting a summary of the structure-activity relationships for SOD inhibition for the compounds studied.

DETAILED DESCRIPTION OF THE PRESENT INVENTION

Figure 3:
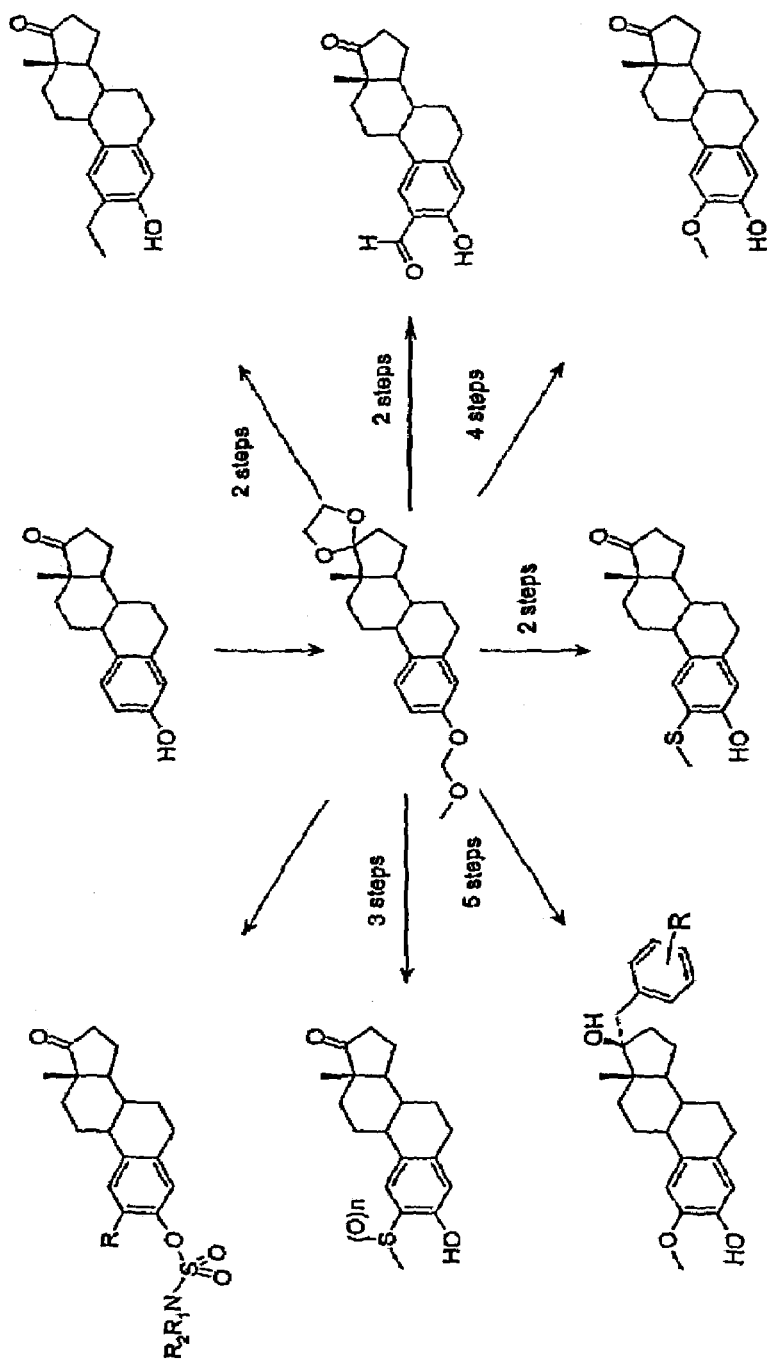
FIG. 3 is a schematic depicting the ability to selectively access a wide range of substituted estrones through the use of a bis-protected estrone intermediate.

According to one aspect of the present invention, there is provided use of a compound in the manufacture of a medicament to inhibit superoxide dismutase (SOD) or for use in the therapy of a condition or disease associated with SOD wherein the compound is of Formula I Formula I

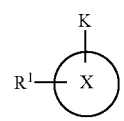

wherein: X is a ring having at least 4 atoms in the ring; K is a hydrocarbyl group; $R^1$ is a halogen or a group of the formula -$L^1$-Z-$R^{1'}$, wherein $L^1$ is an optional linker group, Z is O or S and $R^{1'}$ is a hydrocarbyl group or H; with the proviso that the compound is other than 2-methoxy-17β-oestradiol, 2-methoxyoestrone and 2-hydroxyestradiol.

According to one aspect of the present invention, there is provided a compound having Formula IX

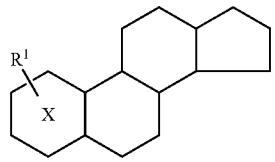

Formula IX wherein $R^1$ is a group of the formula -$L^1$-S-$R^{1'}$, wherein $L^1$ is an optional linker group, and $R^{1'}$ is a hydrocarbyl group or H.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with SOD and/or apoptosis.

According to one aspect of the present invention, there is provided the use of a compound according to the present invention in the manufacture of a medicament for use in the therapy of a condition or disease associated with adverse SOD and/or apoptosis.

According to one aspect of the present invention, there is provided a method comprising (a) performing a superoxide dismutase assay with one or more candidate compounds of Formula I; (b) determining whether one or more of said candidate compounds is/are capable of modulating SOD activity and/or apoptosis; and (c) selecting one or more of said candidate compounds that is/are capable of modulating SOD activity and/or apoptosis.

According to one aspect of the present invention, there is provided a method comprising (a) performing a superoxide dismutase assay with one or more candidate compounds having of Formula I; (b) determining whether one or more of said candidate compounds is/are capable of inhibiting SOD activity; and (c) selecting one or more of said candidate compounds that is/are capable of inhibiting SOD activity and/or apoptosis.

In any one of the methods of the present invention, one or more additional steps can be present. For example, the method can also include the step of modifying the identified candidate compound (such as by chemical and/or enzymatic techniques) and the optional additional step of testing that modified compound for SOD inhibition effects (which can be to see if the effect is greater or different). By way of further example, the method can also include the step of determining the structure (such as by use of crystallographic techniques) of the identified candidate compound and then performing computer modelling studies—such as to further increase its SOD inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as protein binding studies.

According to one aspect of the present invention, there is provided a compound identified by the method of the present invention.

The present invention also encompasses the novel compounds of the present invention (such as those presented herein), as well as processes for making same (such as the processes presented herein) as well as novel intermediates (such as those presented herein) for use in those processes.

One key aspect of the present invention is that the compounds of the present invention can act as SOD inhibitors.

The compounds of the present invention can be used for the in the therapy of a condition or disease associated with SOD, adverse SOD levels and/or apoptosis. These therapies included therapies to induce apoptosis and to overcome resistance to apoptosis. This is advantageous in condition where cells should have died but have not. Yet further the inhibitors of the present invention can be utilised to counter defects in other enzymes involved in the regulation of reactive oxygen species. Thus in a further aspect the present invention provides a therapy or use of a compound of the present invention for the regulation of a reactive oxygen metabolic pathway.

Another aspect of the compounds of the present invention is that they can be potent in vivo.

Some of the compounds of the present invention can be non-oestrogenic compounds.

Here, the term "non-oestrogenic" means exhibiting no or substantially no oestrogenic activity.

Another aspect is that some of the compounds can not be capable of being metabolised to compounds which display or induce hormonal activity.

Some of the compounds of the present invention are also advantageous in that they can be orally active.

Some of the compounds of the present invention can useful for the treatment of cancer, such as breast cancer, as well as (or in the alternative) non-malignant conditions, such as the prevention of auto-immune diseases, particularly when pharmaceuticals need to be administered from an early age.

Thus, some of the compounds of the present invention are also believed to have therapeutic uses other than for the treatment of cancer, such as the treatment of autoimmune diseases.

The compounds of the present invention can also be useful as an inducer of apoptosis.

According to another aspect of the present invention, there is provided a compound of Formula XI

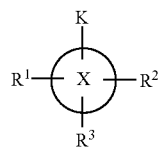

Formula XI wherein X is a ring having at least 4 atoms in the ring; K is a hydrocarbyl group; $R^1$ is an optional group of the formula -$L^1$-S-$R^{1'}$, wherein $L^1$ is an optional linker group and $R^{1'}$ is a hydrocarbyl group; $R^2$ is an optional group of the formula -$L^2$-S-$R^{2'}$, wherein $L^2$ is an optional linker group and $R^{2'}$ is a hydrocarbyl group; $R^3$ is any one of a sulphamate group, a phosphonate group, a thiophosphonate group, a sulphonate group or a sulphonamide group; wherein at least one of $R^1$ and $R^2$ is present; and wherein said compound is capable of inhibiting steroid sulphatase (STS) activity and/or is capable of acting as a modulator of cell cycling and/or as a modulator of apoptosis and/or as a modulator of cell growth (e.g growth inhibitor).

According to another aspect of the present invention, there is provided a method comprising (a) performing a steroid sulphatase assay with one or more candidate compounds of Formula XI; (b) determining whether one or more of said candidate compounds is/are capable of modulating STS activity and/or cell cycling and/or cell growth and/or apoptosis; and (c) selecting one or more of said candidate compounds that is/are capable of modulating STS activity and/or cell cycling and/or cell growth and/or apoptosis.

According to another aspect of the present invention, there is provided a method comprising (a) performing a steroid sulphatase assay with one or more candidate compounds having of Formula XI; (b) determining whether one or more of said candidate compounds is/are capable of inhibiting STS activity; and (c) selecting one or more of said candidate compounds that is/are capable of inhibiting STS activity and/or cell cycling and/or cell growth and/or apoptosis.

In any one of the methods of the present invention, one or more additional steps can be present. For example, the method can also include the step of modifying the identified candidate compound (such as by chemical and/or enzymatic techniques) and the optional additional step of testing that modified compound for STS inhibition effects (which can be to see if the effect is greater or different). By way of further example, the method can also include the step of determining the structure (such as by use of crystallographic techniques) of the identified candidate compound and then performing computer modelling studies—such as to further increase its STS inhibitory action. Thus, the present invention also encompasses a computer having a dataset (such as the crystallographic co-ordinates) for said identified candidate compound. The present invention also encompasses that identified candidate compound when presented on a computer screen for the analysis thereof—such as protein binding studies.

According to one aspect of the present invention, there is provided a compound identified by the method of the present invention.

According to one aspect of the present invention, there is provided a compound according to the present invention for use in medicine.

According to one aspect of the present invention, there is provided a pharmaceutical composition comprising the compound according to the present invention optionally admixed with a pharmaceutically acceptable carrier, diluent, excipient or adjuvant.

According to one aspect of the present invention, there is provided the use of a compound according to the present invention in the manufacture of a medicament for use in the therapy of a condition or disease associated with STS and/or cell cycling and/or apoptosis and/or cell growth.

According to one aspect of the present invention, there is provided the use of a compound according to the present invention in the manufacture of a medicament for use in the therapy of a condition or disease associated with adverse STS levels and/or cell cycling and/or apoptosis and/or cell growth.

The present invention also encompasses the novel compounds of the present invention (such as those presented herein), as well as processes for making same (such as the processes presented herein) as well as novel intermediates (such as those presented herein) for use in those processes.

For ease of reference, these and further aspects of the present invention are now discussed under appropriate section headings. However, the teachings under each section are not necessarily limited to each particular section.

PREFERABLE ASPECTS

As discussed above the present invention provides use of a compound in the manufacture of a medicament to inhibit superoxide dismutase (SOD) or for use in the therapy of a condition or disease associated with SOD wherein the compound is of Formula I

Formula I wherein: X is a ring having at least 4 atoms in the ring; K is a hydrocarbyl group; $R^1$ is a halogen or a group of the formula $-L^1-Z-R^{1'}$, wherein $L^1$ is an optional linker group, Z is O or S and $R^{1'}$ is a hydrocarbyl group or H; with the proviso that the compound is other than 2-methoxy-17β-oestradiol, 2-methoxyoestrone and 2-hydroxyestradiol.

It will be understood that when Z is S depending on the oxidation state of the sulphur, the S can have other groups attached thereto. For example the S can be divalent, tri- or tetracoordinated. Examples of such groups which can be attached to the S include =O.

In one aspect the compound is other than 2-methoxy-oestradiol (i.e. 2-methoxy-17β-oestradiol and 2-methoxy-17α-oestradiol), 2-methoxyoestrone and 2-hydroxyestradiol.

Preferably the ring X is a 6 membered ring.

Preferably the compound of the present invention Formula II

Formula II

Group K need not be a cyclic structure. In this regard, group K can be a linear structure that can have the ability to conform to a ring like structure when in in vivo.

In a preferred aspect, group K is cyclic—so as to form the cyclic group K. In this aspect X is a ring and K is a cyclic group. Thus the compound is a polycyclic compound.

Cyclic group K need not necessarily be fused to ring X. In this regard, they can be separated by a suitable spacer group—which can be a hydrocarbyl group.

In a preferred aspect, cyclic group K is fused to ring X.

Group K can be a polycyclic group, which need not be a fused polycycle.

Preferably X in combination with K is a polycyclic ring structure. Thus, in a preferred aspect, group K and ring X make up a polycyclic compound. As indicated, here the term "polycyclic" includes fused and non-fused ring structures including combinations thereof.

At least one of the cyclic groups K and X can be a heterocyclic group (a heterocycle) or a non-heterocyclic group.

At least one of the cyclic groups K and X can be a saturated ring structure or an unsaturated ring structure (such as an aryl group).

Preferably, at least one of the cyclic groups is an aryl ring.

If the cyclic group is polycyclic some or all of the ring components of the compound can be fused together or joined via one or more suitable spacer groups.

The polycyclic compound can comprise a number of fused rings. In this aspect the fused rings can comprise any combination of different size rings, such as 3 six-membered rings (6,6,6), a six-membered ring, a seven-membered ring and a six-membered ring (6,7,6), a six-membered ring and two eight-membered rings (6,8,8) etc.

In one aspect the present invention relates to compounds wherein the polycyclic compounds are other than (6,6,7) rings. In a further aspect, the present invention relates to compounds wherein the polycyclic compounds only contain rings having other than 7 members.

The polycyclic compound can comprise at least two ring components, or at least three ring components, or at least four ring components.

Preferably the compound of the present invention is of Formula III

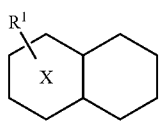

Formula III

Preferably the compound of the present invention is of Formula IV

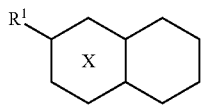

Formula IV

Preferably the compound of the present invention is of Formula V

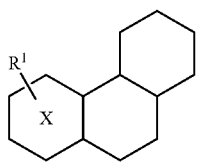

Formula V

Preferably the compound of the present invention is of Formula VI

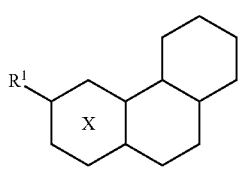

Formula VI

Preferably, the polycyclic compound comprises four ring components.

Preferred polycyclic compounds have a steroidal ring component, or bio-isosteres thereof.

In a preferred aspect X in combination with K is a steroidal ring structure—that is to say a cyclopentanophenanthrene skeleton, or bio-isosteres thereof.

As it is well known in the art, a classical steroidal ring structure has the generic formula of:

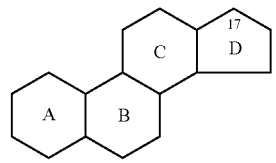

In the above formula, the rings have been labelled in the conventional manner.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere in the absence of the sulphamate group has steroidal properties.

In this regard, the structure of a preferred polycyclic structure can be presented as:

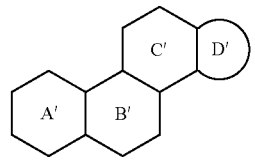

wherein each ring A', B', C' and D' independently represents a heterocyclic ring or a non-heterocyclic ring, which rings can be independently substituted or unsubstituted, saturated or unsaturated.

By way of example, any one or more of rings A', B', C' and D' can be independently substituted with suitable groups—such as an alkyl group, an aryl group, a hydroxy group, a halo group, a hydrocarbyl group, an oxyhydrocarbyl group etc.

An example of D' is a five or six membered non-heterocyclic ring having at least one substituent.

In one preferred embodiment, the ring D' is substituted with a ethinyl group.

If any one of rings A', B', C' and D' is a heterocyclic ring, then preferably that heterocyclic ring comprises a combination of C atoms and at least one N atom and/or at least one O atom. Other heterocyclic atoms can be present in the ring.

Examples of suitable, preferred steroidal nuclei rings A'-D' of the compounds of the present invention include rings A-D of dehydroepiandrosterone and oestrogens including oestrone. Preferred steroidal nuclei rings A'-D' of the compounds of the present invention include rings A-D of:

Oestrones and Substituted Oestrones, viz:
oestrone
2-OH-oestrone
4-OH-oestrone
6α-OH-oestrone
7α-OH-oestrone
16α-OH-oestrone
16β-OH-oestrone
2-MeO-oestrone 17-deoxyoestrone Oestradiols and Substituted Oestradiols, viz:
4-OH-17β-oestradiol
6α-OH-17β-oestradiol
7α-OH-17β-oestradiol
4-OH-17α-oestradiol
6α-OH-17α-oestradiol
7α-OH-17α-oestradiol
16α-OH-17α-oestradiol
16α-OH-17β-oestradiol
16β-OH-17α-oestradiol
16β-OH-17β-oestradiol
17α-oestradiol
17β-oestradiol
17α-ethinyl-17β-oestradiol
17β-ethinyl-17α-oestradiol
17-deoxyoestradiol Oestriols and Substituted Oestriols, viz:
oestriol
4-OH-oestriol
6α-OH-oestriol
7α-OH-oestriol
17-deoxyoestriol Dehydroepiandrosterones and Substituted Dehydroepiandrosterones, viz:
dehydroepiandrosterones
6α-OH-dehydroepiandrosterone
7α-OH-dehydroepiandrosterone
16α-OH-dehydroepiandrosterone
16β-OH-dehydroepiandrosterone
androstenediol In general terms the ring system A'B'C'D' can contain a variety of non-interfering substituents. In particular, the ring system A'B'C'D' can contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

In a preferred aspect X in combination with K mimics a steroidal structure. The term "mimic" as used herein means having a similar or different structure but having a similar functional effect. In other words, group K and ring X together can be a bio-isostere of the rings of a steroid, or an active part thereof.

In a preferred aspect, group K and ring X together can be a bio-isostere of the rings of oestrone, or a part thereof.

Preferably the compound of the present invention is of Formula VII

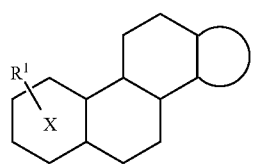

Formula VII

Preferably the compound of the present invention is of Formula VIII

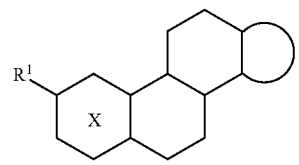

Formula VIII

Preferably the compound of the present invention is of Formula IX

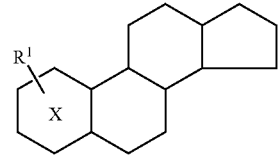

Formula IX

Preferably the compound of the present invention is of Formula X

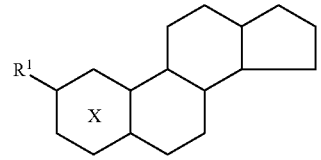

Formula X

The present invention provides novel compounds having Formula IX

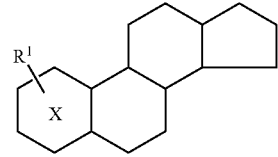

Formula IX and preferably having Formula X

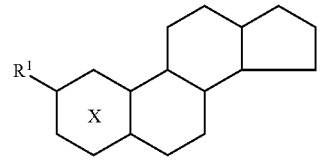

Formula X wherein $R^1$ is a group of the formula -$L^1$-S-$R^{1'}$, wherein $L^1$ is an optional linker group, and $R^{1'}$ is a hydrocarbyl group or H.

Preferably for the compound of the present invention $R^1$ is a group of the formula —S—$R^{1'}$.

Preferably for the compound of the present invention $R^{1'}$ is an alkyl group.

Preferably for the compound of the present invention $R^{1'}$ is a $C_1$-$C_{10}$ alkyl group.

Preferably for the compound of the present invention $R^{1'}$ is a $C_1$-$C_6$ alkyl group.

Preferably for the compound of the present invention $R^{1'}$ is a $C_1$-$C_3$ alkyl group.

Preferably for the compound of the present invention $R^{1'}$ is —$CH_3$ or —$CH_2CH_3$.

Preferably for the compound of the present invention $R^1$ is selected from —$SCH_3$, —$SCH_2CH_3$, —$S(O)CH_3$, and —$S(O)(O)CH_3$ In a further aspect the present invention also provides the compound described above for use in medicine.

In a further aspect the present invention also provides a pharmaceutical composition comprising the compound described above optionally admixed with a pharmaceutically acceptable carrier, diluent, excipient or adjuvant.

In a further aspect the present invention also provides use of the compound described above in the manufacture of a medicament for the inhibition of SOD or for use in the therapy of a condition or disease associated with SOD Further novel compounds are provided by the present invention. These compound include compounds 4, 9, 17, 22, 23 and 29. The structures of these compounds are given below 4
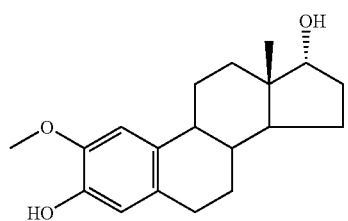

9
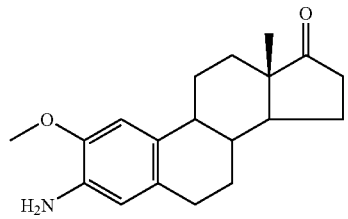

17
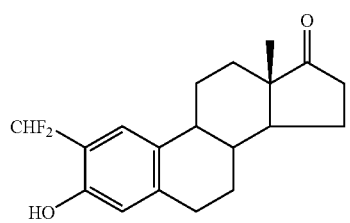

22
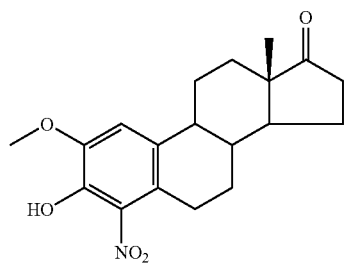

23
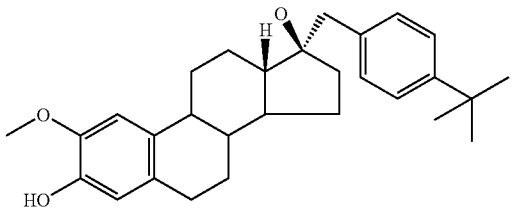

29
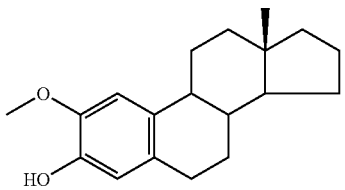

Thus in aspect of the invention there is provided a compound having the formula

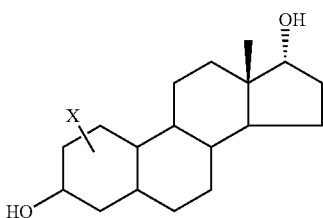

wherein X is an oxyhydrocarbyl group as defined herein a compound of the formula

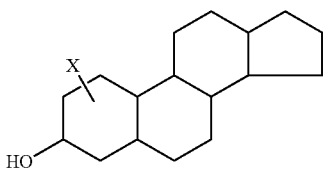

wherein X is a halohydrocarbyl group as defined below a compound of the formula

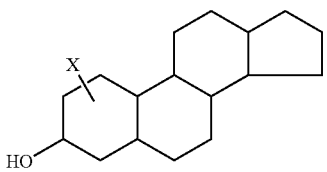

wherein X is a nitro group a compound of the formula

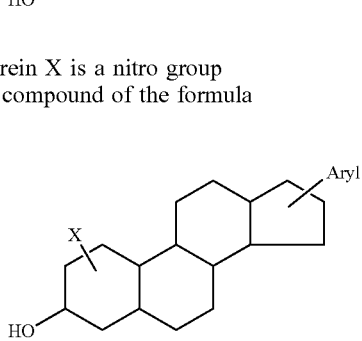

wherein X is an oxyhydrocarbyl group as defined herein and Aryl is an aryl group a compound of the formula

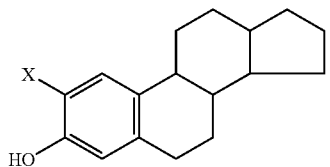

wherein X is an oxyhydrocarbyl group as defined herein

The term "halohydrocarbyl" group as used herein means a group comprising at least C, H and a halogen (i.e. Cl, Br, I and/or F) and can optionally comprise one or more other suitable substituents. Examples of such substituents can include oxy-, alkoxy-, nitro-, an alkyl group, a cyclic group etc. In addition to the possibility of the substituents being a cyclic group, a combination of substituents can form a cyclic group. If the oxyhydrocarbyl group comprises more than one C then those carbons need not necessarily be linked to each other. For example, at least two of the carbons can be linked via a suitable element or group. Thus, the oxyhydrocarbyl group can contain hetero atoms. Suitable hetero atoms will be apparent to those skilled in the art and include, for instance, sulphur and nitrogen.

We have surprisingly found that compounds containing a non-steroidal ring structure can act as described herein. Compounds for use in the present invention can not contain or be based on a steroid nucleus. In this regard, the polycyclic compound can contain or be based on a non-steroidal ring system—such as diethylstilboestrol, stilboestrol, coumarins, flavonoids, combrestatin and other ring systems. Other suitable non-steroidal compounds for use in or as the composition of the present invention can be found in U.S. Pat. No. 5,567,831. In preferred aspects of the invention when $R_1$ is a methoxy group or hydroxy group, X in combination with K is a nonsteroidal ring structure; and/or the compound for use in the present invention is non-steroidal; and/or X in combination with K is a non-steroidal ring structure In a highly preferred aspect the compound for use in the present invention is a compound selected from compounds of the formula

| | $R_1$ | $R_2$ | $R_3$ | X | |
|---|---|---|---|---|---|
| | H | OH | MeS | CH(β-OH) | 1 |
| | H | OH | EtO | CH(β-OH) | 2 |
| | H | OH | MeO | CH(β-OH) | 3 |
| | H | OH | EtS | CH(β-OH) | 4 |
| | H | OH | EtO | C=O | 6 |
| | H | OH | MeS | C=O | 7 |
| | H | NH$_2$ | MeO | C=O | 8 |
| | | | | | 9 |
| | H | OH | EtS | C=O | 10 |
| | H | OH | F | C=O | 11 |
| | H | OH | Cl | C=O | 12 |
| | H | OH | MeO | C(β-OH)(α-Bn) | 13 |
| | H | OH | H$_2$O=CHCH$_2$ | C=O | 15 |
| | H | OH | I | C=O | 16 |
| | H | OH | CHF$_2$ | C=O | 17 |
| | H | OH | MeSO | C=O | 18 |
| | H | OH | MeSO$_2$ | C=O | 19 |
| | H | OH | NO$_2$ | C=O | 20 |
| | H | OH | Et | C=O | 21 |
| | NO$_2$ | OH | MeO | C=O | 22 |
| | H | OH | MeO | C[β-OH][α-(4-$^t$Bu)Bn] | 23 |
| | H | OSO$_2$NH$_2$ | H | C=O | 24 |
| | H | OSO$_2$NH$_2$ | MeO | C=O | 25 |
| | H | OSO$_2$NH$_2$ | Et | C=O | 26 |

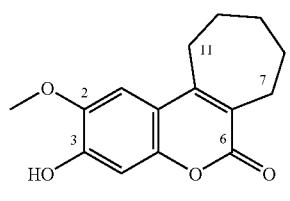

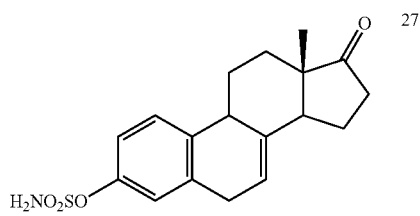

-continued

| R₁ | R₂ | R₃ | X |
|---|---|---|---|
| 28 | | | |
| 29 | | | |

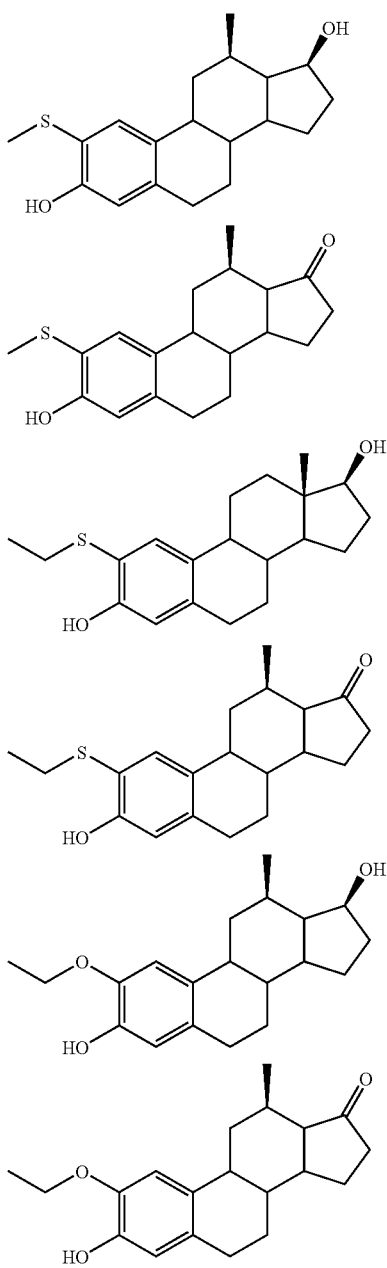

Highly preferred compounds are compounds of the formulae and

In a preferred aspect ring X is substituted with group R2. Thus in this aspect the compound for use in the present invention is

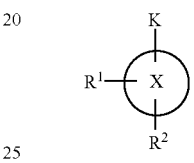

preferably

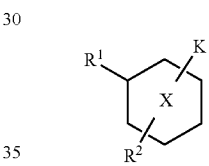

$R^2$ can be any suitable substituent. Examples of $R^2$ include —OH and amine or amide groups such as $NH_2$.

Preferably the group K and the ring X together will contain, inclusive of all substituents, a maximum of about 50 carbon atoms, more usually no more than about 30 to 40 carbon atoms.

In a preferred aspect the compounds of the present invention or for use therein are not substituted with a sulphamate group. As would be understood by one skilled in the art a sulphamate group is includes an ester of sulphamic acid, or an ester of an N-substituted derivative of sulphamic acid, or a salt thereof.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The present invention also covers novel intermediates that are useful to prepare the compounds of the present invention.

In another aspect of the invention, preferably the compound of the present invention is of Formula XII

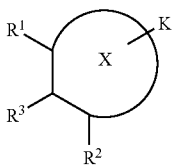

Formula XII wherein each of X, K, $R^1$, $L^1$, $R^{1'}$, $R^2$, $L^2$, $R^{2'}$, and $R^3$ have the above-mentioned meanings.

Preferably the compound of the present invention is of Formula XIII

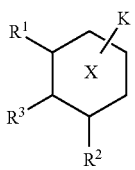

Formula XIII wherein each of X, K, $R^1$, $L^1$, $R^{1'}$, $R^2$, $L^2$, $R^{2'}$, and $R^3$ have the above-mentioned meanings.

Preferably the compound of the present invention is of Formula XIV

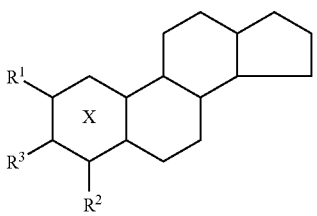

Formula XIV wherein each of X, K, $R^1$, $L^1$, $R^{1'}$, $R^2$, $L^2$, $R^{2'}$, and $R^3$ have the above-mentioned meanings.

Preferably, X in combination with K mimics a steroidal structure.

Preferably, K is a cyclic group.

Preferably, X is a six-membered ring.

Preferably, the ring X has six carbon atoms in the ring.

Preferably, group K and ring X are a steroid ring structure or a substituted derivative thereof.

Preferably, the $R^3$ group is at position 3 of the ring X.

Preferably, $R^3$ is a sulphamate group.

Preferably, the $R^1$ is at position 2 of the ring X.

Preferably, the $R^2$ is at position 4 of the ring X.

Preferably, $R^{1'}$ and/or $R^{2'}$ are alkyl groups.

Preferably, $R^{1'}$ and/or $R^{2'}$ are $C_1$-$C_{10}$, preferably $C_1$-$C_6$, preferably $C_1$-$C_3$ alkyl groups.

Preferably, $R^{1'}$ and/or $R^{2'}$ are —$CH_3$ or —$CH_2CH_3$.

Preferably the group K and the ring X together will contain, inclusive of all substituents, a maximum of about 50 carbon atoms, more usually no more than about 30 to 40 carbon atoms.

For some compounds of the present invention, it is highly preferred that X is a steroidal ring; wherein at least the D ring of X is substituted.

For some compounds of the present invention, it is highly preferred that X is a steroidal ring; wherein at least the 17 position of the D ring of X is substituted.

For some compounds of the present invention, it is highly preferred that X is a steroidal ring; wherein at least the 17 position of the D ring of X is substituted with a hydrocarbyl group, preferably an aryl group.

For some compounds of the present invention, it is highly preferred that X is a steroidal ring; wherein at least the A ring of X is substituted with an alkoxy group.

For some compounds of the present invention, it is highly preferred that X is a steroidal ring; wherein at least the 2 position of the A ring of X is substituted with an alkoxy group.

Preferably the alkoxy group is methoxy.

For some compounds of the present invention, it is highly preferred that X is a steroidal ring; wherein at least the A ring of X is substituted with an hydrocarbyl group.

For some compounds of the present invention, it is highly preferred that X is a steroidal ring; wherein at least the 2 position of the A ring of X is substituted with an alkyl group.

Preferably the alkyl group is ethyl.

For some compounds of the present invention, it is highly preferred that the compound comprises at least two or more of sulphamate group, a phosphonate group, a thiophosphonate group, a sulphonate group or a sulphonamide group.

For some compounds of the present invention, it is highly preferred that the compound comprises at least two sulphamate groups.

For some compounds of the present invention, it is highly preferred that the compound comprises at least two sulphamate groups, wherein said sulphamate groups are not on the same ring.

For some compounds of the present invention, it is highly preferred that X is a steroidal ring; wherein the A ring of X comprises at least one sulphamate group and wherein the D ring of X comprises at least one sulphamate group.

For some applications, preferably the compounds have no, or a minimal, oestrogenic effect.

For some applications, preferably the compounds have an oestrogenic effect.

For some applications, preferably the compounds have a reversible action.

For some applications, preferably the compounds have an irreversible action.

In one embodiment, the compounds of the present invention are useful for the treatment of breast cancer.

The present invention also covers novel intermediates that are useful to prepare the compounds of the present invention. For example, the present invention covers novel alcohol precursors for the compounds. By way of further example, the present invention covers bis protected precursors for the compounds. Examples of each of these precursors are presented herein. The present invention also encompasses a process comprising each or both of those precursors for the synthesis of the compounds of the present invention.

Two preferred compounds are compounds of the formulae

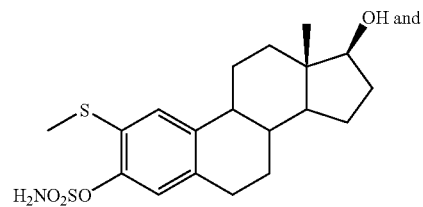

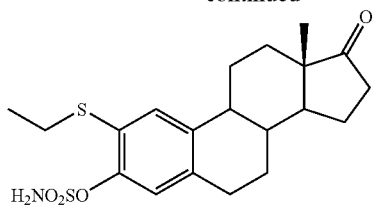

One key aspect of the present invention is that the sulphamate compounds of the present invention can act as STS inhibitors.

Another aspect of the compounds of the present invention is that they can be potent in vivo.

Some of the compounds of the present invention can be non-oestrogenic compounds. Here, the term "non-oestrogenic" means exhibiting no or substantially no oestrogenic activity.

Another aspect is that some of the compounds can not be capable of being metabolised to compounds which display or induce hormonal activity.

Some of the compounds of the present invention are also advantageous in that they can be orally active.

Some of the compounds of the present invention can useful for the treatment of cancer, such as breast cancer, as well as (or in the alternative) non-malignant conditions, such as the prevention of auto-immune diseases, particularly when pharmaceuticals can need to be administered from an early age.

Thus, some of the compounds of the present invention are also believed to have therapeutic uses other than for the treatment of endocrine-dependent cancers, such as the treatment of autoimmune diseases.

The compounds of the present invention can also be useful as an inducer of apoptosis.

The compounds of the present invention can also be useful as a cell growth inhibitors.

The following paragraphs relate to those compounds with formulas I through X.

Superoxide Dismutase

As discussed by Huang et al. Nature, Vol 407, 21 September 2000, 390-395 superoxide dismutases (SOD) are essential enzymes that eliminate superoxide radical ($O^{2-}$) and thus protect cells from damage induced by free radicals. The active $O^{2-}$ production and low SOD activity in cancer cells can render the malignant cells highly dependent on SOD for survival and sensitive to inhibition of SOD. Inhibition of SOD causes accumulation of cellular $O^{2-}$ and leads to free-radical-mediated damage to mito-chondrial membranes, the release of cytochrome c from mito-chondria and apoptosis of the cancer cells. Targeting SOD is a promising approach to the selective killing of cancer cells, and that mechanism-based combinations of SOD inhibitors with free-radical-producing agents can have clinical applications.

SOD Inhibitor

In accordance with the present invention, the compound of the present invention is capable of acting as an SOD inhibitor.

Here, the term "inhibitor" as used herein with respect to the compound of the present invention means a compound that can inhibit SOD activity—such as reduce and/or eliminate and/or mask and/or prevent the action of SOD. The SOD inhibitor can act as an antagonist.

The ability of compounds to inhibit superoxide dismutase activity can be assessed using the SOD assay of Protocol 1.

For some applications, preferably the compound of the present invention has at least about a 100 fold selectivity to a desired target (e.g. SOD), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention can have other beneficial properties in addition to or in the alternative to its ability to inhibit SOD activity.

Group $R^1$

Group $R^1$ of the compound for use in the present invention is a halogen or a group of the formula $-L^1-Z-R^{1'}$. $L^1$ is an optional linker group, Z is O or S and $R^{1'}$ is a hydrocarbyl group or H;

If present $L^1$ can be a hydrocarbyl group.

Preferably $L^1$ is selected from $C_1-C_{10}$ hydrocarbyl, $C_1-C_5$ hydrocarbyl or $C_1-C_3$ hydrocarbyl.

Preferably $L^1$ is selected from hydrocarbon groups, preferably $C_1-C_{10}$ hydrocarbon, $C_1-C_5$ hydrocarbon or $C_1-C_3$ hydrocarbon.

Preferably $L^1$ is selected from alkyl groups, $C_1-C_{10}$ alkyl, $C_1-C_5$ alkyl or $C_1-C_3$ alkyl.

The hydrocarbyl/hydrocarbon/alkyl of $L^1$ can be straight chain or branched and/or can be saturated or unsaturated.

In one aspect $L^1$ can be linked to the remainder of $R^1$.

In one aspect $R^1$ is a halogen. The halogen can be F, Cl, Br or I. In this aspect preferably the halogen is selected from F and Cl.

In one aspect $R^1$ is a group of the formula $-L^1-Z-R^{1'}$. $L^1$ is an optional linker group. When $L^1$ is present $R^1$ is a group of the formula $-L^1-Z-R^{1'}$. When $L^1$ is not present in one aspect $R^1$ is a group of the formula $-Z-R^{1'}$ Group Z can be O or S. For the avoidance of doubt O represent oxygen and S represents sulphur. In one aspect Z is O. In one aspect Z is S.

$R^{1'}$ is a hydrocarbyl group or H.

Preferably $R^{1'}$ is selected from $C_1-C_{10}$ hydrocarbyl, $C_1-C_5$ hydrocarbyl or $C_1-C_3$ hydrocarbyl.

Preferably $R^{1'}$ is selected from hydrocarbon groups, $C_1-C_{10}$ hydrocarbon, $C_1-C_5$ hydrocarbon or $C_1-C_3$ hydrocarbon.

In a preferred aspect $R^{1'}$ is an alkyl group.

Preferably $R^{1'}$ is a $C_2-C_{10}$ alkyl group, more preferably a $C_1-C_6$ alkyl group, more preferably a $C_1-C_3$ alkyl group, more preferably —$CH_3$ or —$CH_2CH_3$.

In further preferred aspects $R^{1'}$ is a $C_2-C_{10}$ alkyl group, preferably a $C_2-C_6$ alkyl group, preferably a $C_2$ or $C_3$ alkyl group.

The hydrocarbyl/hydrocarbon/alkyl of $R^{1'}$ can be straight chain or branched and/or can be saturated or unsaturated.

In a highly preferred aspect $R^1$ is selected from —$SCH_3$, $OCH_3$, —$SCH_2CH_3$, —$OCH_2CH_3$, —F, and —Cl.

In a preferred aspect when Z is O, $R^{1'}$ is a $C_2-C_{10}$ alkyl group and when Z is S, $R^{1'}$ is a hydrocarbyl group or H Hydrocarbyl The term "hydrocarbyl group" as used herein means a group comprising at least C and H and can optionally comprise one or more other suitable substituents. Examples of such substituents can include halo, alkoxy, nitro, an alkyl group, a cyclic group etc. In addition to the possibility of the substituents being a cyclic group, a combination of substituents can form a cyclic group. If the hydrocarbyl group comprises more than one C then those carbons need not necessarily be linked to each other. For example, at least two of the carbons can be linked via a suitable element or group. Thus, the hydrocarbyl group can contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups can be linear, branched or cyclic, or an aryl group. The term hydrocarbon also includes those groups but wherein they have been optionally substituted. If the hydrocarbon is a branched structure having substituent(s) thereon, then the substitution can be on either the hydrocarbon backbone or on the branch; alternatively the substitutions can be on the hydrocarbon backbone and on the branch.

Hydrocarbylsulphanyl

When Z is S the group of the formula -$L^1$-Z-$R^{1'}$ can be referred to or is analogous to a hydrocarbylsulphanyl group.

The term "hydrocarbylsulphanyl" means a group that comprises at least hydrocarbyl group (as herein defined) and sulphur. That sulphur group can be optionally oxidised.

Oxyhydrocarbyl

When Z is O the group of the formula -$L^1$-Z-$R^{1'}$ can be referred to or is analogous to an oxyhydrocarbyl group.

The term "oxyhydrocarbyl" group as used herein means a group comprising at least C, H and O and can optionally comprise one or more other suitable substituents. Examples of such substituents can include halo-, alkoxy-, nitro-, an alkyl group, a cyclic group etc. In addition to the possibility of the substituents being a cyclic group, a combination of substituents can form a cyclic group. If the oxyhydrocarbyl group comprises more than one C then those carbons need not necessarily be linked to each other. For example, at least two of the carbons can be linked via a suitable element or group. Thus, the oxyhydrocarbyl group can contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups can be linear, branched or cyclic, or an oxyaryl group. The term oxyhydrocarbon also includes those groups but wherein they have been optionally substituted. If the oxyhydrocarbon is a branched structure having substituent(s) thereon, then the substitution can be on either the hydrocarbon backbone or on the branch; alternatively the substitutions can be on the hydrocarbon backbone and on the branch.

Other Substituents

The compound of the present invention can have substituents other than $R^1$. By way of example, these other substituents can be one or more of: one or more halo groups, one or more 0 groups, one or more hydroxy groups, one or more amino groups, one or more sulphur containing group(s), one or more hydrocarbyl group(s)—such as an oxyhydrocarbyl group.

Superoxide Dismutase Assay

Protocol 1

SOD activity was measured using a spectrophotometric assay (Ukeda 1997). In this reaction, 3'-{1-[(phenylamino)-carbonyl]-3,4-tetrazolium}-bis(4-methoxy-6-nitro)benzene-sulfonic acid hydrate (XTT) is converted to a colourimetric product by the action of superoxide ions (produced by xanthine oxidase (XO) and xanthine). Production of superoxide ions is inhibited by SOD resulting in decreased product. The ability of test compounds to inhibit SOD is measured by their ability to restore production of the coloured product. Reactions were performed in a total volume of 0.1 ml of buffer A (42 mM $Na_2CO_3$ (pH 9.4), 0.1 mM xanthine (Sigma), 0.1 mM EDTA, 0.026 mM XTT (Sigma)).

The reaction was initiated by addition of 3.3 µl of xanthine oxidase (Sigma, 64 mU/ml) and the amount of CuZn-SOD (Sigma) added was titrated to give 80-90% inhibition of XO activity. The reaction was incubated at 24° C. for 30 minutes and products determined by measuring absorobance at 470 nm. All determinations were made in duplicate/triplicate.

Biotechnological Assays for Determining Sod Activity

Protocol 2

The ability of compounds to inhibit superoxide dismutase activity can also be assessed using amino acid sequences or nucleotide sequences encoding SOD, or active fragments, derivatives, homologues or variants thereof in, for example, high-through put screens.

Any one or more of appropriate targets—such as an amino acid sequence and/or nucleotide sequence—can be used for identifying an agent capable of modulating SOD in any of a variety of drug screening techniques. The target employed in such a test can be free in solution, affixed to a solid support, borne on a cell surface, or located intracellularly. The abolition of target activity or the formation of binding complexes between the target and the agent being tested can be measured.

The assay of the present invention can be a screen, whereby a number of agents are tested. In one aspect, the assay method of the present invention is a high through put screen.

Techniques for drug screening can be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

In one preferred aspect, the present invention relates to a method of identifying agents that selectively modulate SOD, which compounds have the formula (Ia).

The Following Paragraphs Relate to Compounds of Formulas XI Through XIV:

Steroid Sulphatase

Steroid sulphatase—which is sometimes referred to as steroid sulfatase or steryl sulphatase or "STS" for short—hydrolyses several sulphated steroids, such as oestrone sulphate, dehydroepiandrosterone sulphate and cholesterol sulphate. STS has been allocated the enzyme number EC 3.1.6.2.

STS has been cloned and expressed. For example see Stein et al (J. Biol. Chem. 264:13865-13872 (1989)) and Yen et al (Cell 49:443-454(1987)).

STS is an enzyme that has been implicated in a number of disease conditions.

By way of example, workers have found that a total deficiency in STS produces ichthyosis. According to some workers, STS deficiency is fairly prevalent in Japan. The same workers (Sakura et al, J Inherit Metab Dis 1997 November; 20(6):807-10) have also reported that allergic diseases—such as bronchial asthma, allergic rhinitis, or atopic dermatitis—can be associated with a steroid sulphatase deficiency.

In addition to disease states being brought on through a total lack of STS activity, an increased level of STS activity can also bring about disease conditions. By way of example, and as indicated above, there is strong evidence to support a role of STS in breast cancer growth and metastasis.

STS has also been implicated in other disease conditions. By way of example, Le Roy et al (Behav Genet 1999 March; 29(2):131-6) have determined that there can be a genetic correlation between steroid sulphatase concentration and initiation of attack behaviour in mice. The authors conclude that sulphatation of steroids can be the prime mover of a complex network, including genes shown to be implicated in aggression by mutagenesis.

STS Inhibition

It is believed that some disease conditions associated with STS activity are due to conversion of a nonactive, sulphated oestrone to an active, nonsulphated oestrone. In disease conditions associated with STS activity, it would be desirable to inhibit STS activity.

Here, the term "inhibit" includes reduce and/or eliminate and/or mask and/or prevent the detrimental action of STS.

STS Inhibitor

In accordance with the present invention, the compound of the present invention is capable of acting as an STS inhibitor.

Here, the term "inhibitor" as used herein with respect to the compound of the present invention means a compound that can inhibit STS activity—such as reduce and/or eliminate and/or mask and/or prevent the detrimental action of STS. The STS inhibitor can act as an antagonist.

The ability of compounds to inhibit oestrone sulphatase activity can be assessed using either intact MCF-7 breast cancer cells or placental microsomes. In addition, an animal model can be used. Details on suitable Assay Protocols are presented in following sections. It is to be noted that other assays could be used to determine STS activity and thus STS inhibition. For example, reference can also be made to the teachings of WO-A-99/50453.

Preferably, for some applications, the compound is further characterised by the feature that if the sulphamate group were to be substituted by a sulphate group to form a sulphate derivative, then the sulphate derivative would be hydrolysable by an enzyme having steroid sulphatase (E.C. 3.1.6.2) activity—i.e. when incubated with steroid sulphatase EC 3.1.6.2 at pH 7.4 and 37° C.

In one preferred embodiment, if the sulphamate group of the compound were to be replaced with a sulphate group to form a sulphate compound then that sulphate compound would be hydrolysable by an enzyme having steroid sulphatase (E.C. 3.1.6.2) activity and would yield a Km value of less than 200 mmolar, preferably less than 150 mmolar, preferably less than 100 mmolar, preferably less than 75 mmolar, preferably less than 50 mmolar, when incubated with steroid sulphatase EC 3.1.6.2 at pH 7.4 and 37° C.

In a preferred embodiment, the compound of the present invention is not hydrolysable by an enzyme having steroid sulphatase (E.C. 3.1.6.2) activity.

For some applications, preferably the compound of the present invention has at least about a 100 fold selectivity to a desired target (e.g. STS), preferably at least about a 150 fold selectivity to the desired target, preferably at least about a 200 fold selectivity to the desired target, preferably at least about a 250 fold selectivity to the desired target, preferably at least about a 300 fold selectivity to the desired target, preferably at least about a 350 fold selectivity to the desired target.

It is to be noted that the compound of the present invention can have other beneficial properties in addition to or in the alternative to its ability to inhibit STS activity.

Groups $R^1$ and $R^2$

As discussed above $R^1$ is an optional group of the formula -$L^1$-S-$R^{1'}$, and $R^2$ is an optional group of the formula -$L^2$-S-$R^{2'}$. $L^1$ is an optional linker group. $R^{1'}$ is a hydrocarbyl group. $L^2$ is an optional linker group. $R^{2'}$ is a hydrocarbyl group.

Independently either of linker groups $L^1$ and $L^2$ can or can not be present. If present $L^1$ or $L^2$ can be a hydrocarbyl group.

Preferably $L^1$ and $L^2$ are independently selcted from $C_1$-$C_{10}$ hydrocarbyl, $C_1$-$C_5$ hydrocarbyl or $C_1$-$C_3$ hydrocarbyl.

Preferably $L^1$ and $L^2$ are independently selcted from hydrocarbon groups, preferably $C_1$-$C_{10}$ hydrocarbon, $C_1$-$C_5$ hydrocarbon or $C_1$-$C_3$ hydrocarbon.

Preferably $L^1$ and $L^2$ are independently selcted from alkyl groups, $C_1$-$C_{10}$ alkyl, $C_1$-$C_5$ alkyl or $C_1$-$C_3$ alkyl.

The hydrocabyl/hydrocarbon/alkyl of $L^1$ and $L^2$ can be straight chain or branched and/or can be saturated or unsaturated.

In one aspect $L^1$ and/or $L^2$ can contain a terminal sulphur moiety. In this aspect $L^1$ and/or $L^2$ are linked to the remainder of $R^1$ or $R^2$, respectively, by a sulphide bond and $R^1$ or $R^2$ as a whole contains a disulphide bond.

For the avoidance of doubt, S represents sulphur.

$R^{1'}$ or $R^{2'}$ are independently of each other a hydrocarbyl group.

Preferably $R1'$ and $R^{2'}$ are independently selcted from $C_1$-$C_{10}$ hydrocarbyl, $C_1$-$C_5$ hydrocarbyl or $C_1$-$C_3$ hydrocarbyl.

Preferably $R^{1'}$ and $R^{2'}$ are independently selcted from hydrocarbon groups, $C_1$-$C_{10}$ hydrocarbon, $C_1$-$C_5$ hydrocarbon or $C_1$-$C_3$ hydrocarbon.

Preferably $R^{1'}$ and $R^{2'}$ are independently selcted from alkyl groups, $C_1$-$C_{10}$ alkyl, $C_1$-$C_5$ alkyl or $C_1$-$C_3$ alkyl.

The hydrocabyl/hydrocarbon/alkyl of $R^{1'}$ and $R^{2'}$ can be straight chain or branched and/or can be saturated or unsaturated.

In a highly preferred asepct $R^{1'}$ and $R^{2'}$ are independently selected from methly (—$CH_3$) and ethyl (—$CH_3CH_3$).

Group K

Group K need not be a cyclic structure. In this regard, group K can be a linear structure that can have the ability to conform to a ring like structure when in in vivo.

In a preferred aspect, group K is cyclic—so as to form the cyclic group K.

Cyclic group K need not necessarily be fused to ring X. In this regard, they can be separated by a suitable spacer group—which can be a hydrocarbyl group.

In a preferred aspect, cyclic group K is fused to ring X.

Group K can be a polycyclic group, which need not be a fused polycycle.

Thus, in a preferred aspect, group K and ring X make up a polycyclic compound. As indicated, here the term "polycyclic" includes fused and non-fused ring structures including combinations thereof.

At least one of the cyclic groups K and X can be a heterocyclic group (a heterocycle) or a non-heterocyclic group.

At least one of the cyclic groups K and X can be a saturated ring structure or an unsaturated ring structure (such as an aryl group).

Preferably, at least one of the cyclic groups is an aryl ring.

If the cyclic group is polycyclic some or all of the ring components of the compound can be fused together or joined via one or more suitable spacer groups.

The polycyclic compound can comprise a number of fused rings. In this aspect the fused rings can comprise any combination of different size rings, such as 3 six-membered rings (6,6,6), a six-membered ring, a seven-membered ring and a six-membered ring (6,7,6), a six-membered ring and two eight-membered rings (6,8,8) etc.

In one aspect the present invention relates to compounds wherein the polycyclic compounds are other than (6,6,7) rings. In a further aspect, the present invention relates to compounds wherein the polycyclic compounds only contain rings having other than 7 members.

Preferably the polycyclic compound will contain, inclusive of all substituents, no more than 50 about carbon atoms, more usually no more than about 30 to 40 carbon atoms.

The polycyclic compound can comprise at least two ring components, or at least three ring components, or at least four ring components.

Preferably, the polycyclic compound comprises four ring components.

Preferred polycyclic compounds have a steroidal ring component, or bio-isosteres thereof.

Hydrocarbyl

The term "hydrocarbyl group" as used herein means a group comprising at least C and H and can optionally comprise one or more other suitable substituents. Examples of such substituents can include halo, alkoxy, nitro, an alkyl group, a cyclic group etc. In addition to the possibility of the substituents being a cyclic group, a combination of substituents can form a cyclic group. If the hydrocarbyl group comprises more than one C then those carbons need not necessarily be linked to each other. For example, at least two of the carbons can be linked via a suitable element or group. Thus, the hydrocarbyl group can contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups can be linear, branched or cyclic, or an aryl group. The term hydrocarbon also includes those groups but wherein they have been optionally substituted. If the hydrocarbon is a branched structure having substituent(s) thereon, then the substitution can be on either the hydrocarbon backbone or on the branch; alternatively the substitutions can be on the hydrocarbon backbone and on the branch.

Sulphamate Group

In one embodiment, the ring X has a sulphamate group as a substituent. The term "sulphamate" as used herein includes an ester of sulphamic acid, or an ester of an N-substituted derivative of sulphamic acid, or a salt thereof.

If $R^3$ is a sulphamate group then the compound of the present invention is referred to as a sulphamate compound.

Typically, the sulphamate group has the formula:

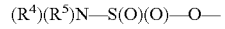

$(R^4)(R^5)N$—$S(O)(O)$—$O$— wherein preferably $R^4$ and $R^5$ are independently selected from H, alkyl, cycloalkyl, alkenyl and aryl, or combinations thereof, or together represent alkylene, wherein the or each alkyl or cycloalkyl or alkenyl or optionally contain one or more hetero atoms or groups.

When substituted, the N-substituted compounds of this invention can contain one or two N-alkyl, N-alkenyl, N-cycloalkyl or N-aryl substituents, preferably containing or each containing a maximum of 10 carbon atoms. When $R^4$ and/or $R^5$ is alkyl, the preferred values are those where $R^4$ and $R^5$ are each independently selected from lower alkyl groups containing from 1 to 6 carbon atoms, that is to say methyl, ethyl, propyl etc. $R^4$ and $R^5$ can both be methyl. When $R^4$ and/or $R^5$ is aryl, typical values are phenyl and tolyl ($PhCH_3$; o). Where $R^4$ and $R^5$ represent cycloalkyl, typical values are cyclopropyl, cyclopentyl, cyclohexyl etc. When joined together $R^4$ and $R^5$ typically represent an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphamate group can form a ring structure by being fused to (or associated with) one or more atoms in or on group X.

In some embodiments, there can be more than one sulphamate group. By way of example, there can be two sulphamates (i.e. bis-sulphamate compounds). If these compounds are based on a steroidal nucleus, preferably the second (or at least one of the additional) sulphamate group is located at position 17 of the steroidal nucleus. These groups need not be the same.

In some preferred embodiments, at least one of $R^4$ and $R^5$ is H.

In some further preferred embodiments, each of $R^4$ and $R^5$ is H.

Phosphonate Group

If $R^3$ is a phosphonate group then the compound of the present invention is referred to as a phosphonate compound.

Typically, the phosphonate group has the formula:

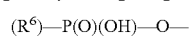

$(R^6)$—$P(O)(OH)$—$O$— wherein preferably $R^6$ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention can contain one or two N-alkyl, N-alkenyl, N-cycloalkyl or N-aryl substituents, preferably containing or each containing a maximum of 10 carbon atoms. When $R^6$ is alkyl, $R^6$ can be a lower alkyl groups containing from 1 to 6 carbon atoms, that is to say methyl, ethyl, propyl etc. By way of example, $R^6$ can be methyl. When $R^6$ is aryl, typical values are phenyl and tolyl (PhCH₃;o). Where R⁶ represents cycloalkyl, typical values are cyclopropyl, cyclopentyl, cyclohexyl etc. R⁶ can even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the phosphonate group can form a ring structure by being fused to (or associated with) one or more atoms in or on group X.

In some embodiments, there can be more than one phosphonate group. By way of example, there can be two phosphonates (i.e. bis-phosphonate compounds). If these compounds are based on a steroidal nucleus, preferably the second (or at least one of the additional) phosphonate group is located at position 17 of the steroidal nucleus. These groups need not be the same.

Thiophosphonate Group

If R³ is a thiophosphonate group then the compound of the present invention is referred to as a thiophosphonate compound.

Typically, the thiophosphonate group has the formula:

(R⁷)—P(S)(OH)—O— wherein preferably R⁷ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention can contain one or two N-alkyl, N-alkenyl, N-cycloalkyl or N-aryl substituents, preferably containing or each containing a maximum of 10 carbon atoms. When R⁷ is alkyl, R⁷ can be a lower alkyl groups containing from 1 to 6 carbon atoms, that is to say methyl, ethyl, propyl etc. By way of example, R⁷ can be methyl. When R⁷ is aryl, typical values are phenyl and tolyl (PhCH₃;o). Where R⁷ represents cycloalkyl, typical values are cyclopropyl, cyclopentyl, cyclohexyl etc. R⁷ can even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the thiophosphonate group can form a ring structure by being fused to (or associated with) one or more atoms in or on group X.

In some embodiments, there can be more than one thiophosphonate group. By way of example, there can be two thiophosphonates (i.e. bis-thiophosphonate compounds). If these compounds are based on a steroidal nucleus, preferably the second (or at least one of the additional) thiophosphonate group is located at position 17 of the steroidal nucleus. These groups need not be the same.

Sulphonate Group

If R³ is a sulphonate group then the compound of the present invention is referred to as a sulphonate compound.

Typically, the sulphonate group has the formula:

(R⁸)—S(O)(O)—O— wherein preferably R⁸ is H, alkyl, cycloalkyl, alkenyl or aryl, or combinations thereof, wherein the or each alkyl or cycloalkyl or alkenyl or optionally contain one or more hetero atoms or groups.

When substituted, the N-substituted compounds of this invention can contain one or two N-alkyl, N-alkenyl, N-cycloalkyl or N-aryl substituents, preferably containing or each containing a maximum of 10 carbon atoms. When R⁸ is alkyl, R⁸ can be a lower alkyl groups containing from 1 to 6 carbon atoms, that is to say methyl, ethyl, propyl etc. By way of example, R⁸ can be methyl. When R⁸ is aryl, typical values are phenyl and tolyl (PhCH₃;o). Where R⁸ represents cycloalkyl, typical values are cyclopropyl, cyclopentyl, cyclohexyl etc. R⁸ can even comprise an alkylene group providing a chain of 4 to 6 carbon atoms, optionally interrupted by one or more hetero atoms or groups, e.g. to provide a 5 membered heterocycle, e.g. morpholino, pyrrolidino or piperidino.

Within the values alkyl, cycloalkyl, alkenyl and aryl substituted groups are included containing as substituents therein one or more groups which do not interfere with the sulphatase inhibitory activity of the compound in question. Exemplary non-interfering substituents include hydroxy, amino, halo, alkoxy, alkyl and aryl.

In some embodiments, the sulphonate group can form a ring structure by being fused to (or associated with) one or more atoms in or on group X.

In some embodiments, there can be more than one sulphonate group. By way of example, there can be two sulphonates (i.e. bis-sulphonate compounds). If these compounds are based on a steroidal nucleus, preferably the second (or at least one of the additional) sulphonate group is located at position 17 of the steroidal nucleus. These groups need not be the same.

Combination of Sulphonate/Phosphonate/Thiophosphonate/Sulphamate

For some compounds of the present invention there can be present one of a sulphonate as herein defined or a phosphonate as herein defined or a thiophosphonate as herein defined or a sulphamate as herein defined; and another of a sulphonate as herein defined or a phosphonate as herein defined or a thiophosphonate as herein defined or a sulphamate as herein defined. By way of example, the compound of the present invention can comprise one sulphamate group and one phosphonate group.

If these compounds of the present invention are based on a steroidal nucleus, preferably the other of said groups is located at position 17 of the steroidal nucleus.

Mimic

In one aspect, X and K can be a mimic of a steroidal ring structure

The term "mimic" as used herein means having a similar or different structure but having a similar functional effect. In other words, group K and ring X together can be a bio-isostere of the rings of a steroid, or an active part thereof.

In a preferred aspect, group K and ring X together can be a bio-isostere of the rings of oestrone, or a part thereof.

Steroidal Ring Structure

In one preferred aspect, X and K make up a steroidal ring structure—that is to say a cyclopentanophenanthrene skeleton, or bio-isosteres thereof.

As it is well known in the art, a classical steroidal ring structure has the generic formula of:

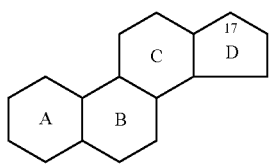

In the above formula, the rings have been labelled in the conventional manner.

An example of a bio-isostere is when any one or more of rings A, B, C and D is a heterocyclic ring and/or when any one or more of rings A, B, C and D has been substituted and/or when any one or more of rings A, B, C and D has been modified; but wherein the bio-isostere in the absence of the sulphamate group has steroidal properties.

In this regard, the structure of a preferred polycyclic structure can be presented as:

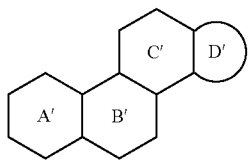

wherein each ring A', B', C' and D' independently represents a heterocyclic ring or a non-heterocyclic ring, which rings can be independently substituted or unsubstituted, saturated or unsaturated.

By way of example, any one or more of rings A', B', C' and D' can be independently substituted with suitable groups—such as an alkyl group, an aryl group, a hydroxy group, a halo group, a hydrocarbyl group, an oxyhydrocarbyl group etc.

An example of D' is a five or six membered non-heterocyclic ring having at least one substituent.

In one preferred embodiment, the ring D' is substituted with a ethinyl group.

If any one of rings A', B', C' and D' is a heterocyclic ring, then preferably that heterocyclic ring comprises a combination of C atoms and at least one N atom and/or at least one O atom. Other heterocyclic atoms can be present in the ring.

Examples of suitable, preferred steroidal nuclei rings A'-D' of the compounds of the present invention include rings A-D of dehydroepiandrosterone and oestrogens including oestrone.

Preferred steroidal nuclei rings A'-D' of the compounds of the present invention include rings A-D of:

Oestrones and Substituted Oestrones, viz:
oestrone
2-OH-oestrone
4-OH-oestrone
6α-OH-oestrone
7α-OH-oestrone
16α-OH-oestrone
16β-OH-oestrone
2-MeO-oestrone
17-deoxyoestrone Oestradiols and Substituted Oestradiols, viz:
4-OH-17β-oestradiol
6α-OH-17β-oestradiol
7α-OH-17β-oestradiol
4-OH-17α-oestradiol
6α-OH-17α-oestradiol
7α-OH-17α-oestradiol
16α-OH-17α-oestradiol
16α-OH-17β-oestradiol
16β-OH-17α-oestradiol
16β-OH-17β-oestradiol
17α-oestradiol
17β-oestradiol
17α-ethinyl-17β-oestradiol
17β-ethinyl-17α-oestradiol
17-deoxyoestradiol Oestriols and Substituted Oestriols, viz:
oestriol
4-OH-oestriol
6α-OH-oestriol
7α-OH-oestriol
17-deoxyoestriol Dehydroepiandrosterones and Substituted Dehydroepiandrosterones, viz:
dehydroepiandrosterones
6α-OH-dehydroepiandrosterone
7α-OH-dehydroepiandrosterone
16α-OH-dehydroepiandrosterone
16-OH-dehydroepiandrosterone
androstenediol In general terms the ring system A'B'C'D' can contain a variety of non-interfering substituents. In particular, the ring system A'B'C'D' can contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

Non-Steroid Structures

In an alternative embodiment, the compound of the present invention can not contain or be based on a steroid nucleus. In this regard, the polycyclic compound can contain or be based on a non-steroidal ring system—such as diethylstilboestrol, stilboestrol, coumarins, flavonoids, combrestatin and other ring systems. Other suitable non-steroidal compounds for use in or as the composition of the present invention can be found in U.S. Pat. No. 5,567,831.

Other Substituents

The compound of the present invention can have substituents other than $R^1$, $R^2$ and $R^3$. By way of example, these other substituents can be one or more of: one or more sulphamate group(s), one or more phosphonate group(s), one or more thiophosphonate group(s), one or more sulphonate group(s), one or more sulphonamide group(s), one or more halo groups, one or more O groups, one or more hydroxy groups, one or more amino groups, one or more sulphur containing group(s), one or more hydrocarbyl group(s)—such as an oxyhydrocarbyl group.

Oxyhydrocarbyl

The term "oxyhydrocarbyl" group as used herein means a group comprising at least C, H and O and can optionally comprise one or more other suitable substituents. Examples of such substituents can include halo-, alkoxy-, nitro-, an alkyl group, a cyclic group etc. In addition to the possibility of the substituents being a cyclic group, a combination of substituents can form a cyclic group. If the oxyhydrocarbyl group comprises more than one C then those carbons need not necessarily be linked to each other. For example, at least two of the carbons can be linked via a suitable element or group. Thus, the oxyhydrocarbyl group can contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups can be linear, branched or cyclic, or an oxyaryl group. The term oxyhydrocarbon also includes those groups but wherein they have been optionally substituted. If the oxyhydrocarbon is a branched structure having substituent(s) thereon, then the substitution can be on either the hydrocarbon backbone or on the branch; alternatively the substitutions can be on the hydrocarbon backbone and on the branch.

Typically, the oxyhydrocarbyl group is of the formula $C_{1-6}O$ (such as a $C_{1-3}O$).

Assay for Determining STS Activity Using Cancer Cells

Protocol 3

Inhibition of Steroid Sulphatase Activity in MCF-7 Cells

Steroid sulphatase activity is measured in vitro using intact MCF-7 human breast cancer cells. This hormone dependent cell line is widely used to study the control of human breast cancer cell growth. It possesses significant steroid sulphatase activity (MacIndoe et al. Endocrinology, 123, 1281-1287 (1988); Purohit & Reed, Int. J. Cancer, 50, 901-905 (1992)) and is available in the U.S.A. from the American Type Culture Collection (ATCC) and in the U.K. (e.g. from The Imperial Cancer Research Fund).

Cells are maintained in Minimal Essential Medium (MEM) (Flow Laboratories, Irvine, Scotland) containing 20 mM HEPES, 5% foetal bovine serum, 2 mM glutamine, nonessential amino acids and 0.075% sodium bicarbonate. Up to 30 replicate 25 cm2 tissue culture flasks are seeded with approximately $1 \times 10^5$ cells/flask using the above medium. Cells are grown to 80% confluency and the medium is changed every third day.

Intact monolayers of MCF-7 cells in triplicate 25 cm$^2$ tissue culture flasks are washed with Earle's Balanced Salt Solution (EBSS from ICN Flow, High Wycombe, U.K.) and incubated for 3-4 hours at 37° C. with 5 pmol ($7 \times 10^5$ dpm) [6,7-3H]oestrone-3-sulphate (specific activity 60 Ci/mmol from New England Nuclear, Boston, Mass., U.S.A.) in serum-free MEM (2.5 ml) together with oestrone-3-sulphamate (11 concentrations: 0; 1 fM; 0.01 pM; 0.1 pM; 1 pM; 0.01 nM; 0.1 nM; 1 nM; 0.01 mM; 0.1 mM; 1 mM). After incubation each flask is cooled and the medium (1 ml) is pipetted into separate tubes containing [14C]oestrone ($7 \times 103$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase is removed, evaporated and the 3H and 14C content of the residue determined by scintillation spectrometry. The mass of oestrone-3-sulphate hydrolysed was calculated from the 3H counts obtained (corrected for the volumes of the medium and organic phase used, and for recovery of [14C] oestrone added) and the specific activity of the substrate. Each batch of experiments includes incubations of microsomes prepared from a sulphatase-positive human placenta (positive control) and flasks without cells (to assess apparent non-enzymatic hydrolysis of the substrate). The number of cell nuclei per flask is determined using a Coulter Counter after treating the cell monolayers with Zaponin. One flask in each batch is used to assess cell membrane status and viability using the Trypan Blue exclusion method (Phillips, H.J. (1973) In: Tissue culture and applications, [eds: Kruse, D. F. & Patterson, M. K.]; pp. 406-408; Academic Press, New York).

Results for steroid sulphatase activity are expressed as the mean±1 S.D. of the total product (oestrone+oestradiol) formed during the incubation period (20 hours) calculated for 106 cells and, for values showing statistical significance, as a percentage reduction (inhibition) over incubations containing no oestrone-3-sulphamate. Unpaired Student's t-test was used to test the statistical significance of results.

Assay for Determining STS Activity Using Placental Microsomes

Protocol 4

Inhibition of Steroid Sulphatase Activity in Placental Microsomes

Sulphatase-positive human placenta from normal term pregnancies are thoroughly minced with scissors and washed once with cold phosphate buffer (pH 7.4, 50 mM) then resuspended in cold phosphate buffer (5 ml/g tissue). Homogenisation is accomplished with an Ultra-Turrax homogeniser, using three 10 second bursts separated by 2 minute cooling periods in ice. Nuclei and cell debris are removed by centrifuging (4° C.) at 2000 g for 30 minutes and portions (2 ml) of the supernatant are stored at 20° C. The protein concentration of the supernatants is determined by the method of Bradford (Anal. Biochem., 72, 248-254 (1976)).

Incubations (1 ml) are carried out using a protein concentration of 100 mg/ml, substrate concentration of 20 mM [6,7-3H]oestrone-3-sulphate (specific activity 60 Ci/mmol from New England Nuclear, Boston, Mass., U.S.A.) and an incubation time of 20 minutes at 37° C. If necessary eight concentrations of compounds are employed: 0 (i.e. control); 0.05 mM; 0.1 mM; 0.2 mM; 0.4 mM; 0.6 mM; 0.8 mM; 1.0 mM. After incubation each sample is cooled and the medium (1 ml) was pipetted into separate tubes containing [14C] oestrone ($7 \times 10^3$ dpm) (specific activity 97 Ci/mmol from Amersham International Radiochemical Centre, Amersham, U.K.). The mixture is shaken thoroughly for 30 seconds with toluene (5 ml). Experiments have shown that >90% [14C] oestrone and <0.1% [3H]oestrone-3-sulphate is removed from the aqueous phase by this treatment. A portion (2 ml) of the organic phase was removed, evaporated and the 3H and 14C content of the residue determined by scintillation spectrometry. The mass of oestrone-3-sulphate hydrolysed is calculated from the 3H counts obtained (corrected for the volumes of the medium and organic phase used, and for recovery of [14C]oestrone added) and the specific activity of the substrate.

Animal Assay Model for Determining STS Activity

Protocol 5

Inhibition of Oestrone Sulphatase Activity In Vivo

The compounds of the present invention can be studied using an animal model, in particular in ovariectomised rats. In this model compounds which are oestrogenic stimulate uterine growth.

The compound (0.1 mg/Kg/day for five days) is administered orally to rats with another group of animals receiving vehicle only (propylene glycol). At the end of the study samples of liver tissue were obtained and oestrone sulphatase activity assayed using 3H oestrone sulphate as the substrate as previously described (see PCT/GB95/02638).

Animal Assay Model for Determining Oestrogenic Activity

Protocol 6

Lack of In Vivo Oestrogenicity

The compounds of the present invention can be studied using an animal model, in particular in ovariectomised rats. In this model, compounds which are oestrogenic stimulate uterine growth.

The compound (0.1 mg/Kg/day for five days) was administered orally to rats with another group of animals receiving vehicle only (propylene glycol). At the end of the study uteri were obtained and weighed with the results being expressed as uterine weight/whole body weight×100.

Compounds having no significant effect on uterine growth are not oestrogenic.

Biotechnological Assays for Determining STS Activity

Protocol 7

The ability of compounds to inhibit oestrone sulphatase activity can also be assessed using amino acid sequences or nucleotide sequences encoding STS, or active fragments, derivatives, homologues or variants thereof in, for example, high-through put screens.

Any one or more of appropriate targets—such as an amino acid sequence and/or nucleotide sequence—can be used for identifying an agent capable of modulating STS in any of a variety of drug screening techniques. The target employed in such a test can be free in solution, affixed to a solid support, borne on a cell surface, or located intracellularly. The abolition of target activity or the formation of binding complexes between the target and the agent being tested can be measured.

The assay of the present invention can be a screen, whereby a number of agents are tested. In one aspect, the assay method of the present invention is a high through put screen.

Techniques for drug screening can be based on the method described in Geysen, European Patent Application 84/03564, published on Sep. 13, 1984. In summary, large numbers of different small peptide test compounds are synthesised on a solid substrate, such as plastic pins or some other surface. The peptide test compounds are reacted with a suitable target or fragment thereof and washed. Bound entities are then detected—such as by appropriately adapting methods well known in the art. A purified target can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a target specifically compete with a test compound for binding to a target.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

In one preferred aspect, the present invention relates to a method of identifying agents that selectively modulate STS, which compounds have the formula (Ia).

The Following Paragraphs Relate to all Compounds of the Present Invention:

Reporters

A wide variety of reporters can be used in the assay methods (as well as screens) of the present invention with preferred reporters providing conveniently detectable signals (e.g. by spectroscopy). By way of example, a reporter gene can encode an enzyme which catalyses a reaction which alters light absorption properties.

Other protocols include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes can even be used. These and other assays are described, among other places, in Hampton R et al (1990, Serological Methods, A Laboratory Manual, APS Press, St Paul Minn.) and Maddox D E et al (1983, J Exp Med 158:1211).

Examples of reporter molecules include but are not limited to (β-galactosidase, invertase, green fluorescent protein, luciferase, chloramphenicol, acetyltransferase, (-glucuronidase, exo-glucanase and glucoamylase. Alternatively, radiolabelled or fluorescent tag-labelled nucleotides can be incorporated into nascent transcripts which are then identified when bound to oligonucleotide probes.

By way of further examples, a number of companies such as Pharmacia Biotech (Piscataway, N.J.), Promega (Madison, Wis.), and US Biochemical Corp (Cleveland, Ohio) supply commercial kits and protocols for assay procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Host Cells

The term "host cell"—in relation to the present invention includes any cell that could comprise the target for the agent of the present invention.

Thus, a further embodiment of the present invention provides host cells transformed or transfected with a polynucleotide that is or expresses the target of the present invention. Preferably said polynucleotide is carried in a vector for the replication and expression of polynucleotides that are to be the target or are to express the target. The cells will be chosen to be compatible with the said vector and can for example be prokaryotic (for example bacterial), fungal, yeast or plant cells.

The gram negative bacterium E. coli is widely used as a host for heterologous gene expression. However, large amounts of heterologous protein tend to accumulate inside the cell. Subsequent purification of the desired protein from the bulk of E. coli intracellular proteins can sometimes be difficult.

In contrast to E. coli, bacteria from the genus Bacillus are very suitable as heterologous hosts because of their capability to secrete proteins into the culture medium. Other bacteria suitable as hosts are those from the genera Streptomyces and Pseudomonas.

Depending on the nature of the polynucleotide encoding the polypeptide of the present invention, and/or the desirability for further processing of the expressed protein, eukaryotic hosts such as yeasts or other fungi can be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

Examples of suitable expression hosts within the scope of the present invention are fungi such as Aspergillus species (such as those described in EP-A-0184438 and EP-A-0284603) and Trichoderma species; bacteria such as Bacillus species (such as those described in EP-A-0134048 and EP-A-0253455), Streptomyces species and Pseudomonas species; and yeasts such as Kluyveromyces species (such as those described in EP-A-0096430 and EP-A-0301670) and Saccharomyces species. By way of example, typical expression hosts can be selected from *Aspergillus niger, Aspergillus niger* var. *tubigenis, Aspergillus niger* var. *awamori, Aspergillus aculeatis, Aspergillus nidulans, Aspergillus oryzae, Trichoderma reesei, Bacillus subtilis, Bacillus licheniformis, Bacillus amyloliquefaciens, Kluyveromyces lactis* and *Saccharomyces cerevisiae*.

The use of suitable host cells—such as yeast, fungal and plant host cells—can provide for post-translational modifications (e.g. myristoylation, glycosylation, truncation, lapidation and tyrosine, serine or threonine phosphorylation) as can be needed to confer optimal biological activity on recombinant expression products of the present invention.

Organism

The term "organism" in relation to the present invention includes any organism that could comprise the target according to the present invention and/or products obtained therefrom. Examples of organisms can include a fungus, yeast or a plant.

The term "transgenic organism" in relation to the present invention includes any organism that comprises the target according to the present invention and/or products obtained.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press) and Ausubel et al., Current Protocols in Molecular Biology (1995), John Wiley & Sons, Inc.

If a prokaryotic host is used then the nucleotide sequence can need to be suitably modified before transformation—such as by removal of introns.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401-429, Allen and Unwin, London) and by King et al (1989, Molecular and Cell Biology of Yeasts, E F Walton and G T Yarronton, eds, pp 107-133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163-168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material. Several techniques exist for inserting the genetic information, the two main principles being direct introduction of the genetic information and introduction of the genetic information by use of a vector system. A review of the general techniques can be found in articles by Potrykus (Annu Rev Plant Physiol Plant Mol Biol [1991] 42:205-225) and Christou (Agro-Food-Industry Hi-Tech March/April 1994 17-27). Further teachings on plant transformation can be found in EP-A-0449375.

Thus, the present invention also provides a method of transforming a host cell with a nucleotide sequence that is to be the target or is to express the target. Host cells transformed with the nucleotide sequence can be cultured under conditions suitable for the expression of the encoded protein. The protein produced by a recombinant cell can be displayed on the surface of the cell. If desired, and as will be understood by those of skill in the art, expression vectors containing coding sequences can be designed with signal sequences which direct secretion of the coding sequences through a particular prokaryotic or eukaryotic cell membrane. Other recombinant constructions can join the coding sequence to nucleotide sequence encoding a polypeptide domain which will facilitate purification of soluble proteins (Kroll D J et al (1993) DNA Cell Biol 12:441-53).

Variants/Homologues/Derivatives

In addition to the specific amino acid sequences and nucleotide sequences mentioned herein, the present invention also encompasses the use of variants, homologue and derivatives thereof. Here, the term "homology" can be equated with "identity".

In the present context, an homologous sequence is taken to include an amino acid sequence which can be at least 75, 85 or 90% identical, preferably at least 95 or 98% identical. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology can be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program.

A further useful reference is that found in FEMS Microbiol Lett 1999 Can 15;174(2):247-50 (and a published erratum appears in FEMS Microbiol Lett Aug. 1, 1999;177 (1):187-8).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences can also have deletions, insertions or substitutions of amino acid residues which produce a silent change and result in a functionally equivalent substance. Deliberate amino acid substitutions can be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions can be made, for example according to the Table below. Amino acids in the same block in the second column and preferably in the same line in the third column can be substituted for each other:

| ALIPHATIC | Non-polar | G A P |
| | | I L V |
| | Polar—uncharged | C S T M |
| | | N Q |
| | Polar—charged | D E |
| | | K R |
| AROMATIC | | H F W Y |

Expression Vectors

The nucleotide sequence for use as the target or for expressing the target can be incorporated into a recombinant replicable vector. The vector can be used to replicate and express the nucleotide sequence in and/or from a compatible host cell. Expression can be controlled using control sequences which include promoters/enhancers and other expression regulation signals. Prokaryotic promoters and promoters functional in eukaryotic cells can be used. Tissue specific or stimuli specific promoters can be used. Chimeric promoters can also be used comprising sequence elements from two or more different promoters described above.

The protein produced by a host recombinant cell by expression of the nucleotide sequence can be secreted or can be contained intracellularly depending on the sequence and/or the vector used. The coding sequences can be designed with signal sequences which direct secretion of the substance coding sequences through a particular prokaryotic or eukaryotic cell membrane.

Fusion Proteins

The target amino acid sequence can be produced as a fusion protein, for example to aid in extraction and purification. Examples of fusion protein partners include glutathione-S-transferase (GST), 6×His, GAL4 (DNA binding and/or transcriptional activation domains) and (-galactosidase. It can also be convenient to include a proteolytic cleavage site between the fusion protein partner and the protein sequence of interest to allow removal of fusion protein sequences. Preferably the fusion protein will not hinder the activity of the target.

The fusion protein can comprise an antigen or an antigenic determinant fused to the substance of the present invention. In this embodiment, the fusion protein can be a non-naturally occurring fusion protein comprising a substance which can act as an adjuvant in the sense of providing a generalised stimulation of the immune system. The antigen or antigenic determinant can be attached to either the amino or carboxy terminus of the substance.

In another embodiment of the invention, the amino acid sequence can be ligated to a heterologous sequence to encode a fusion protein. For example, for screening of peptide libraries for agents capable of affecting the substance activity, it can be useful to encode a chimeric substance expressing a heterologous epitope that is recognised by a commercially available antibody.

Therapy

The compounds of the present invention can be used as therapeutic agents—i.e. in therapy applications.

The term "therapy" includes curative effects, alleviation effects, and prophylactic effects.

The therapy can be on humans or animals, preferably female animals.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions can be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions can comprise as—or in addition to—the carrier, excipient or diluent any suitable binder(s), lubricant(s), suspending agent(s), coating agent(s), solubilising agent(s).

Preservatives, stabilisers, dyes and even flavouring agents can be provided in the pharmaceutical composition. Examples of preservatives include sodium benzoate, sorbic acid and esters of p-hydroxybenzoic acid. Antioxidants and suspending agents can be also used.

There can be different composition/formulation requirements dependent on the different delivery systems. By way of example, the pharmaceutical composition of the present invention can be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation can be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions can be best used in the form of a sterile aqueous solution which can contain other substances, for example enough salts or monosaccharides to make the solution isotonic with blood. For buccal or sublingual administration the compositions can be administered in the form of tablets or lozenges which can be formulated in a conventional manner.

Combination Pharmaceutical

The compound of the present invention can be used in combination with one or more other active agents, such as one or more other pharmaceutically active agents.

By way of example, the compounds of the present invention can be used in combination with other SOD inhibitors and/or free radical producing agents and/or other inhibitors such as an aromatase inhibitor (such as for example, 4-hydroxyandrostenedione (4-OHA)) and/or steroids—such as the naturally occurring neurosteroids dehydroepiandrosterone sulphate (DHEAS) and pregnenolone sulphate (PS) and/or other structurally similar organic compounds.

In addition, or in the alternative, the compound of the present invention can be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)—such as TNF-α; Interferon alpha, beta and gamma; TGF-β. For some applications, preferably the cytokine is tumour necrosis factor (TNF). For some applications, the TNF can be any type of TNF—such as TNF-α, TNF-β, including derivatives or mixtures thereof. More preferably the cytokine is TNF-α. Teachings on TNF can be found in the art—such as WO-A-98/08870 and WO-A-98/13348.

Combination Therapies

The inhibitors of the present invention can also be combined with other therapies.

For example the compound can be administered in combination with radiotherapy. Radiotherapy is believed to work by generating reactive oxygen. Combination of the present compounds with radiotherapy will provide improved results, particularly in tumours resistant to radiotherapy alone.

Other Aspects

The present invention can be used in other non-medicinal applications. For example the present compound mat be utilised as an anti-microbial. Macrophages use reactive oxygen to kill micro-organisms. Some micro-organisms express a SOD enzyme. The SOD is often required for pathogenicity. Thus by provision of a SOD inhibiting compound the present invention can provide more effective macrophage action.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention can be administered by direct injection. The composition can be formulated for parenteral, rectal, vaginal, mucosal, intramuscular, intravenous, subcutaneous, intraocular or transdermal administration. Depending upon the need, the agent can be administered at a dose of from 0.01 to 30 mg/kg body weight, such as from 0.1 to 10 mg/kg, more preferably from 0.1 to 1 mg/kg body weight.

By way of further example, the agents of the present invention can be administered in accordance with a regimen of 1 to 4 times per day, preferably once or twice per day. The specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the SOD inhibitors of the present invention can be formulated in any suitable manner utilising conventional pharmaceutical formulating techniques and pharmaceutical carriers, adjuvants, excipients, diluents etc. and usually for parenteral administration. Approximate effective dose rates can be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They can be given in single dose regimes, split dose regimes and/or in multiple dose regimes lasting over several days. For oral administration they can be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention can be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_0$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2×of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles.

Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves.

Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling can result in cancer. Reduced cell cycling can result in degenerative conditions. Use of the compound of the present invention can provide a means to treat such disorders and conditions.

Thus, the compound of the present invention can be suitable for use in the treatment of cell cycling disorders such as cancers, including hormone dependent and hormone independent cancers.

In addition, the compound of the present invention can be suitable for the treatment of cancers such as breast cancer, ovarian cancer, endometrial cancer, sarcomas, melanomas, prostate cancer, pancreatic cancer etc. and other solid tumours.

For some applications, cell cycling is inhibited and/or prevented and/or arrested, preferably wherein cell cycling is prevented and/or arrested. In one aspect cell cycling can be inhibited and/or prevented and/or arrested in the $G_2/M$ phase. In one aspect cell cycling can be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol than control cells. Details on this protocol are presented below.

Thus, the present invention provides compounds which: cause inhibition of growth of oestrogen receptor positive (ER+) and ER negative (ER−) breast cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 8

Procedure

Stage 1

MCF-7 breast cancer cells are seeded into multi-well culture plates at a density of 105 cells/well. Cells were allowed to attach and grown until about 30% confluent when they are treated as follows:

Control—no treatment

Compound of Interest (COI) 20 µM

Cells are grown for 6 days in growth medium containing the COI with changes of medium/CO every 3 days. At the end of this period cell numbers were counted using a Coulter cell counter.

Stage 2

After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.

Cancer

As indicated, the compounds of the present invention can be useful in the treatment of cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

It is known that oestrogens undergo a number of hydroxylation and conjugation reactions after their synthesis. Until recently it was thought that such reactions were part of a metabolic process that ultimately rendered oestrogens water soluble and enhanced their elimination from the body. It is now evident that some hydroxy metabolites (e.g. 2-hydroxy and 16alpha-hydroxy) and conjugates (e.g. oestrone sulphate, E1S) are important in determining some of the complex actions that oestrogens have in the body.

Workers have investigated the formation of 2- and 16-hydroxylated oestrogens in relation to conditions that alter the risk of breast cancer. There is now evidence that factors which increase 2-hydroxylase activity are associated with a reduced cancer risk, while those increasing 16alpha-hydroxylation can enhance the risk of breast cancer. Further interest in the biological role of estrogen metabolites has been stimulated by the growing body of evidence that 2-methoxyoestradiol is an endogenous metabolite with anti-mitotic properties. 2-MeOE2 is formed from 2-hydroxy estradiol (2-OHE2) by catechol estrogen methyl transferase, an enzyme that is widely distributed throughout the body.

Workers have shown that in vivo 2-MeOE2 inhibits the growth of tumours arising from the subcutaneous injection of Meth A sarcoma, B16 melanoma or MDA-MB-435 estrogen receptor negative (ER−) breast cancer cells. It also inhibits endothelial cell proliferation and migration, and in vitro angiogenesis. It was suggested that the ability of 2-MeOE2 to inhibit tumour growth in vivo can be due to its ability to inhibit tumour-induced angiogenesis rather than direct inhibition of the proliferation of tumour cells.

The mechanism by which 2-MeOE2 exerts its potent anti-mitogenic and anti-angiogenic effects is still being elucidated. There is evidence that at high concentrations it can inhibit microtubule polymerisation and act as a weak inhibitor of colchicine binding to tubulin. Recently, however, at concentrations that block mitosis, tubulin filaments in cells were not found to be depolymerised but to have an identical morphology to that seen after taxol treatment. It is possible, therefore, that like taxol, a drug that is used for breast and ovarian breast cancer therapy, 2-MeOE2 acts by stabilising microtubule dynamics.

While the identification of 2-MeOE2 as a new therapy for cancer represents an important advance, the bioavailability of orally administered oestrogens is poor. Furthermore, they can undergo extensive metabolism during their first pass through the liver. As part of a research programme to develop a steroid sulphatase inhibitor for breast cancer therapy, oestrone-3-O-sulphamate (EMATE) was identified as a potent active site-directed inhibitor. Unexpectedly, EMATE proved to possess potent oestrogenic properties with its oral uterotrophic activity in rats being a 100-times higher than that of estradiol. Its enhanced oestrogenicity is thought to result from its absorption by red blood cells (rbcs) which protects it from inactivation during its passage through the liver and which act as a reservoir for its slow release for a prolonged period of time. A number of A-ring modified analogues were synthesised and tested, including 2-methoxyoestrone-3-O-sulphamate. While this compound was equipotent with EMATE as a steroid sulphatase inhibitor, it was devoid of oestrogenicity.

The compounds of the present invention provide a means for the treatment of cancers and, especially, breast cancer.

In addition or in the alternative the compound of the present invention can be useful in the blocking the growth of cancers including leukaemias and solid tumours such as breast, endometrium, prostate, ovary and pancreatic tumours.

Therapy Concerning Oestrogen

Some of the compounds of the present invention can be useful in the control of oestrogen levels in the body—in particular in females. Thus, some of the compounds can be useful as providing a means of fertility control—such as an oral contraceptive tablet, pill, solution or lozenge. Alternatively, the compound could be in the form of an implant or as a patch.

Thus, the compounds of the present invention can be useful in treating hormonal conditions associated with oestrogen.

In addition or in the alternative the compound of the present invention can be useful in treating hormonal conditions in addition to those associated with oestrogen. Hence, the compound of the present invention can also be capable of affecting hormonal activity and can also be capable of affecting an immune response.

Neurodegenerative Diseases

Some of the compounds of the present invention can be useful in the treatment of neurodenerative diseases, and similar conditions.

By way of example, it is believed that SOD inhibitors can be useful in the enhancing the memory function of patients suffering from illnesses such as amnesia, head injuries, Alzheimer's disease, epileptic dementia, presenile dementia, post traumatic dementia, senile dementia, vascular dementia and post-stroke dementia or individuals otherwise seeking memory enhancement.

TH1

Some of the compounds of the present invention can be useful in TH1 implications.

By way of example, it is believed that the presence of STS inhibitors within the macrophage or other antigen presenting cells can lead to a decreased ability of sensitised T cells to mount a TH1 (high IL-2, IFNγ low IL-4) response. The normal regulatory influence of other steroids such as glucocorticoids would therefore predominate.

Inflamatory Conditions

Some of the compounds of the present invention can be useful in treating inflammatory conditions—such as conditions associated with any one or more of: autoimmunity, including for example, rheumatoid arthritis, type 1 and 11 diabetes, systemic lupus erythematosus, multiple sclerosis, myasthenia gravis, thyroiditis, vasculitis, ulcerative colitis and Crohn's disease, skin disorders e.g. psoriasis and contact dermatitis; graft versus host disease; eczema; asthma and organ rejection following transplantation.

By way of example, it is believed that SOD inhibitors can prevent the normal physiological effect of DHEA or related steroids on immune and/or inflammatory responses.

The compounds of the present invention can be useful in the manufacture of a medicament for revealing an endogenous glucocorticoid-like effect.

Other Therapies

It is also to be understood that the compound/composition of the present invention can have other important medical implications.

For example, the compound or composition of the present invention can be useful in the treatment of the disorders listed in WO-A-99/52890-viz:

In addition, or in the alternative, the compound or composition of the present invention can be useful in the treatment of the disorders listed in WO-A-98/05635. For ease of reference, part of that list is now provided: cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant, ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention can be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention can be useful in the treatment of disorders listed in WO-A-98/09985. For ease of reference, part of that list is now provided: macrophage inhibitory and/or T cell inhibitory activity and thus, antiinflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

Compound Preparation

The compounds of the present invention can be prepared by reacting an appropriate alcohol with a suitable chloride. By way of example, the sulphamate compounds of the present invention can be prepared by reacting an appropriate alcohol with a suitable sulfamoyl chloride, of the formula $R^4R^5NSO_2Cl$.

Typical conditions for carrying out the reaction are as follows.

Sodium hydride and a sulfamoyl chloride are added to a stirred solution of the alcohol in anhydrous dimethyl formamide at 0° C. Subsequently, the reaction is allowed to warm to room temperature whereupon stirring is continued for a further 24 hours. The reaction mixture is poured onto a cold saturated solution of sodium bicarbonate and the resulting aqueous phase is extracted with dichloromethane. The combined organic extracts are dried over anhydrous $MgSO_4$. Filtration followed by solvent evaporation in vacuo and coevaporated with toluene affords a crude residue which is further purified by flash chromatography.

Preferably, the alcohol is derivatised, as appropriate, prior to reaction with the sulfamoyl chloride. Where necessary, functional groups in the alcohol can be protected in known manner and the protecting group or groups removed at the end of the reaction.

Preferably, the sulphamate compounds are prepared according to the teachings of Page et al (1990 Tetrahedron 46; 2059-2068).

The phosphonate compounds can be prepared by suitably combining the teachings of Page et al (1990 Tetrahedron 46; 2059-2068) and PCT/GB92/01586.

The sulphonate compounds can be prepared by suitably adapting the teachings of Page et al (1990 Tetrahedron 46; 2059-2068) and PCT/GB92/01586.

The thiophosphonate compounds can be prepared by suitably adapting the teachings of Page et al (1990 Tetrahedron 46; 2059-2068) and PCT/GB91/00270.

Preferred preparations are also presented in the following text.

Summary

In summation, the present invention provides a method for the manufacture of a medicament for inhibiting SOD and/or modulating apoptosis and to novel compounds for use in the same and pharmaceutical compositions containing them.

The present invention also provides novel compounds for use as steroid sulphatase inhibitors and/or modulators of apoptosis and/or modulators of cell cycling and/or cell growth, and pharmaceutical compositions containing them.

EXAMPLES

The present invention will now be described only by way of example. However, it is to be understood that the examples also present preferred compounds of the present invention, as well as preferred routes for making same and useful intermediates in the preparation of same.

Example 1

Chemical Synthesis

The structures of the compounds tested are shown in FIG. 1.

2-Substituted oestrones and oestradiols were synthesised from oestrone by either electrophilic substitution (X=F, Cl, Br, I) or by ortho-lithiation of appropriately protected oestrone and quenching with the appropriate electrophile (X=OR, SR etc.) followed by standard transformations to the target compound.

2-Haloestrone (11, 12 and 16) were prepared as described by Page Bulman P C, Hussain F, Maggs J L, Morgan P and Park B K. (1990) Efficient regioselective A-ring functionalisation of oestrogens. *Tetrahedron* 46: 2059-2068

2-Methoxy-17α-estradiol, 4 was prepared by inversion of the 3-O-benzyl derivative of 2-Methoxy-17β-estradiol under Mitsunobu reaction conditions followed by base hydrolysis and hydrogenolysis.

2-Methoxy-3-aminoestrone, 9 was prepared from the 3-(2'-phenyl-4'-quinazolinyloxy) derivative of 2-methoxyestrone in a similar manner to the preparation of 3-aminoestrone as described by Woo L W L, Lightowler, Purohit A, Reed M J and Potter B V L (1996) Heteroatom-substituted analogues of the active site-directed inhibitor estra-1,3,5(10)-trien-17-one-3-sulphamate inhibit oestrone sulfatase by a different mechanism. *J. Steroid Biochem. Molec. Biol.* 57: 79-88.

The coumarin derivative, 14 was prepared by reacting 4-methoxy-1,3-benzenediol and methyl 2-oxo-1-cycloheptanecarboxylate under Pechmann conditions.

2-Allylestrone, 15 was prepared by a Claisen rearrangement of oestrone allyl ether as described by Patton T L (1962) Estrogens. IV. The synthesis of 2- and 4-alkylestrones. *J. Org. Chem.* 27: 910-914.

2-Difluoromethylestrone, 17 was prepared by fluorination of a suitably bis-protected 2-formylestrone with [bis(2-methoxyethyl)amino]sulphur trifluoride (Deoxo-Fluor reagent—Lal G S, Pez P P, Pesaresi R J, Prozonic F M and Cheng H S (1999) [Bis(2-methoxyethyl)amino]sulphur trifluoride: A new broad-spectrum deoxofluorinating agent with enhanced thermal stability. *J. Org. Chem.* 64: 7048-7054) followed by deprotection.

2-Methylsulfoxyestrone, 18 and 2-methylsulfonylestrone, 19 were prepared by oxidation of 2-methylsulfanylestrone with 1.7 eq., at 0° C. and 3.5 eq., at room temperature of 3-chloroperoxybenzoic acid respectively.

2-Nitroestrone, 20 was prepared by nitration of oestrone as described by Tomson A J and Horwitz J P (1959) Some 2- and 4-substituted oestrone 3-methyl ethers. *J. Org. Chem.* 24: 2056-2058.

2-Methoxy-4-nitroestrone, 22 was prepared by nitration of 2-methoxyestrone with nitronium tetrafluoroborate.

2-Methoxy-17α-benzyl-estradiol, 13 and 2-methoxy-17α-(4-tert-butylbenzyl)oestradiol 23 were prepared by direct Grignard reaction on 2-methoxyestrone. Sulfamoylation of phenolic compounds with sulfamoyl chloride was carried out as described by Woo et. al. Stock solutions were made up at 50 mM in tetrahydrofuran and stored at −20° C.

Synthesis of 2-Methylsulfanyl-1,3,5[10]-estratriene-3-ol (8)

17,17-Ethylenedioxy-1,3,5[10]-estratriene-3-ol

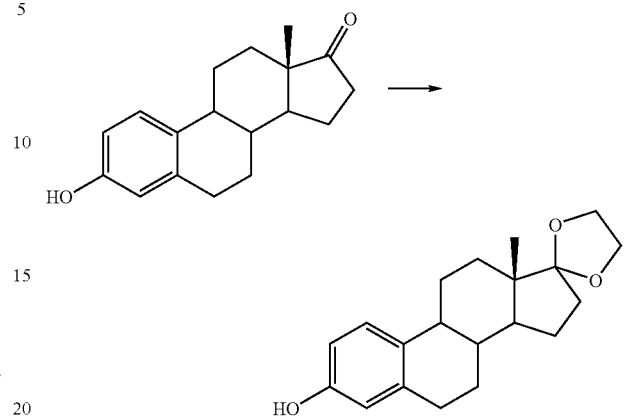

A suspension of oestrone (12.5 g, 46.2 mmol), toluene (150 ml), ethylene glycol (14 ml) and tosic acid (120 mg) was refluxed for 14 h under Dean-Stark conditions. The resultant pale pink transparent solution was poured onto saturated sodium bicarbonate solution (150 ml) and diluted with ethyl acetate (250 ml). The washed organic layer was separated and the aqueous residues extracted with a further aliquot of ethyl acetate (100 ml), the combined organics were washed with water (150 ml) and brine (150 ml), dried and evaporated to yield crude dioxolone (15 g, 103%) as an off-white crystalline solid m.p. 183-184° C. which was used without further purification (NMR shows purity >95%).

17,17-Ethylenedioxy-3-O-methoxymethylene-1,3,5[10]-estratriene

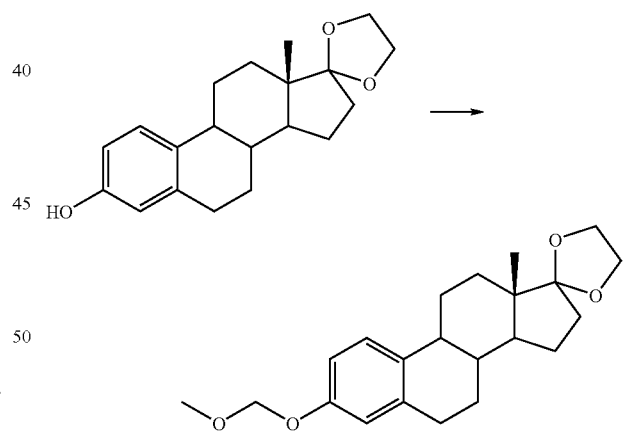

Sodium hydride (1.91 g, 47.7 mmol, 1.5 eq.) was added portion wise to a 0° C. solution of the protected oestrone (18.2 g, 58 mmol) in dimethylformamide (250 ml), after $H_2$ evolution had ceased methyl chloromethyl ether (8.81 ml, 2 eq.) was added in a dropwise manner and the stirred solution was allowed to come to room temperature overnight. The solution was then poured onto ammonia solution (100 ml, 2M) to destroy any remnant haloether contaminants. Ethyl acetate (500 ml) was added and the aqueous layer removed, the organic layer was then washed with brine (5×200 ml) in a portion wise manner, dried and evaporated. The resultant pale yellow oil was purified by column chromatography (4:1 hexane:ethyl acetate, 10 cm diameter column, 20 cm bed depth) to give the product as a colourless oil (18.11 g, 88%) which solidified to give a white crystalline solid m.p. 62-63° C. A further 1.6 g of product was obtained by repurification of mixed column fractions. m.p. 62-63° C., Rf 0.55 (3:1 Hex/EtOAc). $\delta_H$ (270 MHz, CDCl$_3$, ref. TMS=0) 7.21 (1H, d, J 8.6, ArH), 6.82 (1H, d, J 8.6, ArH), 6.77 (1H, app s, ArH), 5.13 (2H, s, OCH$_2$O), 3.89-3.98 (4H, m, OCH$_2$CH$_2$O), 3.46 (3H, s, OCH$_3$), 2.83 (2H, cm, CH$_2$), 2.27 (2H, cm, CH$_2$), 1.25-2.05 (11H, m) and 0.88 (3H, s, CH$_3$). $\delta_C$ 155.0, 138.1, 134.0 (all C), 126.3 (CH), 119.4 (C), 116.2, 113.7 (both CH), 94.5, 65.2, 64.5 (all CH$_2$), 55.9 (CH$_3$), 49.3 (CH), 46.1 (C), 43.7, 38.9 (both CH), 34.2, 30.7, 29.7, 26.9, 26.1, 22.3 (all CH$_2$) and 14.3 (CH$_3$); MS [EI] 358.2(100%, M+); HRMS [EI] 358.214410 C$_{22}$H$_{30}$O$_4$ requires 358.21441.

2-Methylsulfanyl-3-O-methoxymethylene-17,17-ethylene-dioxy-1,3,5[10]-estratriene

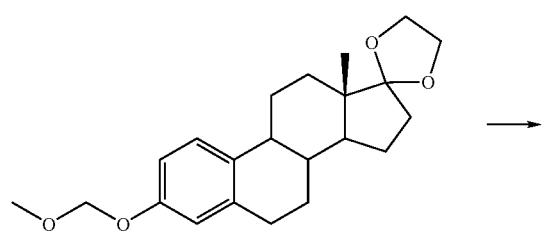

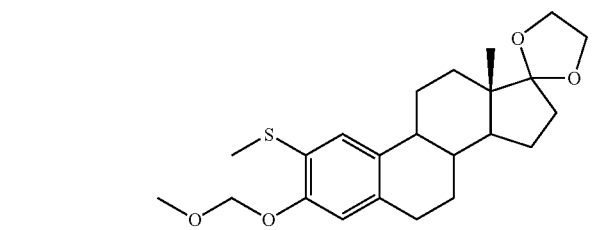

A stirred solution of protected oestrone (20 g, 55.8 mmol) in THF (400 ml) was cooled in a dry ice/acetone bath to −78° C. before treating with sec-butyl lithium (129 ml, 167 mmol, 1.3 M solution in cyclohexane) in a dropwise manner over a period of 1.5 h. The anion was maintained at this temperature for a further hour before then quenching with dimethyl disulfide (20 ml, 223 mmol) over a period of five minutes and then allowed to warm to room temperature over a further 2 h. At this stage saturated ammonium chloride solution (25 ml) was added, the quenched solution diluted in diethyl ether (250 ml) and the organic layers were washed with saturated sodium hydrogen carbonate solution (3×150 ml), water (150 ml) and finally brine (150 ml) before drying (MgSO$_4$) and evaporating to yield a very pale yellow oil. Purification by gradient elution with hexane/ethyl acetate mixtures (100:0 to 85:15) on silica gel gave a pure fraction of the desired sulphide (14.6 g, 36 mmol, 65%) as a clear colourless oil, a further batch of the sulphide (5.9 g, 14.5 mmol) was recovered from the mixed by chromatography to give an overall yield of 20.5 g, 91%.

$\delta_H$ 7.16 (1H, s, ArH), 6.81 (1H, s, ArH), 5.21 (2H, s, OCH$_2$O) 3.86-3.96 (4H, m, OCH$_2$CH$_2$O), 3.51 (3H, s, OMe), 2.43 (3H, s, SMe), 1.25-2.38 (13H, m) and 0.88 (3H, s, 18-CH$_3$).

2-Methylsulfanyl-1,3,5[10]-estratriene-3-ol (8)

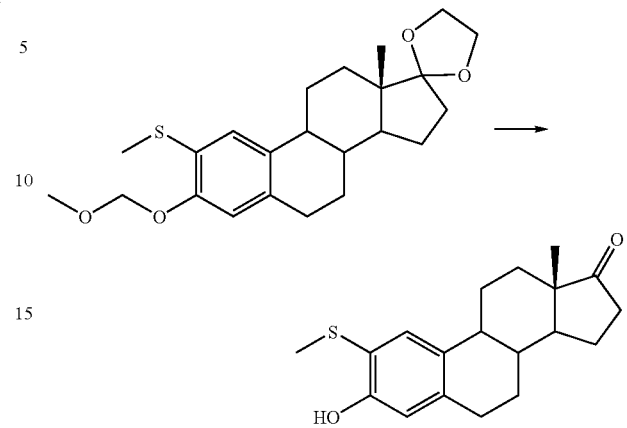

A 4M solution of methanolic HCl was prepared by cautious addition of acetyl chloride (6.1 ml) to ice cold methanol (15.6 ml), after five minutes stirring this solution was poured onto protected oestrone X (1.5 g, 3.72 mmol). Sonication was applied to speed the dissolution of the protected oestrone, a pink colour emerged in the reaction mixture after five minutes and, after a further ten minutes, ethyl acetate (100 ml), and then sufficient sodium hydrogen carbonate to neutralise the reaction mixture was added. The organic layer was then washed with water (2×50 ml) and brine (100 ml) before drying (MgSO$_4$) and evaporating. Purification by gradient elution with hexane/ethyl acetate mixtures (100:0 to 80:20) on silica gel gave a white crystalline solid mp. 153-5° C. which showed: $\delta_H$ (400 MHz, CDCl$_3$) 7.40 (1H, s, OH), 6.73 (1H, s, ArH), 6.49 (1H, s, ArH),2.82-2.91 (2H, m, 6-CH$_2$), 2.34-2.56 (2H, m), 2.30 (3H, s, SMe) 1.36-2.26 (11H, m) and 0.91 (3H, s, 18-CH$_3$); $\delta_C$ 226.4 (CO),154.0, 139.8, 132.5(all C), 131.9, 117.9(both CH), 114.5 (C), 50.4(CH), 48.0 (C), 43.9, 38.2 (both CH) 35.9, 31.6, 29.5, 26.5, 26.0, 21.7(all CH$_2$) 20.3 (SCH$_3$) and 13.9(CH$_3$); Calculated C, 72.11, H, 7.64; Found C 71.8%, H, 7.70%; MS[FAB$^+$] 316.2 (100%, M+); HRMS[FAB$^+$] 316.149702 calculated 316.14970.

Synthesis of 2-Ethylsulfanyl-1,3,5[10]-estratriene-3-ol (10)

2-Ethylsulfanyl-3-O-methoxymethylene-17,17-ethylene-dioxy-1,3,5[10]-estratriene

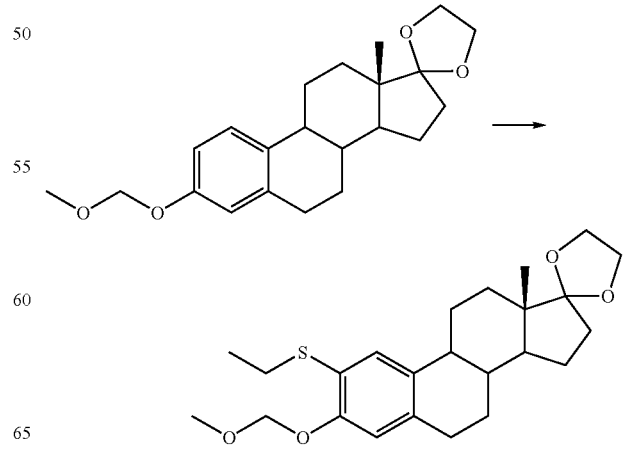

A stirred solution of protected oestrone (5 g, 13.9 mmol) in THF (100 ml) was cooled in a dry ice/acetone bath to −78° C. before treating with sec-butyl lithium (32.2 ml, 41.8 mmol, 1.3 M solution in cyclohexane) in a dropwise manner over a period of 0.5 h. The anion was maintained at this temperature for a further hour and then quenched with diethyl disulfide (9.1 ml, 70 mmol) over a period of five minutes and then allowed to warm to room temperature over a further 2 h. At this stage saturated ammonium chloride solution (10 ml) was added, the quenched solution diluted in diethyl ether (100 ml) and the organic layers were washed with saturated sodium hydrogen carbonate solution (3×50 ml), water (50 ml) and finally brine (50 ml) before drying (MgSO$_4$) and evaporating to yield a very pale yellow oil. Purification by gradient elution with hexane/ethyl acetate mixtures (100:0 to 85:15) on silica gel gave a pure fraction of the desired sulphide (5.3 g, 12.6 mmol, 97%) as a clear colourless oil which showed 7.24 (1H, s, ArH), 6.82 (1H, s, ArH), 5.21 (2H, ArOCH$_2$), 3.86-3.98 (4H, m, OCH$_2$CH$_2$O), 3.51 (3H, s, OMe), 2.79-2.94 (4H, m, SCH$_2$ and 6-CH$_2$) 1.20-2.36 (16H, m [including 1.30 (3H, t, SCH$_2$CH$_3$) and 0.88 (3H, s, 18-CH$_3$); $\delta_C$ 153.3, 136.3, 134.2 (all C), 127.9 (CH), 121.9, 119.3 (both C), 115.0 (CH), 94.8, 65.3, 64.6 (all CH$_2$) 56.2 (CH3), 49.3 (CH), 46.2 (C), 43.7, 38.9 (both CH), 34.3, 30.7, 29.6, 27.1, 27.0, 26.2, 22.4 (all CH$_2$), 14.4 and 14.3 (both CH$_3$)

2-Ethylsulfanyl-1,3,5[10]-estratriene-3-ol (10)

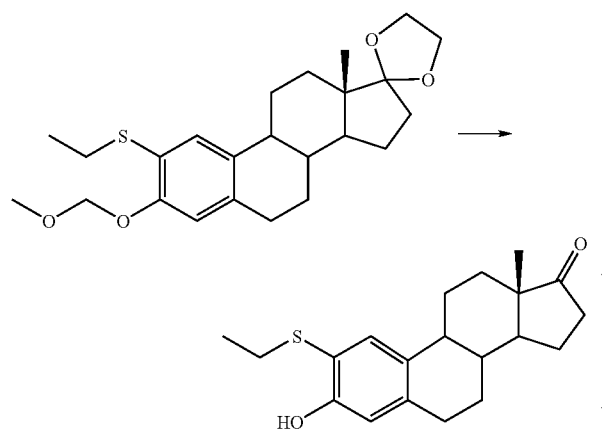

A 4M solution of methanolic HCl was prepared by cautious addition of acetyl chloride (6.1 ml) to ice cold methanol (15.6 ml), after five minutes stirring this solution was poured onto protected oestrone X (1.8 g, 4.3 mmol). Sonication was applied to speed the dissolution of the protected oestrone, a pink colour emerged in the reaction mixture after five minutes and, after a further ten minutes, ethyl acetate (100 ml), and then sufficient sodium hydrogen carbonate to neutralise the reaction mixture was added. The organic layer was then washed with water (2×50 ml) and brine (100 ml) before drying (MgSO$_4$) and evaporating. Purification by crystallisation (ethanol) gave a yellow crystalline solid mp. 139-141° C. which showed: $\delta_H$ (400 MHz, CDCl$_3$) 7.36 (1H, s, OH), 6.73 (1H, s, ArH), 6.57 (1H, s, ArH), 2.82-91 (2H, m, 6-CH$_2$),2.66 (2H, q, J7.4, SCH$_2$), 1.36-2.55 (13H, m), 1.21 (3H, t, J 7.4, SCH$_2$CH$_3$) and 0.91 (3H, s, 18-CH$_3$); $\delta_C$ 220.5 (CO), 154.7, 140.0 (both C), 133.0 (CH), 132.2 (C), 115.7 (CH), 114.3 (C), 50.4 (CH), 48.0 (C), 43.9 (CH), 38.2 (CH), 35.9, 31.6, 31.1, 29.5, 26.5, 26.0, 21.7 (all CH$_2$), 15.2 and 14.0 (both CH$_3$); MS[FAB$^+$] 330.2 (100%, M+), HRMS[FAB$^+$] 330.165352, calculated 330.16535; Calculated C, 72.69, H, 7.93; Found C 72.9%, H, 7.99%.

Synthesis of 2-Methylsulfanyl-17-deoxy-1,3,5[10]-estratrien-3-ol (28)

3-O-Methoxymethylene-17-deoxy-1,3,5[10]-estratriene

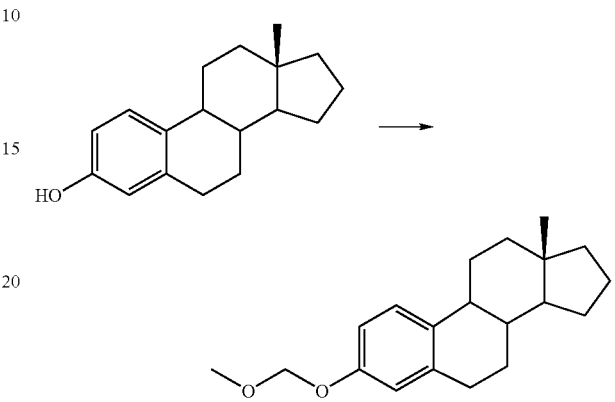

A stirred, 0° C., solution of 17-deoxy-1,3,5[10]-estratriene (3.12 g, 12.2 mmol), in dimethylformamide (50 ml) was treated sodium hydride (731 mg, 18.3 mmol) in a portion wise manner. After 0.5 h stirring methyl chloromethyl ether (0.93 ml, 25 mmol) was added and the reaction mixture was left to stir overnight. Aqueous 2M ammonia (10 ml) was added to destroy excess chlorinated starting material and after a further 10 minutes ethyl acetate (200 ml) and brine (50 ml) were added. The organic layer was separated and washed five times with brine (50 ml aliquots), dried, evaporated and columned on silica gel (9:1 hexane:ethyl acetate as eluant) to give the desired protected 3-O-methoxymethylene-17-deoxy-1,3,5[10]-estratriene as a clear colourless oil which showed $\delta_H$ 7.21 (1H, d, J 8.5), 6.82 (1H, dd, J8.5 and 2.3, ArH), 6.77 (1H, d, J2.3, ArH), 5.14 (2H, s, OCH$_2$O), 3.47 (3H, s, OCH$_3$), 2.78-2.86 (2H, m, 6-CH$_2$), 1.15-2.30 (15H, m) and 0.73 (3H, s, 18-CH$_3$); $\delta_C$ 154.8, 138.0, 134.3, 126.3, 116.1, 113.6, 94.4, 55.9, 53.6, 44.2, 41.1, 40.6, 39.1, 38.9, 30.0, 28.2, 26.8, 25.3, 20.7 and 17.7.

2-Methylsulfanyl-3-O-methoxymethylene-17-deoxy-1,3,5[10]-estratriene

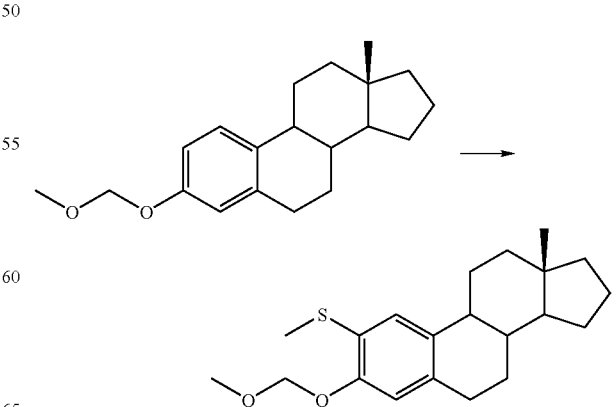

A stirred solution of 3-O-methoxymethylene-17-deoxy-1,3,5[10]-estratriene (2.78 g, 9.35 mmol) in THF (100 ml) was cooled in a dry ice/acetone bath to −78° C. before treating with sec-butyl lithium (28 ml, 21.5 mmol, 1.3 M solution in cyclohexane) in a dropwise manner over a period of 0.5 h. The anion maintained at this temperature for 1 h and was then quenched with dimethyl disulfide (4.2 ml, 47 mmol) over a period of five minutes, and then allowed to warm to room temperature over a further 2 h. At this stage saturated ammonium chloride solution (10 ml) was added, the quenched solution diluted in diethyl ether (100 ml) and the organic layers were washed with saturated sodium hydrogen carbonate solution (3×50 ml), water (50 ml) and finally brine (50 ml) before drying (MgSO$_4$) and evaporating to yield the desired product, 2-methylsulfanyl-3-O-methoxymethylene-17-deoxy-1,3,5[10]-estratriene as a spectro-scopically pure yellow oil (2.2 g, 68%) which showed δ$_H$ 7.16 (1H, s, ArH), 6.81 (1H, s, ArH), 5.20 (2H, S, OCH$_2$O), 3.51 (3H, s, OMe), 2.78-2.86 (2H, m, 6-CH$_2$), 2.43 (3H, s, SMe), 1.10-2.36 (15H, m) and 0.74 (3H, s, 18CH$_3$).

2-Methylsulfanyl-17-deoxy-1,3,5[10]-estratrien-3-ol (28)

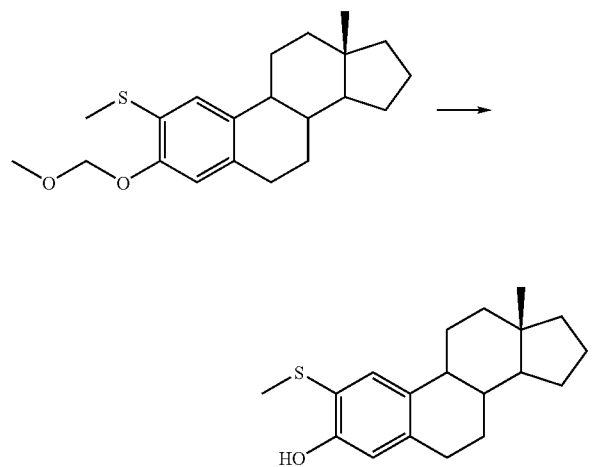

A 4M solution of methanolic HCl was prepared by cautious addition of acetyl chloride (6.1 ml) to ice cold methanol (15.6 ml), after five minutes stirring this solution was poured onto 2-methylsulfanyl-3-O-methoxymethylene-17-deoxy-1,3,5[10]-estratriene (1.8 g, 5.2 mmol). Sonication was applied to speed the dissolution of the protected estrone, a pink colour emerged in the reaction mixture after five minutes and, after a further ten minutes, ethyl acetate (100 ml), and then sufficient sodium hydrogen carbonate to neutralise the reaction mixture was added. The organic layer was then washed with water (2×50 ml) and brine (100 ml) before drying (MgSO$_4$) and evaporating. Purification by column chromatography (8:1 hexane:ethyl acetate) gave the desired product, 2-methylsulfanyl-17-deoxy-1,3,5[10]-estratrien-3-ol, as a clear colourless oil (1.13 g, 72%) which showed δ$_H$ 7.41 (1H, s, OH), 6.78 (1H, s, ArH), 6.45 (1H, s, ArH), 2.78-2.85 (2H, m, 6-CH2), 1.08-2.32 (18H, m [including 2.29 (3H, s, SMe)]) and 0.74 (3H, s, 18-CH$_3$); δ$_c$ 153.7, 140.2, 133.6 (all C), 131.9 (CH), 117.4 (C), 114.4, 53.5, 43.9 (all CH), 41.0 (CH$_2$), 40.5, 39.0 (both CH), 38.8, 0.6 (both CH$_3$); m/z [FAB$^+$] $^{302.2}$ (M$^+$+H, SO requires 302.170437.

Synthesis of 2-Methoxy-17-deoxyestrone (29)

2-Formyl-3-O-methoxymethyl-17-deoxyestrone

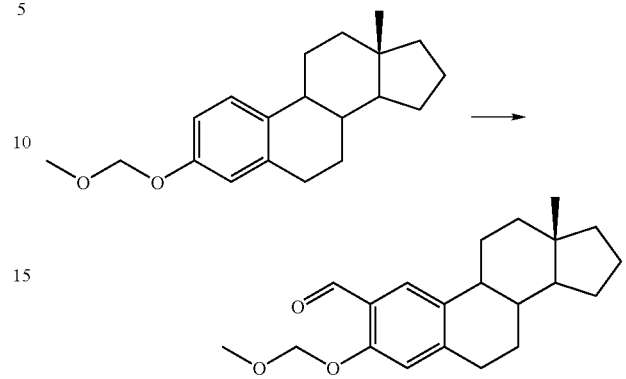

A solution of 3-O-methoxymethylene-17-deoxy-1,3,5[10]-estratriene (2.5 g, 8.33 mmol) in THF (150 ml) was cooled in a dry ice acetone bath to −75° C. and then treated with sec-butyl lithium (22 ml of a 1.3M soln in hexanes, 29 mmol) over a period of 20 minutes, after a further two hours stirring freshly distilled DMF (2.5 ml, 60 mmol) was added to the reaction mixture and the reaction was allowed to come to room temperature over the next 16 hours. The reaction mixture was then cooled in an ice bath before quenching with ammonium chloride solution (10 ml), adding ethyl acetate (200 ml) and transferring into a separating funnel. The organic layers were combined and washed with water (3×100 ml) and brine (100 ml) before drying and evaporating. The crude product was purified by column chromatography to give the product as a clear colourless oil (1.9 g, 70%) which showed δ$_H$ 10.43 (1H, s, CHO), 7.78, (1H, s, ArH), 6.91 (1H, s, ArH), 5.26 (2H, s, OCH$_2$O), 3.51 (3H, s, OMe), 2.86-2.95 (2H, m, 6-CH$_2$), 1.10-2.41 (15H, m) and 0.73 (3H, s, 18-CH$_3$); δ$_C$ 189.4, 157.2, 146.3, 134.8 (C), 125.2 (CH), 123.2 (C), 114.8 (CH), 94.5 (CH$_2$), 56.4 (CH$_3$), 53.6, 43.9 (both CH), 41.1 (C), 40.5 (CH$_2$), 38.9 (CH), 30.7, 27.8, 26.7, 25.3, 20.7 (all CH$_2$) and 17.6 (CH$_3$); m/z [FAB$^+$] $_{329.3}$ (M$^+$+H, 80%). Accurate mass [FAB$^+$] found 328.20385, C$_{21}$H$_{28}$O$_3$ requires 328.20385.

2-Hydroxy-3-O-methoxymethyl-17-deoxyestrone

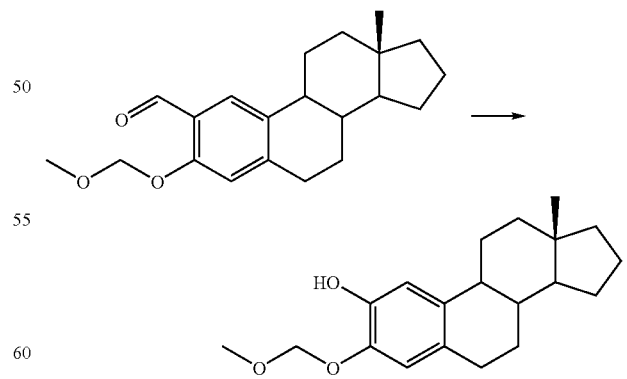

A stirred solution of 2-formyl-3-O-methoxymethyl-17-deoxyestrone (1.66 g, 5 mmol) in a 3:1 mixture of chloroform and dichloromethane (40 ml) was treated with dibasic sodium hydrogen phosphate (2.48 g, 17.5 mmol) and then, in a dropwise manner, mCPBA (1.73 g, 9 mmol). After five hours the reaction mixture was pured onto ice water (50 ml), extracted with dichloromethane (50 ml) and the combined organics washed with sodium hydrogen carbonate (50 ml), water (50 ml) and brine (50 ml) before drying and evaporating to give a pale yellow foam. The foam was dissolved in degassed methanol (25 ml), then treated with sodium hydroxide (9 ml, 1.8 eq) and stirred for one hour before neutralising with hydrochloric acid (1M) and removing the solvent in vacuo. The residues were diluted in ethyl acetate (40 ml) and water (40 ml), the organic layer separated, dried and evaporated to yield the crude product. Purification by column chromatography afforded the desired phenol as a clear colourless oil (1.1 g, 70%) which showed $\delta_H$ 6.90 (1H, s, ArH), 6.78 (1H, s, ArH), 5.74 (1H, s, OH), 5.15 (2H, s, OCH$_2$O), 3.51 (3H, s, OMe), 2.70-2.84 (2H, m, 6-CH$_2$), 1.08-2.26 (15H, m) and 0.73 (3H, s, 18-CH$_3$); $\delta_C$ 143.8, 142.1, 135.5, 128.4 (all C), 115.7, 112.3 (both CH), 96.0 (CH$_2$), 56.4 (CH$_3$), 53.6, 44.3 (both CH), 41.1 (C), 40.6 (CH$_2$), 39.1 (CH), 38.9, 29.3, 28.4, 26.8, 25.3, 20.7 (all CH$_2$) and 17.6 (CH$_3$).

2-Methoxy-3-O-methoxymethyl-17-deoxyestrone

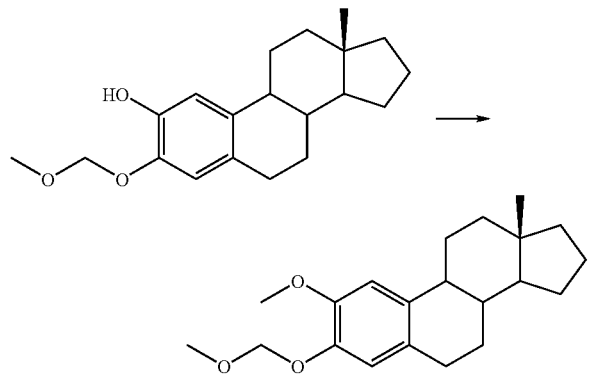

A solution of 2-hydroxy-3-O-methoxymethyl-17-deoxyestrone (900 mg, 2.84 mmol) in DMF (50 ml) was treated with potassium carbonate (4.14 g, mmol) and then, after ten minutes stirring with methyl iodide (2 ml, 33 mmol) and tetrabutylammonium iodide (100 mg). After stirring for 48 h the reaction was poured onto brine (75 ml) and extracted with ethyl acetate (200 ml), the organic layer was extracted with brine (6×100 ml), dried and evaporated. The desired product, a clear colourless oil (300 mg, 32%) was isolated by column chromatography and showed $\delta_H$ 6.87 (1H, s, ArH), 6.86 (1H, s, ArH), 5.19 (2H, s, OCH$_2$O), 3.85 (3H, s, OMe), 3.51 (3H, s, OMe), 2.75-2.86 (2H, m, 6-CH$_2$), 1.10-2.30 (15H, m) and 0.74 (3H, s, 18-CH$_3$); $\delta_C$ 144.5, 144.2, 134.5, 129.0 (all C), 116.8, 109.5 (both CH), 95.6 (OCH$_2$O), 56.1, 56.1 (both OCH$_3$), 53.6, 44.5 (both CH), 41.1 (C), 40.6 (CH$_2$), 39.1 (CH), 38.9, 29.3, 28.3, 27.0, 25.3, 20.7 (all CH$_2$) and 17.7 (CH$_3$).

2-Methoxy-17-deoxyestrone

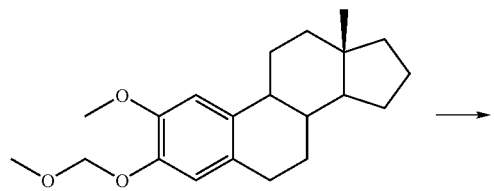

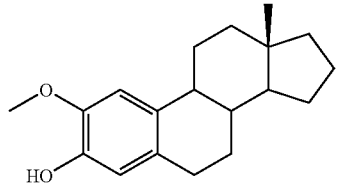

A solution of methanolic HCl was formed by cautious addition of acetyl chloride (0.85 ml) to vigorously stirred ice cold methanol (2.2 ml), after ten minutes stirring the methanolic HCl was added to 2-methoxy-3-O-methoxymethyl-17-deoxyestrone e (200 mg, 0.61 mmol). To aid solvation of the starting material the reaction was sonicated for 5 minutes after which time saturated sodium hydrogen carbonate solution (35 ml) and then ethyl acetate was added, the organic layer was separated, the aqueous layer extracted with a further aliquot of ethyl acetate (30 ml) and the combined organic layers were washed with NaHCO$_3$ (25 ml), water (50 ml) and brine (50 ml). The resultant solution was dried and evaporated to give the crude product a yellow oil which was purified by column chromatography (chloroform) to give 2-methoxy-17-deoxyestrone as a white crystalline solid (150 mg, 86%) mp 112-115° C. m/z (FAB$^+$) 286.2 (100%, M+). Accurate mass [FAB$^+$] found 286.19328 C$_{19}$H$_{26}$O$_2$ requires 286.19328.

Superoxide Dismutase Assay

SOD activity was measured in accordance with Protocol 1.

Results and Discussion

We determined the SOD-inhibitory action of 27 compounds. Initial analyses were performed using test compounds at 100 µM. Compounds which gave >50% inhibition at this concentration were tested in additional titration experiments to determine IC50 values (Table).

| Compound | IC 50/µM (+/− SEM) SOD Inhibition |
|---|---|
| 2-methylsulfanylestradiol 1 | 10 +/− 2 |
| 2-ethoxyestradiol 2 | 11 +/− 1 |
| 2-methoxy-17β-estradiol 3 | 12 +/− 4 |
| 2-methoxy-17α-estradiol 4 | 13 +/− 1 |
| 2-methoxyestrone 5 | 14 +/− 2 |
| 2-ethylsulfanylestradiol 6 | 14 +/− 1 |
| 2-ethoxyestrone 7 | 19 +/− 3 |
| 2-methylsulfanylestrone 8 | 21 +/− 5 |
| 2-methoxy-3-aminoestrone 9 | 79 +/− 13 |
| 2-ethylsulfanylestrone 10 | 79 +/− 5 |
| 2-fluoroestrone 11 | 81 +/− 1 |
| 2-chloroestrone 12 | 83 +/− 1 |
| 2-methoxy-17α-benzyl-estradiol 13 | 88 +/− 1 |
| 3-Hydroxy-2-methoxy-6-oxo-8,9,10,11-tetrahydro-7H-cyclohepta-[c][1]benzopyran 14 | 91 +/− 11 |
| 2-allylestrone 15 | >100 |
| 2-iodoestrone 16 | >100 |
| 2-difluoromethylestrone 17 | >100 |
| 2-methylsulfoxyestrone 18 | >100 |
| 2-methylsulfonylestrone 19 | >100 |
| 2-nitroestrone 20 | >100 |
| 2-ethylestrone 21 | >100 |
| 2-methoxy-4-nitroestrone 22 | >100 |
| 2-methoxy-17α-(4-tert-butylbenzyl)oestradiol 23 | >100 |
| estrone-3-O-sulphamate 24 | >100 |
| 2-methoxyestrone-3-O-sulphamate 25 | >100 |
| 2-ethylestrone-3-O-sulphamate 26 | >100 |
| equilin-3-O-sulphamate 27 | >100 |
| 2-methylsulfanyl-17-deoxyoestrone 28 | >100 |
| 2-methoxy-17-deoxyoestrone 29 | >100 |

The structure-activity relationships for the potent inhibition of SOD activity by the compounds studied in this work are summarised in FIG. 2.

For the 2-substituted oestrones or oestradiols that were tested here, only those compounds with either an O or S substituent show potent or good inhibitory activities against SOD. The poor inhibition exhibited by 2-ethylestrone, 21 confirms such generalisation that a heteroatom of either oxygen or sulphur at the 2-position is important for potency. Although the 2-alkoxy derivative of oestrone was a more potent inhibitor than the 2-alkylsulfanyl derivative (7 vs 10) the overall difference in potencies between the corresponding 2-alkoxy and 2-alkylsulfanyl pairs (2 vs 6, 5 vs 8, and 1 vs 3) was often relatively small suggesting that the enzyme tolerates the sulphur atom reasonably well despite its bigger size and lower electronegativity than oxygen atom All 2-alkylsulfanyl derivatives of oestrone or oestradiol are less potent than the corresponding 2-alkoxy derivatives (e.g. 2 vs 6, 5 vs 8 and 7 vs 10) with the exception of 2-methylsulfanylestradiol, 1 which appears to be the best SOD inhibitor tested here, even better than 2-methoxyestradiol, 3. However, the difference in potencies between the corresponding pairs (except 7 vs 10) is relatively small which suggests that the enzyme tolerates the sulphur atom reasonably well despite its bigger size and lower electronegativity than oxygen atom.

The oxidation state of the sulphur atom is important for high potency since the tricoordinate 2-methylsulfoxy derivative, 18 and the tetracoordinate 2-methylsulphonyl derivative of oestrone, 19 are much weaker inhibitors than all divalent thio derivatives in this series such as 1 and 6. Our data have also shown that in general the potency of a 2-alkoxy or 2-alkylsulfanyl derivative decreases with an increase in the carbon chain length of its alkyl group. It is therefore anticipated that derivatives of oestrone or oestradiol with bulkier substituents such as propoxy or propylsulfanyl at the 2-position will not be well tolerated by SOD and hence would be weaker inhibitors.

Other substituents at the 2-position are clearly detrimental as shown by the poor inhibitions of 2-allyl-, 15, 2-difluoromethyl-, 17 and 2-nitroestrone, 20. Interestingly, a single halo atom at the 2-position exhibits weak activity although this appears to be related to the size and presumably the electronegativity of the halogen with 2-fluoroestrone, 11 the most active and 2-iodoestrone, 16 the weakest in this series.

Replacement of the hydroxy group at the 3-position by a sulphamate group is detrimental to the inhibitory activities exhibited by their parental compounds. Whilst 2-methoxyestrone, 5 is highly potent, the IC50 for its sulphamate derivative was found to be >100 μM. However, when the hydroxy group of 5 is replaced with an amino group, compound 9 has retained a small level of inhibitory activity suggesting that the hydroxy group at the 3-position is not be an absolute requirement for activity. Clearly, any potential hydrogen bonding interaction of the 3-OH of 2-methoxyestradiol with amino acid residues in the enzyme active site could be maintained in 9, but not in 25.

Substitution at the 4-position of 2-methoxyestrone with a nitro group induced a significant loss in inhibitory activity of 5. However, it is not clear if such an effect is the result of steric hindrance or electronic factors.

It was interesting that a non-steroidal tricyclic coumarin-based compound shows detectable inhibitory activity showing that the steroidal scaffold is not be an absolute requirement for inhibitory activity. Mimicking the A-ring of 2-methoxyestradiol alone might produce inhibitory effects. To the best of our knowledge, this is the first report that a non-steroidal compound can work as a SOD inhibitor. It is anticipated that the inhibitory activity of the coumaric 14 could be further optimized to produce more potent analogues that might emerge as a new class of SOD inhibitors.

The potency of 2-methoxyestradiol is not significantly affected by the stereochemistry of the hydroxy group at the 17-position as shown by the similar potency observed for the 17β-OH derivative, 3 and its epimeric 17α-OH derivative, 4. It does however appear that all oestradiol derivatives are better SOD inhibitors than their oestrone congeners as shown by the relative inhibitory activities of 1 vs 8, 3 vs 5 and 2 vs 7; this is clearest for the 2-ethylsulfanyl derivatives (6 vs 10). It is clear that the enzyme tolerates the 17α-benzyl group of 13 much better than the bulkier 17β-4-tert-butyl-benzyl group of 23. Hence, small substituents and structural changes at this position might not alter the potency of the parental compound to a large extent but it is likely that increasing bulky group is not tolerated.

Interestingly, the potency of the 17-deoxy analogues (24 and 25) proved to be very weak ($IC_{50}$>100 μM). This contrasts with their parent oestradiols (1 and 3) and oestrones (8 and 5) respectively, all of which show potent inhibitory activity. Hence, deletion of these 17 position motifs leads to a dramatic loss of activity. The similar activity of both parent oestradiols (potential H-bond acceptors and donors at C-17) and oestrones (potential H-bond acceptors at C-17) imply that the presence of an H-bond acceptor at the 17-position could be important in binding to SOD and deletion of this motif in 24 and 25 abolishes activity. Notably the 17-α derivative 4 is still potent implying that its O-atom of the 17-OH can still potentially act as an H-bond acceptor.

CONCLUSIONS

Our study has shown that synthetic analogues can be equipotent to, or more potent than, 2-methoxyestradiol, a natural ligand for the SOD enzyme. A S or O containing substituent is pivotal for SOD inhibition. We demonstrate here, for the first time, that the steroidal skeleton of 2-methoxyestradiol can be replaced by a non-steroidal scaffold without a complete loss of inhibitory activity. Such observations, together with the structure-activity relationships for SOD inhibition derived from this work, will facilitate the design of more potent steroidal and non-steroidal-based SOD inhibitors in the future.

Example 2

Synthesis of
2-Methylsulfanyl-1,3,5[10]-estratriene-3-ol (36)

17,17-Ethylenedioxy-1,3,5[10]-estratriene-3-ol

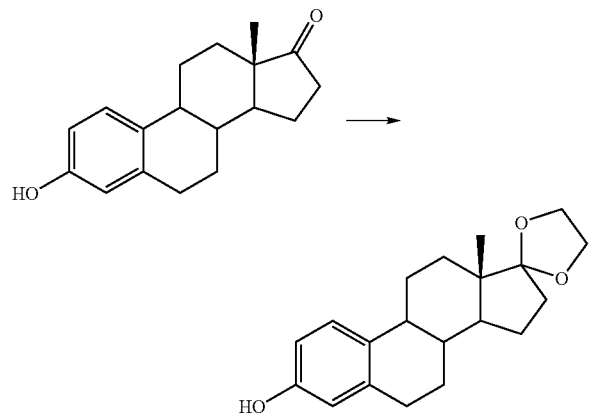

A suspension of estrone (12.5 g, 46.2 mmol), toluene (150 ml), ethylene glycol (14 ml) and tosic acid (120 mg) was refluxed for 14 h under Dean-Stark conditions. The resultant pale pink transparent solution was poured onto saturated sodium bicarbonate solution (150 ml) and diluted with ethyl acetate (250 ml). The washed organic layer was separated and the aqueous residues extracted with a further alliquot of ethyl acetate (100 ml), the combined organics were washed with water (150 ml) and brine (150 ml), dried and evaporated to yield crude dioxolone (15 g, 103%) as an off-white crystalline solid m.p. 183-184° C. which was used without further purification (NMR shows purity >95%).

17,17-Ethylenedioxy-3-O-methoxymethylene-1,3,5[10]-estratriene

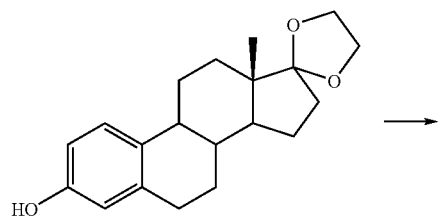

Sodium hydride (1.91 g, 47.7 mmol, 1.5 eq.) was added portion wise to a 0° C. solution of the protected estrone (18.2 g, 58 mmol) in dimethylformamide (250 ml), after $H_2$ evolution had ceased methyl chloromethyl ether (8.81 ml, 2 eq.) was added in a dropwise manner and the stirred solution was allowed to come to room temperature overnight. The solution was then poured onto ammonia solution (100 ml, 2M) to destroy any remnant haloether contaminants. Ethyl acetate (500 ml) was added and the aqueous layer removed, the organic layer was then washed with brine (5×200 ml) in a portion wise manner, dried and evaporated. The resultant pale yellow oil was purified by column chromatography (4:1 hexane:ethyl acetate, 10 cm diameter column, 20 cm bed depth) to give the product as a colourless oil (18.11 g, 88%) which solidified to give a white crystalline solid m.p. 62-63° C. A further 1.6 g of product was obtained by repurification of mixed column fractions. m.p. 62-63° C., Rf 0.55 (3:1 Hex/EtOAc). $\delta_H$ (270 MHz, $CDCl_3$, ref. TMS=0) 7.21 (1H, d, J 8.6, ArH), 6.82 (1H, d, J 8.6, ArH), 6.77 (1H, app s, ArH), 5.13 (2H, s, $OCH_2O$), 3.89-3.98 (4H, m, $OCH_2CH_2O$), 3.46 (3H, s, $OCH_3$), 2.83 (2H, cm, $CH_2$), 2.27 (2H, cm, $CH_2$), 1.25-2.05 (11H, m) and 0.88 (3H, s, $CH_3$). $\delta_C$ 155.0, 138.1, 134.0 (all C), 126.3 (CH), 119.4 (C), 116.2, 113.7 (both CH), 94.5, 65.2, 64.5 (all $CH_2$), 55.9 ($CH_3$), 49.3 (CH), 46.1 (C), 43.7, 38.9 (both CH), 34.2, 30.7, 29.7, 26.9, 26.1, 22.3 (all $CH_2$) and 14.3 ($CH_3$); MS [EI] 358.2(100%, M+); HRMS [EI] 358.214410 $C_{22}H_{30}O_4$ requires 358.21441.

2-Methylsulfanyl-3-O-methoxymethylene-17,17-ethylenedioxy-1,3,5[10]-estratriene

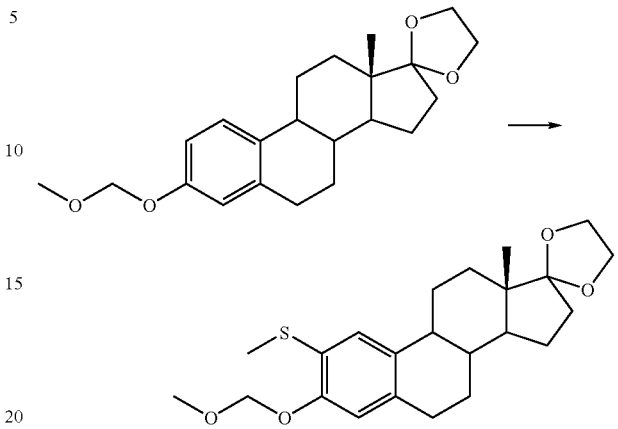

A stirred solution of protected estrone (20 g, 55.8 mmol) in THF (400 ml) was cooled in a dry ice/acetone bath to −78° C. before treating with sec-butyl lithium (129 ml, 167 mmol, 1.3 M solution in cyclohexane) in a dropwise manner over a period of 1.5 h. The anion was maintained at this temperature for a further hour before then quenching with dimethyl disulfide (20 ml, 223 mmol) over a period of five minutes and then allowed to warm to room temperature over a further 2 h. At this stage saturated ammonium chloride solution (25 ml) was added, the quenched solution diluted in diethyl ether (250 ml) and the organic layers were washed with saturated sodium hydrogen carbonate solution (3×150 ml), water (150 ml) and finally brine (150 ml) before drying ($MgSO_4$) and evaporating to yield a very pale yellow oil. Purification by gradient elution with hexane/ethyl acetate mixtures (100:0 to 85:15) on silica gel gave a pure fraction of the desired sulphide (14.6 g, 36 mmol, 65%) as a clear colourless oil, a further batch of the sulphide (5.9 g, 14.5 mmol) was recovered from the mixed by chromatography to give an overall yield of 20.5 g, 91%.

2-Methylsulfanyl-1,3,5[10]-estratriene-3-ol (35)

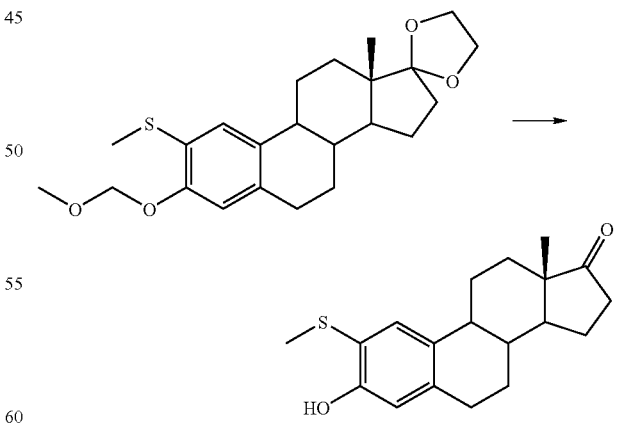

A 4M solution of methanolic HCl was prepared by cautious addition of acetyl chloride (6.1 ml) to ice cold methanol (15.6 ml), after five minutes stirring this solution was poured onto protected estrone X (1.5 g, 3.72 mmol). Sonication was applied to speed the dissolution of the protected estrone, a pink colour emerged in the reaction mixture after five minutes and, after a further ten minutes, ethyl acetate (100 ml), and then sufficient sodium hydrogen carbonate to neutralise the reaction mixture was added. The organic layer was then washed with water (2×50 ml) and brine (100 ml) before drying (MgSO$_4$) and evaporating. Purification by gradient elution with hexane/ethyl acetate mixtures (100:0 to 80:20) on silica gel gave a white crystalline solid mp. 153-5° C. which showed: $\delta_H$ (400 MHz, CDCl$_3$) 7.40 (1H, s, OH), 6.73 (1H, s, ArH), 6.49 (1H, s, ArH),2.82-2.91 (2H, m, 6-CH$_2$), 2.34-2.56 (2H, m), 2.30 (3H, s, SMe) 1.36-2.26 (11H, m) and 0.91 (3H, s, 18-CH$_3$); $\delta_C$ 226.4 (CO),154.0, 139.8, 132.5(all C), 131.9, 117.9(both CH), 114.5 (C), 50.4(CH), 48.0 (C), 43.9, 38.2 (both CH) 35.9, 31.6, 29.5, 26.5, 26.0, 21.7(all CH$_2$) 20.3 (SCH$_3$) and 13.9(CH$_3$); Calculated C, 72.11, H, 7.64; Found C 71.8%, H, 7.70%; MS[FAB$^{+}$] 316.2 (100%, M+); HRMS[FAB$^{+}$] 316.149702 calculated 316.14970.

2-Methylsulfanyl-3-O-sulfamoyl-1,3,5[10]-estratriene (36)

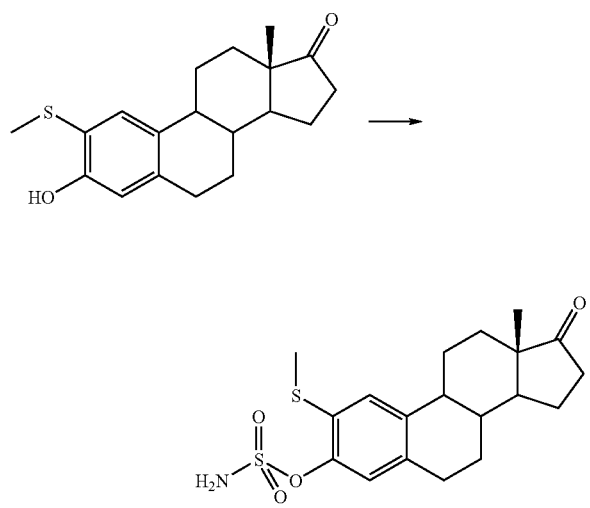

A stirred solution of 2-methylsulfanylestrone (400 mg, 1.26 mmol) in dichloromethane (20 ml) was treated with 2,6-di-tert-butyl-4-methylpyridine (776 mg, 3.78 mmol) at room temperature. After a further five minutes sulfamoyl chloride (5.4 ml, 3.78 mmol, 0.7M in toluene) was added in a dropwise manner and the resultant yellow solution was stirred for 16 h. The reaction mixture was then poured onto water (25 ml), the organic layer separated and washed with water until neutral, dried and evaporated to give an oil. Column chromatography (chloroform: ethyl acetate 9:1) gave the desired sulfamates as a white crystalline solid mp 184-5° C. which showed $\delta_H$ (400 MHz, CD$_3$OD) 7.23 (1H, s, ArH), 7.12 (1H, s, ArH), 4.88 (2H, br s, NH$_2$), 2.82-2.90 (2H, m, 6-CH$_2$), 1.38-2.54 (16H, m [including 2.41 (3H, s, SMe)]) and 0.91 (3H, s, 18-CH$_3$); $\delta_C$ (100 MHz, CD$_3$OD=49.8) 220.2 (CO), 148.1, 140.6, 137.1, 130.7 (C), 126.9, 123.8, 52.4, 46.3, 40.2 (all CH), 37.5, 33.6, 30.8, 28.2, 27.8, 23.4 (all CH$_2$), 16.6 and 15.1 (both CH$_3$) NB. C-17 quaternary carbon lies under the resonance for CD$_3$OD; MS[FAB$^{+}$] $^{395.2}$(M, 55%), 255.2(170); [FAB-] 394.1 (100%); HRMS [FAB$^{+}$] 395.12250, calculated 395.12250.

Example 3

Synthesis of 2-Ethylsulfanyl-3-O-sulfamoyl-1,3,5 [10]-estratriene (38)

2-Ethylsulfanyl-3-O-methoxymethylene-17,17-ethylenedioxy-1,3,5[10]-estratriene

A stirred solution of protected estrone (5 g, 13.9 mmol) in THF (100 ml) was cooled in a dry ice/acetone bath to −78° C. before treating with sec-butyl lithium (32.2 ml, 41.8 mmol, 1.3 M solution in cyclohexane) in a dropwise manner over a period of 0.5 h. The anion was maintained at this temperature for a further hour and then quenched with diethyl disulfide (9.1 ml, 70 mmol) over a period of five minutes and then allowed to warm to room temperature over a further 2 h. At this stage saturated ammonium chloride solution (10 ml) was added, the quenched solution diluted in diethyl ether (100 ml) and the organic layers were washed with saturated sodium hydrogen carbonate solution (3×50 ml), water (50 ml) and finally brine (50 ml) before drying (MgSO$_4$) and evaporating to yield a very pale yellow oil. Purification by gradient elution with hexane/ethyl acetate mixtures (100:0 to 85:15) on silica gel gave a pure fraction of the desired sulphide (5.3 g, 12.6 mmol, 97%) as a clear colourless oil which showed 7.24 (1H, s, ArH), 6.82 (1H, s, ArH), 5.21 (2H, ArOCH$_2$), 3.86-3.98 (4H, m, OCH$_2$CH$_2$O), 3.51 (3H, s, OMe), 2.79-2.94 (4H, m, SCH$_2$ and 6-CH$_2$) 1.20-2.36 (16H, m [including 1.30 (3H, t, SCH$_2$CH$_3$) and 0.88 (3H, s, 18-CH$_3$); $\delta_C$ 153.3, 136.3, 134.2 (all C), 127.9 (CH), 121.9, 119.3 (both C), 115.0 (CH), 94.8, 65.3, 64.6 (all CH$_2$) 56.2 (CH3), 49.3 (CH), 46.2 (C), 43.7, 38.9 (both CH), 34.3, 30.7, 29.6, 27.1, 27.0, 26.2, 22.4 (all CH$_2$), 14.4 and 14.3 (both CH$_3$)

2-Ethylsulfanyl-1,3,5[10]-estratriene-3-ol (37)

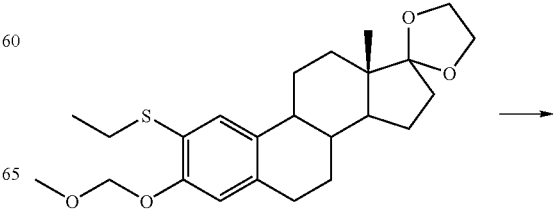

-continued

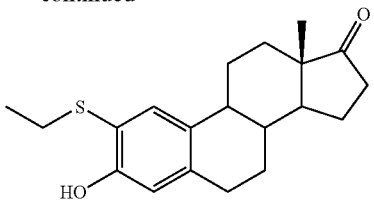

A 4M solution of methanolic HCl was prepared by cautious addition of acetyl chloride (6.1 ml) to ice cold methanol (15.6 ml), after five minutes stirring this solution was poured onto protected estrone X (1.8 g, 4.3 mmol). Sonication was applied to speed the dissolution of the protected estrone, a pink colour emerged in the reaction mixture after five minutes and, after a further ten minutes, ethyl acetate (100 ml), and then sufficient sodium hydrogen carbonate to neutralise the reaction mixture was added. The organic layer was then washed with water (2×50 ml) and brine (100 ml) before drying (MgSO$_4$) and evaporating. Purification by crystallisation (ethanol) gave a yellow crystalline solid mp. 139-141° C. which showed: $\delta_H$ (400 MHz, CDCl$_3$) 7.36 (1H, s, OH), 6.73 (1H, s, ArH), 6.57 (1H, s, ArH), 2.82-91 (2H, m, 6-CH$_2$), 2.66 (2H, q, J7.4, SCH$_2$), 1.36-2.55 (13H, m), 1.21 (3H, t, J 7.4, SCH$_2$CH$_3$) and 0.91 (3H, s, 18-CH$_3$); $\delta_C$ 220.5 (CO), 154.7, 140.0 (both C), 133.0 (CH), 132.2 (C), 115.7 (CH), 114.3 (C), 50.4 (CH), 48.0 (C), 43.9 (CH), 38.2 (CH), 35.9, 31.6, 31.1, 29.5, 26.5, 26.0, 21.7 (all CH$_2$), 15.2 and 14.0 (both CH$_3$); MS[FAB$^+$] 330.2 (100%, M+), HRMS[FAB$^+$] 330.165352, calculated 330.16535; Calculated C, 72.69, H, 7.93; Found C 72.9%, H, 7.99%.

2-Ethylsulfanyl-3-O-sulfamoyl-1,3,5[10]-estratriene (38)

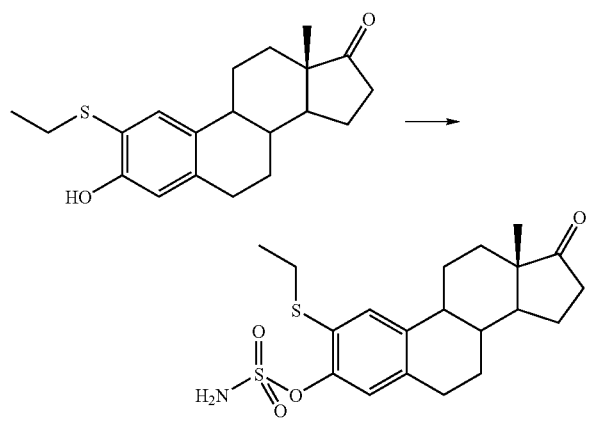

A stirred solution of 2-ethylsulfanylestrone (300 mg, 0.91 mmol) in dichloromethane (20 ml) was treated with 2,6-di-tert-butyl-4-methylpyridine (615 mg, 3 mmol) at room temperature. After a further five minutes sulfamoyl chloride (4.28 ml, 3 mmol, 0.7M in toluene) was added in a dropwise manner and the resultant yellow solution was stirred for 16 h. The reaction mixture was then poured onto water (25 ml), the organic layer separated and washed with water until neutral, dried and evaporated to give an oil. Column chromatography (chloroform: ethyl acetate 9:1) gave the desired sulfamate as a white crystalline solid mp 179-181° C. which showed $\delta_H$ 7.34 (1H, s, ArH), 7.16 (1H, s, ArH), 5.13 (2H, br s, NH$_{12}$), 2.86-2.98 (4H, m, SCH$_2$ and 6-CH$_2$), 1.40-2.57 (13H, m), 1.29 (3H, t, J 7.2, SCH$_2$CH$_3$) and 0.92 (3H, s, 18-CH$_3$); $\delta_C$ 220.3 (CO), 146.9, 139.5, 137.4 (all C), 129.1 (CH), 125.5 (C), 123.4 (CH), 50.4 (CH2), 47.9 (C), 44.2, 37.0 (CH), 35.6, 31.6, 29.1, 28.0, 26.2, 25.9, 21.7 (all CH$_2$), 14.5 and 13.9 (both CH$_3$); MS[FAB$^+$] $^{409.2}$ (100%, M+), HRMS[FAB$^+$] found 409.13815, calculated 409.13815.

Example 3

Synthesis of 2-Methylsulfanyl-3-O-sulfamoyl-17-deoxy-1,3,5[10]-estratriene (34)

3-O-Methoxymethylene-17-deoxy-1,3,5[10]-estratriene

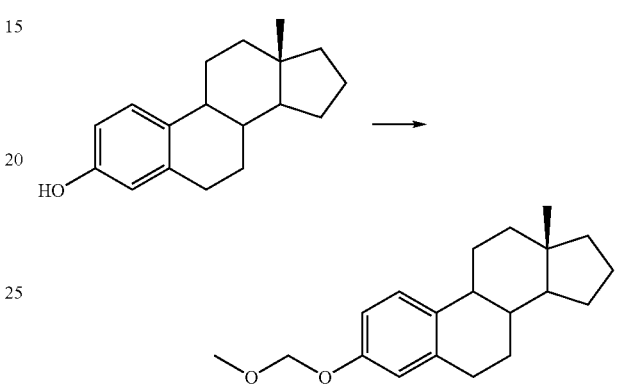

A stirred, 0° C., solution of 17-deoxyestrone (3.12 g, 12.2 mmol), in dimethylformamide (50 ml) was treated sodium hydride (731 mg, 18.3 mmol) in a portion wise manner. After 0.5 h stirring methyl chloromethyl ether (0.93 ml, 25 mmol) was added and the reaction mixture was left to stir overnight. Aqueous 2M ammonia (10 ml) was added to destroy excess chlorinated starting material and after a further 10 minutes ethyl acetate (200 ml) and brine (50 ml) were added. The organic layer was separated and washed five times with brine (50 ml aliquots), dried, evaporated and columned on silica gel (9:1 hexane:ethyl acetate as eluant) to give the desired protected 17-deoxyestrone as a clear colourless oil which showed $\delta_H$ 7.21 (1H, d, J8.5), 6.82 (1H, dd, J8.5 and 2.3, ArH), 6.77(1H, d, J2.3, ArH), 5.14(2H, s, OCH$_2$O), 3.47 (3H, s, OCH$_3$), 2.78-2.86 (2H, m, 6-CH$_2$), 1.15-2.30 (15H, m) and 0.73 (3H, s, 18-CH$_3$); $\delta_C$ 154.8, 138.0, 134.3, 126.3, 116.1, 113.6, 94.4, 55.9, 53.6, 44.2, 41.1, 40.6, 39.1, 38.9, 30.0, 28.2, 26.8, 25.3, 20.7 and 17.7.

2-Methylsulfanyl-3-O-methoxymethylene-7-deoxy-1,3,5 [10]-estratriene

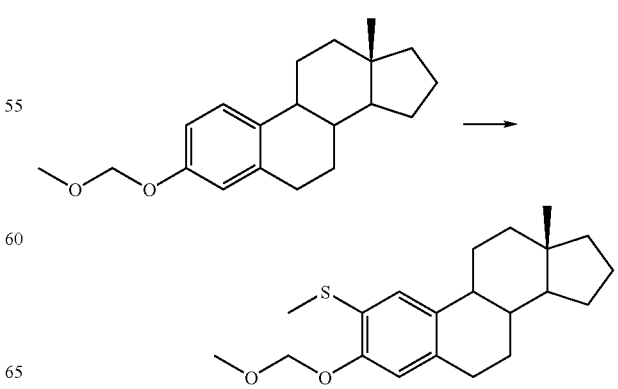

A stirred solution of protected estrone (2.78 g, 9.35 mmol) in THF (100 ml) was cooled in a dry ice/acetone bath to −78° C. before treating with sec-butyl lithium (28 ml, 21.5 mmol, 1.3 M solution in cyclohexane) in a dropwise manner over a period of 0.5 h. The anion maintained at this temperature for 1 h and was then quenched with dimethyl disulfide (4.2 ml, 47 mmol) over a period of five minutes and then allowed to warm to room temperature over a further 2 h. At this stage saturated ammonium chloride solution (10 ml) was added, the quenched solution diluted in diethyl ether (100 ml) and the organic layers were washed with saturated sodium hydrogen carbonate solution (3×50 ml), water (50 ml) and finally brine (50 ml) before drying (MgSO$_4$) and evaporating to yield the desired product as a spectroscopically pure yellow oil which showed dH 7.16 (1H, s, ArH), 6.81 (1H, s, ArH), 5.20 (2H, s, OCH$_2$O), 3.51 (3H, s, OMe), 2.78-2.86 (2H, m, 6-CH$_2$), 2.43 (3H, s, SMe), 1.10-2.36 (15H, m) and 0.74 (3H, s, 18CH$_3$).

2-Methylsulfanyl-17-deoxy-1,3,5[10]-estratrien-3-ol (33)

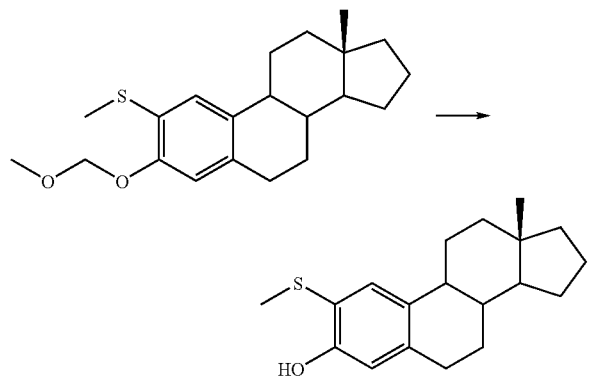

A 4M solution of methanolic HCl was prepared by cautious addition of acetyl chloride (6.1 ml) to ice cold methanol (15.6 ml), after five minutes stirring this solution was poured onto protected estrone X (1.8 g, 5.2 mmol). Sonication was applied to speed the dissolution of the protected estrone, a pink colour emerged in the reaction mixture after five minutes and, after a further ten minutes, ethyl acetate (100 ml), and then sufficient sodium hydrogen carbonate to neutralise the reaction mixture was added. The organic layer was then washed with water (2×50 ml) and brine (100 ml) before drying (MgSO$_4$) and evaporating. Purification by column chromatography (8:1 hexane:ethyl acetate) gave a clear colourless oil which showed $\delta_H$ 7.41 (1H, s, OH), 6.78 (1H, s, ArH), 6.45 (1H, s, ArH), 2.78-2.85 (2H, m, 6-CH2), 1.08-2.32 (18H, m [including 2.29 (3H, s, SMe)]) and 0.74 (3H, s, 18-CH$_3$); $\delta_C$ 153.7, 140.2, 133.6 (all C), 131.9 (CH), 117.4 (C), 114.4, 53.5, 43.9 (all CH), 41.0 (CH2), 40.5, 39.0 (both CH), 38.8, 29.8, 28.0, 26.9, 25.3, 20.7 (all CH$_2$), 20.4 and 17.6 (both CH$_3$)

2-Methylsulfanyl-3-O-sulfamoyl-17-deoxy-1,3,5[10]-estratriene (36)

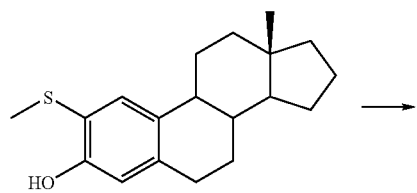

-continued

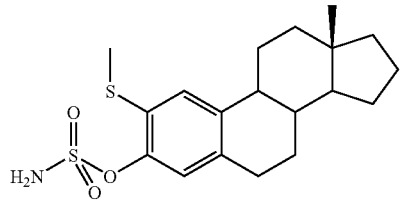

A stirred solution of 2-methylsulfanylestrone (520 mg, 1.72 mmol) in dichloromethane (20 ml) was treated with 2,6-di-tert-butyl-4-methylpyridine (883 mg, 4.3 mmol) at room temperature. After a further five minutes sulfamoyl chloride (6.15 ml, 4.3 mmol, 0.7M in toluene) was added in a dropwise manner and the resultant yellow solution was stirred for 16 h. The reaction mixture was then poured onto water (25 ml), the organic layer separated and washed with water until neutral, dried and evaporated to give an oil. Column chromatography (chloroform: ethyl acetate 9:1) gave the desired sulfamates as a white foam (470 mg, 72%) which was crystallised from ethanol/hexane to give a white crystalline solid mp 119-120° C. which showed $\delta_H$ 7.25 (1H, s, ArH), 7.10 (1H, s, ArH), 5.13 (2H, s, NH$_2$), 2.80-2.88 (2H, m, 6-CH$_2$), 2.46 (3H, s, SMe), 1.15-2.30 (15H, m) and 0.74 (3H, s, 18-CH$_3$); $\delta_C$ 145.6, 140.6, 136.7, 127.1, 126.1, 122.8, 53.5, 44.3, 41.0, 38.7, 38.6, 29.3, 27.8, 26.7, 25.2, 20.6, 17.5 and 16.2 MS[FAB$^+$] $^{381.2}$ (100%, M+) and 301.2 (50%); HRMS [FAB$^+$] found 381.143238, calculated 381.14324.

Example 5

Further Synthesis Examples 17-(4-tert-Butyl-benzyl)-13-methyl-2-methylsulfanyl-7,8,9,11,12,13,14,15,16,17-decahydro-6H-cyclopenta[a]phenanthrene-3,17-diol A

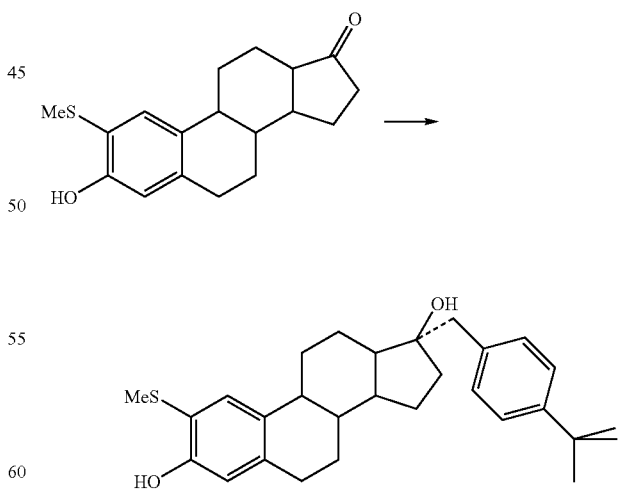

A solution of 4-(t-butyl) benzyl magnesium bromide was prepared by dropwise addition of an ethereal solution of 4-(t-butyl)benzyl bromide (3.67 ml, 20 mmol in 20 ml ether) to magnesium turnings (1.48 g, 61 mmol) at room temperature over a period of 0.5 h. The resultant mixture was stirred for a further 2 h before adding 10 ml of the resultant solution of Grignard reagent to a rt stirred solution of 2-methylsulfanyl estrone (316 mg, 1 mmol) in THF (20 ml). After overnight stirring the reaction was quenched with saturated ammonium chloride solution (10 ml), extracted with ethyl acetate (3×50 ml), the organic layer dried (MgSO4) and evaporated. To facilitate chromatographic separation of product and starting material the crude product was dissolved in methanol (30 ml) and treated with sodium borohydride (75 mg, 2 mmol). After a standard work-up the product was purified by column chromatography (hexane/ethyl acetate gradient elution) to give the desired product, 17-(4-tert-Butyl-benzyl)-13-methyl-2-methylsulfanyl-7,8,9,11,12,13,14,15,16,17-decahydro-6H-cyclopenta[a]phenanthrene-3,17-diol, as a white solid which showed $\delta_H$ 7.44 (1H, s, OH), 7.35 (2H, d, J 8.2, ArH), 7.22 (2H, d, J 8.2, ArH), 6.74 (1H, s, ArH), 6.49 (1H, s, ArH), 2.89 (1H, d, J 13.3, ArCH$_a$H$_b$), 2.84-2.89 (2H, in, 6-CH$_2$), 2.65 (1H, d, J 13.3, ArCH$_a$H$_b$), 1.26-2.42 (25H, in, including 2.31 (3H, s, SMe) and 1.34 (9H, S, CMe$_3$)) and 0.98 (3H, s, 18-CH$_3$); $\delta_C$ 153.9, 148.9, 140.1, 134.9, 133.2 (all C), 131.9, 130.5, 125.0 (all CH), 117.6 (C), 114.4 (CH), 82.9 (C), 49.5 (CH), 46.8 (C), 43.8 (CH), 41.9 (CH$_2$), 39.5 (CH), 34.5 (C), 33.8 (CH$_2$), 31.5 (CH$_3$), 31.4, 29.7, 27.4, 26.5, 23.4 (all CH$_2$), 20.4 and 14.6 (both CH$_3$).

Sulfamic acid 17-(4-tert-butyl-benzyl)-17-hydroxy-13-methyl-2-methylsulfanyl-7,8, 9,11,12,13,14,15,16,17-decahydro-6H-cyclopenta[a]phenanthren-3-yl ester B

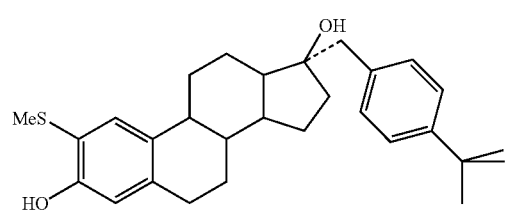

The previously prepared estradiol (130 mg, 0.28 mmol) was dissolved in dichloromethane (10 ml) and treated with di-t-butyl methylpyridine (172 mg, 0.84 mmol) and then sulfamoyl chloride (1.27 ml of a 0.7M solution in toluene, 0.89 mmol). After standard workup the desired product (42 mg) was isolated by column chromatography as a white powder mp. 135° C. which showed $\delta_H$ 7.15-7.36 (6H, m, ArH), 5.08 (2H, s, NH$_2$), 2.84-2.95 (3H, m, ArCH and 6-CH$_2$), 2.61-2.66 (1H, m, ArCH), 2.48 (3H, s, SMe), 1.20-2.45 (23H, m, icluding 1.32 (9H, s, tBu)) and 0.96 (3H, s, 18-CH$_3$): $\delta_C$ 149.1, 145.8, 140.2, 136.7, 134.7, 130.5, 127.3, 126.1, 125.0, 123.0, 109.7, 49.5, 46.7, 44.2, 41.8, 39.2, 34.5, 33.7, 31.5, 29.2, 27.3, 26.4, 23.4, 16.3, and 14.6.

17-Benzyl-13-methyl-2-methylsulfanyl-7,8,9,11,12,13,14, 15,16,17-decahydro-6H-cyclopenta[a]phenanthrene-3,17-diol C

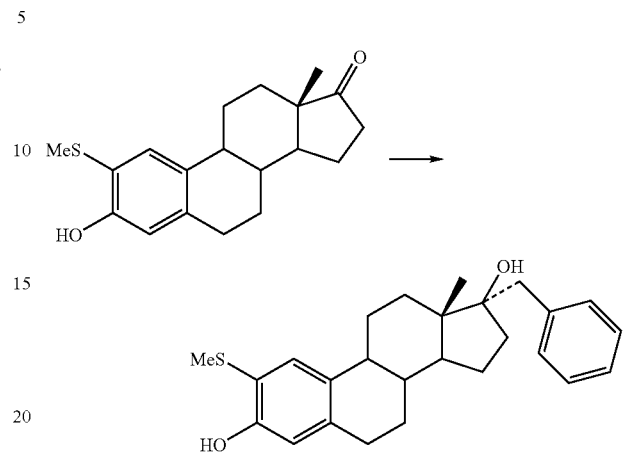

In the same manner as the synthesis of compound A 2-methylsulfanyl estrone (316 mg, I nmol) was reacted with benzyl magnesium chloride (5 ml of a two molar solution in THF) to give the desired estradiol as a white powder (200 mg) which showed $\delta_H$ 7.43 (1H, s, OH), 7.24-7.35 (5H, m, ArH), 6.73 (1H, s, ArH), 6.48 (1H, s, ArH), 2.93 (1H, d, J 13.3, PhH$_a$H$_b$), 2.84-2.89 (2H, m, 6-CH$_2$) 2.67 (1H, d, J 13.3, PhH$_a$H$_b$), 1.26-2.42 (17H, m, including 2.31 (3H, s, SMe)) and 0.97 (3H, s, 18-CH$_3$); $\delta_C$ 153.9, 140.1, 138.2, 133.2, 131.9, 130.9, 128.0, 126.2, 117.2, 114.4, 83.0, 49.6, 46.9, 43.9, 42.5, 39.6, 33.9, 31.5, 29.7, 27.5, 26.5, 23.4, 20.4 and 14.6.

Sulfamic acid 17-benzyl-17-hydroxy-13-methyl-2-methylsulfanyl-7,8,9,11,12,13,14, 15,16,17-decahydro-6H-cyclopenta[a]phenanthren-3-yl ester

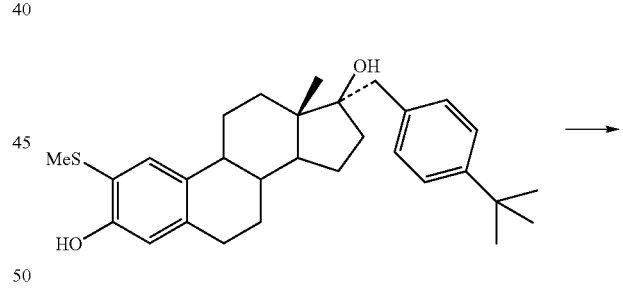

In the same manner as the synthesis of compound B estradiol C (142 mg, 0.348 mmol) was reacted with DBMP (214 mg, 1.04 mmol) and sulfamoyl chloride (1.59 ml of 0.7M toluene solution, 1.11 mmol) to obtain sulfamate D (40 mg) as a white powder mp 178-180° C.

Example 6

Biological Data

The compounds identified in the table below were synthesied.

| Comound | X | Y | Z |
|---|---|---|---|
| 30 | $OSO_2NH_2$ | SMe | β-OH, α-Bn |
| 31 | OH | SMe | β-OH, α-4-(tBu)Bn |
| 32 | $OSO_2NH_2$ | SMe | β-OH, α-4-(tBu)Bn |
| 33 | OH | SMe | $CH_2$ |
| 34 | $OSO_2NH_2$ | SMe | $CH_2$ |
| 35 | OH | SMe | C=O |
| 36 | $OSO_2NH_2$ | SMe | C=O |
| 37 | OH | SEt | C=O |
| 38 | $OSO_2NH_2$ | SEt | C=O |

The STS inhibition provided by the compounds was determined in accordance with the placental microsomes assay of Protocol 4 and a plate assay.

sodium azide). Cells were analysed by confocal microscopy using a Zeiss Axiovert 100 M microscope equipped with the LSM 510 confocal system (Zeiss, Jena, Germany).

| Compound | Placental Microsomes, % inhibition | | | | | Plate Assay, % inhibition | | |
|---|---|---|---|---|---|---|---|---|
| | 10 μM | 1 μM | 100 nM | 10 nM | IC50 nM | 0.1 μM | 1 μM | 10 μM |
| 30 | 97.4 | 93.0 | 69.7 | 15.5 | 44 | <1 | <1 | 31 |
| 31 | — | — | — | — | — | <1 | <1 | 50 |
| 32 | 86.4 | 81.8 | 56.0 | 17.6 | 80 | <1 | <1 | 48 |
| 35 | — | — | — | — | — | <1 | 1 | 11 |
| 36* | — | 86.9 | — | 5.4 | 120 | 3 | 53 | 55 |
| 37 | — | — | — | — | — | <1 | <4 | 14 |
| 38 | — | 66.0 | — | <5 | — | <1 | 1 | 16 |
| EMATE | 99.5 | 97.8 | 85.1 | 27.3 | 18 | — | — | — |

*IC50 2.5 nM T47D cells.

Example 7

Cell Cycle and Apoptosis Analysis

MCF7, CAL51, CAMA1 and ZR-75-1 breast cancer derived cell lines were obtained from ATCC (MCF7, CAMA1, ZR-75-1) or from the Dutrillaux laboratory (CAL51) (22) and maintained in Dulbecco's modified Eagle's medium (DMEM) supplemented with 10% (v/v) fetal calf serum and antibiotics.

DNA content was determined by flow cytometric analysis of propidium iodide stained cells and TdT-mediated dUTP-nick end labelling (TUNEL), respectively, as described (20). The proportion of cells in G2/M phase of the cell cycle was calculated as a proportion of cells with 2N to 4N DNA content. The proportion of cells with <G1 DNA content was calculated as a percentage of total cells.

To determine the proportion of cells in mitosis, drug treated cells were collected by trypsinisation and cytospins prepared. Cells were fixed in ice cold methanol for 5 minutes, air dried and DNA was stained using propidium iodide (PI) (0.1 mg/ml in phosphate buffered saline (PBS) containing 10% (v/v) newborn calf serum and 0.05% (w/v)

We examined whether the differential sensitivity of breast cancer cell lines to the growth inhibitory effects of the compounds of the present invention. Compounds of the present invention were shown to have such an effect. In particular Compound 36 induced cells to become rounded and detached from the plate/flask, indicating that the cells were undergoing microtubule disruption, mitotic/cell cycle arrest and apoptosis.

The invention will now be further described by the following numbered paragraphs:

1. Use of a compound in the manufacture of a medicament to inhibit superoxide dismutase (SOD) or for use in the therapy of a condition or disease associated with SOD wherein the compound is of Formula I Formula I

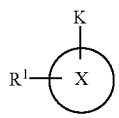

wherein:

X is a ring having at least 4 atoms in the ring;

K is a hydrocarbyl group;

$R^1$ is a halogen or a group of the formula $-L^1-Z-R^{1'}$, wherein $L^1$ is an optional linker group, Z is O or S and $R^{1'}$ is a hydrocarbyl group or H;

with the proviso that the compound is other than 2-methoxy-17β-oestradiol, 2-methoxyoestrone and 2-hydroxyestradiol.

2. Use according to paragraph 1 wherein X is a 6 membered ring.

3. Use according to paragraph 1 or 2 having the Formula II

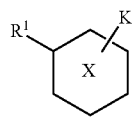

Formula II

4. Use according to any one of the preceding paragraphs wherein K is a cyclic group.

5. Use according to any one of the preceding paragraphs wherein the compound is a polycyclic compound.

6. Use according to any one of the preceding paragraphs wherein X in combination with K is a polycyclic ring structure.

7. Use according to any one of the preceding paragraphs having the Formula III

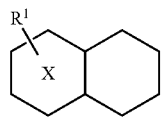

Formula III

8. Use according to any one of the preceding paragraphs having the Formula IV

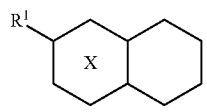

Formula IV

9. Use according to any one of the preceding paragraphs having the Formula V

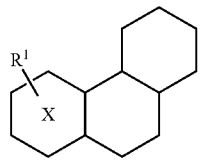

Formula V

10. Use according to any one of the preceding paragraphs having the Formula VI

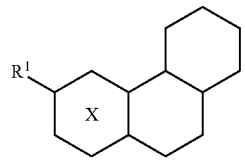

Formula VI

11. Use according to any one of the preceding paragraphs wherein X in combination with K is a steroidal ring structure.

12. Use according to any one of the preceding paragraphs wherein the compound X in combination with K mimics a steroidal structure.

13. Use according to any one of the preceding paragraphs having Formula VII

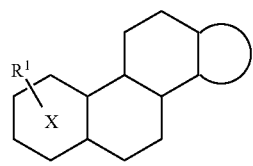

Formula VII

14. Use according to any one of the preceding paragraphs having Formula VIII

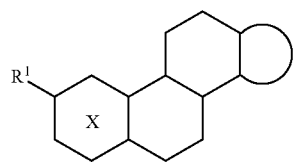

Formula VIII

15. Use according to any one of the preceding paragraphs having Formula IX

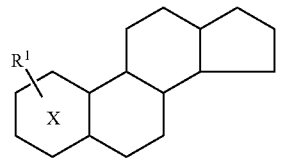

Formula IX

16. Use according to any one of the preceding paragraphs having Formula X

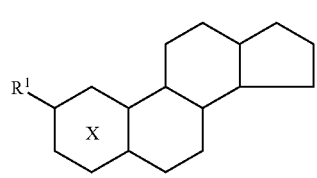

Formula X

17. Use according to any one of the preceding paragraphs wherein $R^1$ is a halogen.

18. Use according to paragraph 17 wherein the halogen is selected from F and Cl.

19. Use according to any one of paragraphs 1 to 16 wherein $R^1$ is a group of the formula -L$^1$-Z-R$^{1'}$.

20. Use according to paragraph 19 wherein $R^1$ is a group of the formula -Z-R$^{1'}$.

21. Use according to paragraph 19 or 20 wherein Z is O.

22. Use according to paragraph 19 or 20 wherein Z is S.

23. Use according to any one paragraphs 19 to 22 wherein $R^{1'}$ is an alkyl group.

24. Use according to any one of paragraphs 19 to 23 wherein $R^{1'}$ is a $C_1$-$C_{10}$ alkyl group.

25. Use according to any one of paragraphs 19 to 24 wherein $R^{1'}$ is a $C_1$-$C_6$ alkyl group.

26. Use according to any one of paragraphs 19 to 25 wherein $R^{1'}$ is a $C_1$-$C_3$ alkyl group.

27. Use according to any one of paragraphs 19 to 26 wherein $R^{1'}$ is —CH$_3$ or —CH$_2$CH$_3$.

28. Use according to any one of paragraphs 1 to 16 wherein $R^1$ is selected from —SCH$_3$, OCH$_3$, —SCH$_2$CH$_3$, —OCH$_2$CH$_3$, —F, and —Cl.

29. Use according to paragraph 1 wherein the compound is selected from compounds of the formulae

| | $R_1$ | $R_2$ | $R_3$ | X | |
|---|---|---|---|---|---|
| | H | OH | MeS | CH(β-OH) | 1 |
| | H | OH | EtO | CH(β-OH) | 2 |
| | H | OH | MeO | CH(β-OH) | 4 |
| | H | OH | EtS | CH(β-OH) | 6 |
| | H | OH | EtO | C=O | 7 |
| | H | OH | MeS | C=O | 8 |
| | H | NH$_2$ | MeO | C=O | 9 |
| | H | OH | EtS | C=O | 10 |
| | H | OH | F | C=O | 11 |
| | H | OH | Cl | C=O | 12 |
| | H | OH | MeO | C(β-OH)(α-Bn) | 13 |
| | H | OH | H$_2$C=CHCH$_2$ | C=O | 15 |
| | H | OH | I | C=O | 16 |
| | H | OH | CHF$_2$ | C=O | 17 |
| | H | OH | MeSO | C=O | 18 |
| | H | OH | MeSO$_2$ | C=O | 19 |
| | H | OH | NO$_2$ | C=O | 20 |
| | H | OH | Et | C=O | 21 |
| | NO$_2$ | OH | MeO | C=O | 22 |
| | H | OH | MeO | C[β-OH][α-(4-$^t$Bu)Bn] | 23 |
| | H | OSO$_2$NH$_2$ | H | C=O | 24 |
| | H | OSO$_2$NH$_2$ | MeO | C=O | 25 |
| | H | OSO$_2$NH$_2$ | Et | C=O | 26 |

30. Use according to paragraph 1 wherein, when R1 is a methoxy group or hydroxy group, X in combination with K is a non-steroidal ring structure.

31. Use according to paragraph 1 wherein the compound is non-steroidal.

32. Use according to paragraph 1 wherein X in combination with K is a non-steroidal ring structure.

33. Use according to paragraph 1 wherein $R^{1'}$ is a $C_2$-$C_{10}$ alkyl group, preferably a $C_2$-$C_6$ alkyl group, preferably a $C_2$ or $C_3$ alkyl group.

34. Use according to paragraph 1 wherein when Z is O, $R^{1'}$ is a $C_2$-$C_{10}$ alkyl group; and when Z is S, $R^{1'}$ is a hydrocarbyl group or H 35. A compound of having Formula IX

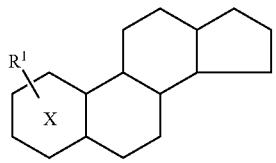

Formula IX wherein $R^1$ is a group of the formula -$L^1$-S-$R^{1'}$, wherein $L^1$ is an optional linker group, and $R^{1'}$ is a hydrocarbyl group or H.

36. A compound of having Formula X

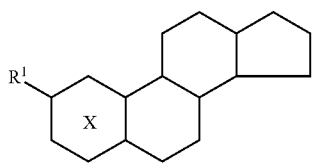

Formula X wherein $R^1$ is a group of the formula -$L^1$-S-$R^{1'}$, wherein $L^1$ is an optional linker group, and $R^{1'}$ is a hydrocarbyl group or H.

37. A compound according to paragraph 35 or 36 wherein $R^1$ is a group of the formula —S—$R^{1'}$.

38. A compound according to paragraph 35, 36 or 37 wherein $R^1$ is an alkyl group.

39. A compound according to paragraph 38 wherein $R^{1'}$ is a $C_1$-$C_{10}$ alkyl group.

40. A compound according to paragraph 38 wherein $R^{1'}$ is a $C_1$-$C_6$ alkyl group.

41. A compound according to paragraph 38 wherein $R^{1'}$ is a $C_1$-$C_3$ alkyl group.

42. A compound according to paragraph 38 wherein $R^{1'}$ is —$CH_3$ or —$CH_2CH_3$.

43. A compound according to paragraph 35 or 36 wherein $R^1$ is selected from —$SCH_3$, —$SCH_2CH_3$, —$S(O)CH_3$, and —$S(O)(O)CH_3$ 44. A compound according to any one of paragraphs 35 to 43 for use in medicine.

45 A pharmaceutical composition comprising the compound according to any one of Paragraphs 35 to 43 optionally admixed with a pharmaceutically acceptable carrier, diluent, excipient or adjuvant.

46. Use of a compound according to any one of paragraphs 35 to 43 in the manufacture of a medicament for the inhibition of SOD or for use in the therapy of a condition or disease associated with SOD.

47. A compound of Formula XI

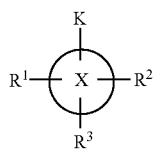

Formula XI wherein:

X is a ring having at least 4 atoms in the ring;

K is a hydrocarbyl group;

$R^1$ is an optional group of the formula -$L^1$-S-$R^{1'}$, wherein $L^1$ is an optional linker group and $R^{1'}$ is a hydrocarbyl group;

$R^2$ is an optional group of the formula -$L^2$-S-$R^{2'}$, wherein $L^2$ is an optional linker group and $R^{2'}$ is a hydrocarbyl group;

$R^3$ is any one of a sulphamate group, a phosphonate group, a thiophosphonate group, a sulphonate group or a sulphonamide group;

wherein at least one of $R^1$ and $R^2$ is present;

and wherein said compound is capable of inhibiting steroid sulphatase (STS) activity and/or is capable of acting as a modulator of cell cycling and/or as a modulator of apoptosis and/or as a modulator of cell growth.

48. A compound according to paragraph 47 having Formula XII

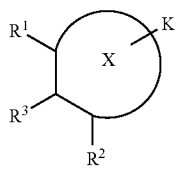

Formula XII

49. A compound according to paragraph 47 or 48 wherein X in combination with K mimics a steroidal structure.

50. A compound according to any one of the preceding paragraphs wherein K is a cyclic group.

51. A compound according to any one of the preceding paragraphs wherein X is a six-membered ring.

52. A compound according to paragraph 51 having Formula XIII

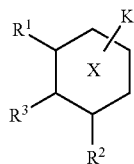

Formula XIII

53. A compound according to any one of the preceding paragraphs wherein X in combination with K is a steroidal ring structure.

54. A compound according to paragraph 53 having Formula XIV

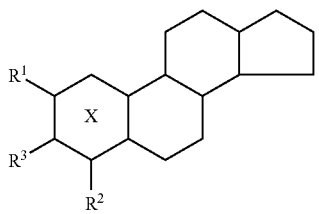

Formula XIV

55. A compound according to any one of the preceding paragraphs wherein $R^3$ is a sulphamate group.

56. A compound according to any one of the preceding paragraphs wherein $R^{1'}$ and/or $R^{2'}$ are alkyl groups.

57. A compound according to any one of the preceding paragraphs wherein $R^{1'}$ and/or $R^{2'}$ are $C_1$-$C_{10}$, preferably $C_1$-$C_6$, preferably $C_1$-$C_3$ alkyl groups.

58. A compound according to any one of the preceding paragraphs wherein $R^{1'}$ and/or $R^{2'}$ are —$CH_3$ or —$CH_2CH_3$.

59. A compound according to paragraph 47 of the formula

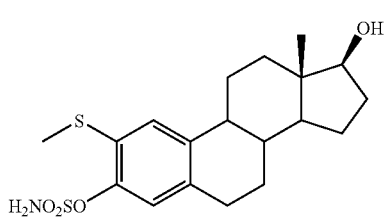

60. A compound according to paragraph 47 of the formula

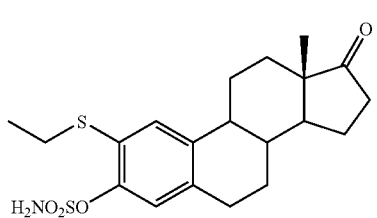

61. A method comprising (a) performing a steroid sulphatase assay with one or more candidate compounds having the formula as defined in any one of the preceding paragraphs; (b) determining whether one or more of said candidate compounds is/are capable of modulating STS activity and/or cell cycling and/or cell growth and/or apoptosis; and (c) selecting one or more of said candidate compounds that is/are capable of modulating STS activity and/or cell cycling and/or cell growth and/or apoptosis.

62. A method comprising (a) performing a steroid sulphatase assay with one or more candidate compounds having the formula as defined in any one of paragraphs 47 to 60; (b) determining whether one or more of said candidate compounds is/are capable of inhibiting STS activity; and (c) selecting one or more of said candidate compounds that is/are capable of inhibiting STS activity and/or cell cycling and/or cell growth and/or apoptosis.

63. A compound identified by the method according to paragraph 61 or paragraph 62.

64. A compound according to any one of paragraphs 47 to 60 or 63 for use in medicine.

65. A pharmaceutical composition comprising the compound according to any one of paragraphs 47 to 60 or 63 optionally admixed with a pharmaceutically acceptable carrier, diluent, excipient or adjuvant.

66. Use of a compound according to any one of paragraphs 47 to 60 or 63 in the manufacture of a medicament for use in the therapy of a condition or disease associated with STS and/or cell cycling and/or apoptosis and/or cell growth.

67. Use of a compound according to any one of paragraphs 47 to 60 or 63 in the manufacture of a medicament for use in the therapy of a condition or disease associated with adverse STS levels and/or cell cycling and/or apoptosis and/or cell growth.

All publications and patents and patent applications mentioned in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

What is claimed is:

1. A compound of Formula XI

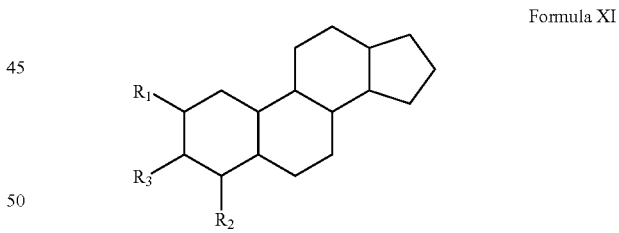

Formula XI wherein:
the rings may be independently substituted or unsubstituted, saturated or unsaturated;
$R^1$ is an optional group of the formula —S—$R^{1'}$, wherein $R^{1'}$ is an alkyl group;
$R^2$ is an optional group of the formula —S—$R^{2'}$, wherein $R^{2'}$ is an alkyl group;
$R^3$ is a sulphamate group;
wherein at least one of $R^1$ and $R^2$ is present;
and wherein said compound is capable of inhibiting steroid sulphatase (STS) activity and/or is capable of acting as a modulator of cell cycling and/or as a modulator of apoptosis and/or as a modulator of cell growth.

2. A compound according to claim 1 wherein $R^{1'}$ and/or $R^{2'}$ are $C_1$-$C_{10}$ alkyl groups.

3. A compound according to claim 1 wherein $R^{1'}$ and/or $R^{2'}$ are $C_1$-$C_6$ alkyl groups.

4. A compound according to claim 1 wherein $R^{1'}$ and/or $R^{2'}$ are $C_1$-$C_3$ alkyl groups.

5. A compound according to claim 1 wherein $R^{1'}$ and/or $R^{2'}$ are —$CH_3$ or —$CH_2CH_3$.

6. A compound according to claim 1 of the formula

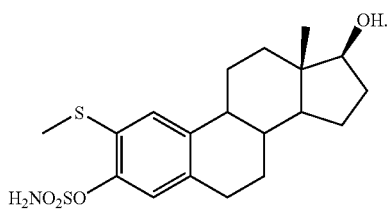

7. A compound according to claim 1 of the formula

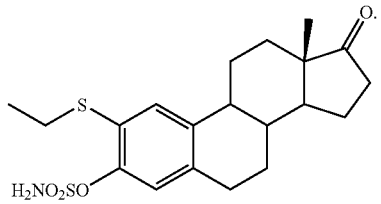

8. A pharmaceutical composition comprising the compound according to claim 1 optionally admixed with a pharmaceutically acceptable carrier, diluent, excipient or adjuvant.

\* \* \* \* \*

UNITED STATES PATENT AND TRADEMARK OFFICE
CERTIFICATE OF CORRECTION

PATENT NO. : 7,342,004 B2  Page 1 of 1
APPLICATION NO. : 10/367623
DATED : March 11, 2008
INVENTOR(S) : Barry Victor Lloyd Potter et al.

It is certified that error appears in the above-identified patent and that said Letters Patent is hereby corrected as shown below:

Title page, item (12)
United States Patent should read
--"Lloyd" Potter, et al.--

Signed and Sealed this

Twenty-third Day of December, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,342,004 B2 | Page 1 of 1 |
| APPLICATION NO. | : 10/367623 | |
| DATED | : March 11, 2008 | |
| INVENTOR(S) | : Barry Victor Lloyd Potter et al. | |

It is certified that error appears in the above-identified patent and that said Letters Patent is hereby corrected as shown below:

Title page, item (12)
United States Patent should read
    --Potter, et al.--

This certificate supersedes the Certificate of Correction issued December 23, 2008.

Signed and Sealed this

Tenth Day of March, 2009

JOHN DOLL
*Acting Director of the United States Patent and Trademark Office*